US012220534B2

(12) United States Patent
Van Schalkwyk et al.

(10) Patent No.: US 12,220,534 B2
(45) Date of Patent: Feb. 11, 2025

(54) BREATHING ASSISTANCE APPARATUS AND/OR COMPONENTS THEREOF

(71) Applicant: Fisher & Paykel Healthcare Limited, Auckland (NZ)

(72) Inventors: Andre Van Schalkwyk, Auckland (NZ); Rachel Adeline Miller, Auckland (NZ); Stephen William Kavermann, Auckland (NZ); Ella Marie Meisel, Auckland (NZ); Alexander Edwin Mackenzie, Auckland (NZ); Oliver Michael Clarke, Auckland (NZ); Philip John Dickinson, Auckland (NZ); Samuel Carey Mathew Sanson, Auckland (NZ); Hayk Noobar Antranik Yaghobian, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 880 days.

(21) Appl. No.: 17/309,192

(22) PCT Filed: Nov. 5, 2019

(86) PCT No.: PCT/IB2019/059463
§ 371 (c)(1),
(2) Date: May 4, 2021

(87) PCT Pub. No.: WO2020/095186
PCT Pub. Date: May 14, 2020

(65) Prior Publication Data
US 2022/0023576 A1 Jan. 27, 2022

Related U.S. Application Data

(60) Provisional application No. 62/925,971, filed on Oct. 25, 2019, provisional application No. 62/890,866, (Continued)

(51) Int. Cl.
*A61M 16/08* (2006.01)
*A61M 16/00* (2006.01)
(Continued)

(52) U.S. Cl.
CPC ...... *A61M 16/0816* (2013.01); *A61M 16/021* (2017.08); *A61M 16/0666* (2013.01); *A61M 16/105* (2013.01)

(58) Field of Classification Search
CPC .............. A61M 16/0875; A61M 16/08–0891; A61M 16/16–168; A61M 16/109; A61M 16/0816; A61M 16/0057
See application file for complete search history.

(56) References Cited

U.S. PATENT DOCUMENTS 10,245,407 B2  4/2019  Osborne et al.
11,278,700 B2  3/2022  Van Schalkwyk et al.
(Continued)

FOREIGN PATENT DOCUMENTS

CN    101516430 A    8/2009
CN    103143092 A    6/2013
(Continued)

OTHER PUBLICATIONS

International Search Report for International Application No. PCT/IB2019/059463 dated.

*Primary Examiner* — Kendra D Carter
*Assistant Examiner* — Mautin I Ashimiu
(74) *Attorney, Agent, or Firm* — VIA LLP

(57) ABSTRACT

A breathing assistance apparatus has a housing with an engagement feature and an electrical component in the housing and a removable component. The electrical component has a receptacle. The removable component has an electrical connector that is a close or tight fit in the receptacle of the electrical component to assist with holding the removable component in connection with the electrical component. The removable component has a tab with a terminal end portion that can be flexed relative to the rest of the removable component. An engagement feature is provided on the terminal end portion of the tab and engages with the engagement feature of the housing to inhibit disconnection of the removable component from the housing in the absence of actuating the terminal end portion of the removable component to flex the tab.

13 Claims, 44 Drawing Sheets

Related U.S. Application Data filed on Aug. 23, 2019, provisional application No. 62/755,936, filed on Nov. 5, 2018.

(51) Int. Cl.
*A61M 16/06* (2006.01)
*A61M 16/10* (2006.01)
*A61M 16/16* (2006.01)
*A61M 16/20* (2006.01)
*A61M 39/10* (2006.01)

(56) References Cited

U.S. PATENT DOCUMENTS

| | | | |
|---|---|---|---|
| 2012/0174922 A1* | 7/2012 | Virr | A61M 16/106 |
| | | | 128/206.28 |
| 2013/0340757 A1 | 12/2013 | Smith et al. | |
| 2015/0136127 A1* | 5/2015 | Dimatteo | A61M 16/16 |
| | | | 439/13 |
| 2015/0283350 A1 | 10/2015 | Miller et al. | |
| 2015/0306332 A1 | 10/2015 | Bafile et al. | |
| 2016/0199612 A1* | 7/2016 | Foote | A61M 16/0875 |
| | | | 128/202.27 |
| 2016/0310689 A1 | 10/2016 | Osborne et al. | |
| 2018/0043125 A1* | 2/2018 | Bencke | A61M 16/0816 |
| 2018/0185606 A1 | 7/2018 | Van Schalkwyk et al. | |
| 2021/0016076 A1 | 1/2021 | Osborne et al. | |
| 2022/0118208 A1 | 4/2022 | Livingston et al. | |

FOREIGN PATENT DOCUMENTS

| | | | | |
|---|---|---|---|---|
| CN | 103463722 A | | 12/2013 | |
| JP | 2015-524336 | | 8/2015 | |
| JP | 2016-530038 | | 9/2016 | |
| JP | 2017-500126 | | 1/2017 | |
| JP | 2018-518297 | | 7/2018 | |
| WO | WO 2007/019627 A1 | | 2/2007 | |
| WO | WO 2011/056080 | | 5/2011 | |
| WO | WO 2015/038013 | | 3/2015 | |
| WO | WO 2016/207838 A9 | | 12/2016 | |
| WO | WO-2016207838 A1 * | 12/2016 | | A61M 16/0003 |
| WO | WO 2017095241 A2 | | 6/2017 | |
| WO | WO 2018/074935 A1 | | 4/2018 | |

* cited by examiner

BREATHING ASSISTANCE APPARATUS AND/OR COMPONENTS THEREOF

TECHNICAL FIELD

The present invention relates to a breathing assistance apparatus and/or components thereof.

BACKGROUND ART

Breathing assistance apparatuses are used in various environments such as hospital, medical facility, residential care, or home environments to deliver a flow of gas to users or patients. The breathing assistance apparatuses come in various forms, such as a standalone humidifier apparatus, a continuous positive airway pressure (CPAP) apparatus, a high flow apparatus, or a ventilator.

A standalone humidifier apparatus can deliver heated and humidified gases for various medical procedures, including respiratory therapy, laparoscopy, and the like. These apparatuses can be configured to control temperature and/or humidity. The apparatuses can also include medical circuits comprising various components that can be used to transport heated and/or humidified gases to and from patients. For example, in some breathing circuits, gases inhaled by a patient are delivered from a heater-humidifier through an inspiratory tube or conduit. As another example, tubes can deliver humidified gas (commonly $CO_2$) into the abdominal cavity in insufflation circuits. This can help prevent desiccation or 'drying out' of the patient's internal organs, and can decrease the amount of time needed for recovery from surgery. Heater wires may extend inside of at least a portion of the tubing forming the circuit to prevent or at least reduce the likelihood of the formation of significant condensation.

A standalone humidifier apparatus would typically include a heater base and a humidification liquid chamber. The heater base can comprise a heater plate. The liquid chamber can be configured to hold a volume of a liquid, such as water. The heater plate can be configured to heat the volume of liquid held within the liquid chamber to produce vapour.

The liquid chamber is removable from the heater base to allow the liquid chamber to be more readily sterilized or disposed, or to re-fill the chamber with liquid. The body of the liquid chamber can be formed from a non-conductive glass or plastics material but the liquid chamber can also include conductive components. For instance, the liquid chamber can include a highly heat-conductive base (for example, an aluminum base) contacting or associated with the heater plate on the heater base.

The heater base can also include electronic controls such as a master controller. In response to user-set humidity or temperature values input via a user interface and other inputs, the master controller determines when (or to what level) to energize the heater plate to heat the liquid within the liquid chamber.

The standalone humidifier apparatus can include a gases supply to deliver gases to the liquid chamber. In some configurations, the gases supply can comprise a ventilator, blower, or any other suitable source of pressurized gases suitable for breathing or use in medical procedures.

A standalone humidifier apparatus can be used with breathing therapies, positive pressure apparatus, noninvasive ventilation, surgical procedures including but not limited to laparoscopy, and the like. Desirably, the humidifier apparatus can be adapted to supply humidity or vapour to a supply of gases. The humidifier apparatus can be used with continuous, variable, or bi-level PAP systems or other form of respiratory therapy. In some configurations, the humidifier apparatus can be integrated into a system that delivers any such types of therapy.

An exemplary standalone humidifier apparatus is described in WO 2015/038013.

A CPAP apparatus is a gases supply and optionally gases humidification apparatus. The apparatus is operable to provide respiratory assistance to patients or users who require a supply of gas (humidified or otherwise) at positive pressure for the treatment of diseases such as Obstructive Sleep Apnea (OSA), snoring, or Chronic Obstructive Pulmonary Disease (COPD) and the like. A CPAP apparatus would typically include a humidification liquid chamber, so as to form a combined assisted breathing unit and humidifier.

CPAP apparatuses, when used with a humidifier, typically have a structure where gases at a required pressure are delivered from an assisted breathing unit or blower unit to a liquid chamber downstream from the blower. As the gases pass through the liquid chamber, they become saturated with liquid vapour (e.g. water vapour). A flexible tubular gases conduit delivers the gases to a user or patient downstream from the humidifier chamber.

An exemplary CPAP apparatus is described in WO 2011/056080.

A high flow apparatus may be used to deliver a high gas flow or high flow therapy to a patient to assist with breathing and/or treat breathing disorders including chronic obstructive pulmonary disease (COPD). A high flow apparatus includes a gases supply and typically includes a humidification apparatus.

The breathing assistance apparatuses typically have one or more accessories such as a breathing conduit and a patient interface such as a cannula or mask for delivering gases to a patient. The conduit enables gases to be delivered from the housing of the breathing assistance apparatus to the patient. For example, the apparatus may be placed on a floor or other support surface, and the patient may be in a bed. The breathing assistance apparatus may have a recess for receipt of a humidifier liquid chamber. The liquid chamber will receive liquid from, for example, a flexible liquid bag that delivers liquid to a humidifier liquid chamber via one or more tubes. Alternatively, the liquid chamber can be removed and refilled as required. The recess will contain a heater plate to heat the liquid chamber, to humidify gases passing through the liquid chamber. The humidified gases are then delivered to the patient.

SUMMARY

In accordance with certain features, aspects and advantages of at least one of the embodiments disclosed herein, a filter module for a breathing assistance apparatus is disclosed, the filter module comprising: a filter body having a plurality of walls including a first wall, an opposed second wall, and an upper wall extending between the first wall and the second wall, the filter body defining at least one filter chamber; and a gas port that is in communication with at least one filter chamber in the filter body, the gas port extending upwardly from the upper wall and being positioned closer to one of the first wall and second wall than it is to a centre of the upper wall, wherein the gas port is configured to interact with a handle of the breathing assistance apparatus.

In some configurations, the filter body comprises a lower wall opposite to the upper wall, wherein the upper wall is oriented on an angle so as to be non-parallel with the lower wall.

In some configurations, the upper wall is oriented on an angle of between about 2 degrees and about 10 degrees, optionally between about 2 degrees and about 5 degrees, optionally about 3 degrees, relative to the lower wall.

In some configurations, the second wall is taller than the first wall.

In some configurations, the gas port is positioned at or adjacent the second wall.

In some configurations, the lower wall comprises one or more lower ports to deliver gases into at least one filter chamber in the filter body.

In some configurations, the filter comprises a filter medium to filter gases as they exit the filter chamber(s).

Additionally, in accordance with certain features, aspects and advantages of at least one of the embodiments disclosed herein, a breathing assistance apparatus is disclosed, the breathing assistance apparatus comprising: a housing with a filter recess for receipt of the filter module as outlined above; and a handle that is connected to the housing to be movable between a storage position and a carrying position, the handle comprising an aperture to accommodate the gas port of the filter module when the filter module is received in the filter recess and the handle is in the storage position.

In some configurations, the handle comprises a side member with a connecting feature at one end that movably connects the handle to the housing, and wherein a transverse carrying portion that can be used to carry the breathing assistance apparatus extends from the other end of the side member, wherein the aperture is provided in the side member and is positioned closer to the transverse carrying portion than it is to the connecting feature.

In some configurations, an upper wall portion of the housing comprises a handle recess to receive the handle in the storage position.

Additionally, in accordance with certain features, aspects and advantages of at least one of the embodiments disclosed herein, a breathing assistance apparatus is disclosed, the breathing assistance apparatus comprising: a housing; and a shroud configured to cooperate with the housing; wherein the shroud is configured to attach to the housing by an initial movement of the shroud in a first direction followed by a subsequent movement of the shroud in a second direction that is offset from the first direction.

In some configurations, the second direction is transverse to the first direction.

In some configurations, the first direction is a downward direction and the second direction is a rearward direction.

In some configurations, the housing has upstanding vertical protrusions that engage with complementary downward open recesses in the shroud as the shroud is moved in the downward direction relative to the housing.

In some configurations, the housing has forwardly directed protrusions that engage with complementary rearwardly open recesses in the shroud as the shroud is moved in the rearward direction relative to the housing.

In some configurations, the shroud comprises a forward wall that is complementary to a surface of the housing, wherein the forward wall is configured to contact the surface of the housing when the shroud is attached to the housing.

In some configurations, the forward wall and the surface of the housing are arcuate.

In some configurations, the shroud and the housing have features to inhibit removal of the shroud from the housing.

In some configurations, the shroud comprises one or more engagement protrusions and/or engagement recesses to engage with one or more complementary engagement protrusions and/or engagement recesses of the housing.

In some configurations, the engagement protrusions and/or engagement recesses each have a first side with a relatively flat angle and a second side with a relatively steep angle, wherein the first sides are configured to interact with each other when attaching the shroud to the housing, and wherein the second sides are configured to interact with each other to inhibit removal of the shroud from the housing.

In some configurations, the breathing assistance apparatus further comprises a removable component comprising a gas port that can be removably connected to the housing, wherein the shroud is configured to cooperate with the removable component.

In some configurations, the removable component is removable from the shroud and the housing when the shroud is attached to the housing.

In some configurations, the breathing assistance apparatus comprises an electrical component in the housing that comprises a socket, wherein the removable component comprises an electrical connector for receipt in the socket and a seal that is configured to engage against a portion of the socket.

In some configurations, the seal comprises a wiper seal.

In some configurations, the seal comprises one or more sealing elements.

In some configurations, the seal comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal and that covers a part of the PCB electrical connector that is housed in the cavity.

In some configurations, the removable component is a removable elbow.

Additionally, in accordance with certain features, aspects and advantages of at least one of the embodiments disclosed herein, a breathing assistance apparatus is disclosed, the breathing assistance apparatus comprising: a housing; a removable component comprising a gas port that can be removably connected to the housing by moving the removable component in a first direction, and that can be disconnected from the housing by moving the removable component in a direction that is opposite to the first direction; and a shroud configured to cooperate with the housing and the removable component; wherein the shroud is configured to attach to the housing without the use of fasteners and by an initial movement of the shroud in a first direction followed by a subsequent movement of the shroud in a second direction that is offset from the first direction, and wherein the shroud is configured so that the shroud cannot be detached from the housing solely by pulling the removable component in the second direction.

In some configurations, the housing has upstanding vertical protrusions that engage with complementary downward open recesses in the shroud as the shroud is moved in the first direction relative to the housing.

In some configurations, the housing has forwardly directed protrusions that engage with complementary rearwardly open recesses in the shroud as the shroud is moved in the second direction relative to the housing.

In some configurations, the shroud and the housing have features to inhibit removal of the shroud from the housing.

In some configurations, the shroud comprises one or more engagement protrusions and/or engagement recesses to engage with one or more complementary engagement protrusions and/or engagement recesses of the housing.

In some configurations, the engagement protrusions and/or engagement recesses each have a first side with a relatively flat angle and a second side with a relatively steep angle, wherein the first sides are configured to interact with each other when attaching the shroud to the housing, and wherein the second sides are configured to interact with each other to inhibit removal of the shroud from the housing.

In some configurations, the first direction of movement of the shroud differs from the first and second direction of movement of the removable component.

In some configurations, the breathing assistance apparatus comprises an electrical component in the housing that comprises a socket, wherein the removable component comprises an electrical connector for receipt in the socket and a seal that is configured to engage against a portion of the socket.

In some configurations, the seal comprises a wiper seal.

In some configurations, the seal comprises one or more sealing elements.

In some configurations, the seal comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal and that covers a part of the PCB electrical connector that is housed in the cavity.

Additionally, in accordance with certain features, aspects and advantages of at least one of the embodiments disclosed herein, a breathing assistance apparatus is disclosed, the breathing assistance apparatus comprising: a housing with an electrical component in the housing; a removable component that is configured to be removably connected to the housing to form an electrical connection with the electrical component in the housing, the removable component comprising a first gas port for coupling to a first accessory for the breathing assistance apparatus and a second gas port for coupling to a second accessory for the breathing assistance apparatus, wherein the first gas port is in fluid communication with the second gas port via a gas flow path in the removable component; wherein the removable component is configured to connect to the housing by moving the removable component in a first direction relative to the housing, wherein the removable component is configured to disconnect from the housing by moving the removable component in a second direction that is opposite to the first direction, and wherein the removable component is configured to inhibit movement of the removable component in the second direction in the absence of actuating part of the removable component relative to another part of the removable component.

In some configurations, the first port comprises a gas inlet port, and the second port comprises a patient outlet port.

In some configurations, the housing comprises a recess for receipt of a liquid chamber that has a gas outlet port for connecting to the gas inlet port of the removable component, and wherein the patient outlet port is configured to connect with a patient conduit.

In some configurations, the breathing assistance apparatus is configured such that the connections between the removable component and each of the liquid chamber, the housing, and the patient conduit can be made in any order.

In some configurations, a movement direction for connecting the liquid chamber to the removable component is the same as a movement direction for connecting the removable component to the housing.

In some configurations, the removable component and the housing comprise complementary engagement features configured such that the removable component cannot disconnect from the housing in the absence of actuating said part of the removable component.

In some configurations, the removable component and the housing comprise complementary engagement features configured such that the removable component can disconnect from the housing in the absence of actuating said part of the removable component, if sufficiently high force is applied to the removable component.

In some configurations, the removable component comprises a tab with a terminal end portion that can be flexed relative to the rest of the removable component, and wherein the engagement feature(s) on the removable component is/are provided on the terminal end portion.

In some configurations, the tab comprises a thinned portion between the terminal end portion and the second gas port.

In some configurations, the first gas port and the second gas port comprise seals.

In some configurations, the seal of the first gas port comprises two wiper seal elements.

In some configurations, the two wiper seal elements are incorporated into a single seal.

In some configurations, the electrical component in the housing comprises an electrical interconnecting assembly.

In some configurations, the electrical interconnecting assembly comprises a socket for receipt of an electrical connector of the removable component, and a printed circuit board (PCB) for connecting to a power board of the apparatus.

In some configurations, a portion of the socket is configured to form a tight or close fit with the electrical connector of the removable component.

In some configurations, the removable component comprises a seal that is configured to engage against a portion of the socket.

In some configurations, the seal comprises a wiper seal.

In some configurations, the seal comprises one or more sealing elements.

In some configurations, the seal comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal and that covers a part of the PCB electrical connector that is housed in the cavity.

In some configurations, the electrical interconnecting assembly comprises an overmould to provide a pneumatic seal.

In some configurations, the overmould covers at least a section of the PCB.

In some configurations, the overmould is configured to create a seal between an aperture in the housing and the PCB.

In some configurations, the overmould covers a connection between the PCB and the socket.

In some configurations, the removable component is a removable elbow.

In some configurations, the portion of the removable component that is configured to form an electrical connection with the electrical component in the housing is pneumatically isolated from the gas flow path of the removable component, and wherein connecting the removable component to the housing does not form a direct pneumatic connection between the gas flow path and the housing.

Additionally, in accordance with certain features, aspects and advantages of at least one of the embodiments disclosed herein, a breathing assistance apparatus is disclosed, the breathing assistance apparatus comprising: a housing comprising an engagement feature; an electrical component in the housing, the electrical component comprising a receptacle; a removable component comprising an electrical connector that is configured to be a close or tight fit in the receptacle of the electrical component to assist with holding the removable component in connection with the electrical component, the removable component comprising a gas port, wherein the removable component further comprises a tab with a terminal end portion that can be flexed relative to the rest of the removable component, wherein an engagement feature is provided on the terminal end portion of the tab and is configured to engage with the engagement feature of the housing such that the removable component is inhibited from disconnecting from the housing in the absence of actuating the terminal end portion of the removable component to flex the tab.

In some configurations, the tab comprises a thinned portion adjacent the terminal end portion.

In some configurations, the engagement feature of the removable component comprises a protrusion, and wherein the engagement feature of the housing comprises a complementary engagement recess.

In some configurations, the protrusion extends outwardly from a side of the terminal end portion.

In some configurations, the housing and removable component each have two of said engagement features, wherein the engagement features of the removable component comprise two protrusions extending outwardly from opposite sides of the terminal end portion, and wherein the housing comprises two complementary engagement recesses.

In some configurations, the engagement features are configured such that inserting the removable component into the housing will cause the terminal end of the tab to flex.

In some configurations, the electrical component comprises a socket, and the removable component comprises a seal that is configured to engage against a portion of the socket.

In some configurations, the seal comprises a wiper seal.

In some configurations, the seal comprises one or more sealing elements.

In some configurations, the seal comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal and that covers a part of the PCB electrical connector that is housed in the cavity.

In some configurations, the removable component is a removable elbow.

Additionally, in accordance with certain features, aspects and advantages of at least one of the embodiments disclosed herein, an electrical component for use in a breathing assistance apparatus is disclosed, the electrical component comprising: a printed circuit board (PCB) and an overmould over at least a section of the PCB to provide a pneumatic seal over the section of the PCB and between the overmould and another component.

In some configurations, a section of the PCB is exposed from the overmould.

In some configurations, the section of the PCB that is exposed from the overmould is a lower power section of the PCB, and wherein a higher power section of the PCB is substantially covered by the overmould.

In some configurations, another portion of the PCB is exposed from the overmould to form a connector to couple the higher power section of the PCB to a main power board of the apparatus.

In some configurations, the overmould is configured to create a pneumatic seal between an aperture in a housing of the apparatus and the PCB.

In some configurations, the lower power section of the PCB that is exposed from the overmould leads to an electrical connector.

In some configurations, said electrical connector is associated with another component having a lower power requirement than the main power board.

In some configurations, said another component is a display of the apparatus.

In some configurations, the electrical component comprises a socket for receipt of an electrical connector of a removable component.

In some configurations, the overmould covers a connection between the PCB and the socket.

In some configurations, the overmould encapsulates electrical and/or electronics elements on the PCB.

Additionally, in accordance with certain features, aspects and advantages of at least one of the embodiments disclosed herein, a breathing assistance apparatus is disclosed, the breathing assistance apparatus comprising: a housing with a wall; a component in the housing, the component having a flexible printed circuit board (PCB) to provide power and/or communication to the component; and retaining features on a surface of the wall, the retaining features comprising spaced apart ribs and inwardly facing protrusions extending from terminal edges of the ribs, wherein a distance between the ribs is complementary with a width of the flexible PCB, and wherein a distance between the protrusions is smaller than the width of the flexible PCB, so that the flexible PCB is retained between the protrusions and the wall.

In some configurations, the breathing assistance apparatus further comprises one or more supports between the ribs, the support(s) having a depth smaller than a depth of the ribs, configured so that the flexible PCB contacts the protrusions.

In some configurations, the breathing assistance apparatus further comprises another component in the housing, said another component having wires to provide power and/or communication to said another component, and wherein the wires are received between the wall, one of the supports, one of the ribs, and the flexible PCB, or wherein the wires is/are received between the wall, two of the supports, and the flexible PCB.

In some configurations, the wall comprises a gap to allow the flexible PCB, and optionally wires, to pass through the wall, wherein the retaining features are positioned above the gap.

In some configurations, the breathing assistance apparatus comprises a power panel above the retaining features, wherein the power panel comprises a slot for receipt of the flexible PCB and optionally for wires.

In some configurations, the power panel further comprises a receptacle containing electrical connector(s) for the flexible PCB and optionally for wires.

Additionally, in accordance with certain features, aspects and advantages of at least one of the embodiments disclosed herein, a breathing assistance apparatus is disclosed, the breathing assistance apparatus comprising: a housing with a gas port that is configured to couple with a port of a liquid chamber; and a seal on the gas port to provide a pneumatic seal with the port of the liquid chamber, wherein the seal is a single seal comprising two sealing elements, wherein each sealing element comprises a wiper seal.

In some configurations, each sealing element comprises a bulbous radially outwardly located tip, and optionally wherein each sealing element comprises a narrowed web section between the tip and a base of seal.

In some configurations, the sealing elements are annular sealing elements, wherein one of the sealing elements is located closer to a terminal end of the gas port than the other one of the sealing elements, and wherein the one of the sealing elements that is located closer to the terminal end of the gas port has a larger diameter than the other one of the sealing elements.

In some configurations, the seal comprises a further sealing element at or adjacent an opposite end of the seal from a terminal end of the gas port.

In some configurations, the further sealing element comprises an outward taper and a radially projecting flange at or adjacent an opposite end of the seal from a terminal end of the gas port.

In some configurations, the further sealing element is configured to form a seal with a second component that differs from the liquid chamber.

In some configurations, the flange projects radially further outwardly than the wiper seals, so that the flange is configured to connect with a second component having a larger internal diameter than the port of the liquid chamber.

In some configurations, the flange is configured to connect with a component of a disinfection kit.

In some configurations, the port of the liquid chamber comprises an inlet port or an outlet port.

In some configurations, the gas port comprises a recessed portion for receipt of the seal.

In some configurations, the housing comprises two gas ports, and wherein one of the seals is provided on each of the gas ports.

In some configurations, the gas port is part of a removable component, the breathing assistance apparatus comprises an electrical component in the housing that comprises a socket, and the removable component comprises an electrical connector for receipt in the socket and a seal that is configured to engage against a portion of the socket.

In some configurations, the seal that is configured to engage against the portion of the socket comprises a wiper seal.

In some configurations, the seal that is configured to engage against the portion of the socket comprises one or more sealing elements.

In some configurations, the seal that is configured to engage against the portion of the socket comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal that is configured to engage against the portion of the socket and that covers a part of the PCB electrical connector that is housed in the cavity.

Additionally, in accordance with certain features, aspects and advantages of at least one of the embodiments disclosed herein, a removable component for use with a breathing assistance apparatus that comprises a housing and an electrical component in the housing that comprises a socket is disclosed, wherein the removable component is configured to be removably connected to the housing to form an electrical connection with the electrical component in the housing, the removable component comprising: an electrical connector for receipt in the socket, a gas port, and a seal that is configured to engage against a portion of the socket.

In some configurations, the seal comprises a wiper seal.

In some configurations, the seal comprises one or more sealing elements.

In some configurations, the seal comprises an overmoulded seal.

In some configurations, the electrical connector comprises a printed circuit board (PCB) electrical connector, the PCB electrical connector is partly housed in a cavity of the removable component, and the removable component comprises a moulded base member that is integrally moulded with the seal that is configured to engage against the portion of the socket and that covers a part of the PCB electrical connector that is housed in the cavity.

In some configurations, the gas port is a first gas port, and the removable component comprises a second gas port that is in fluid communication with the first gas port via a gas flow path in the removable component.

In some configurations, the first gas port is for coupling to a first accessory for the breathing assistance apparatus, and wherein the second gas port is for coupling to a second accessory of the breathing assistance apparatus.

In some configurations, the removable component is a removable elbow.

Additionally, in accordance with certain features, aspects and advantages of at least one of the embodiments disclosed herein, the combination of a breathing assistance apparatus and a removable component is disclosed, the combination comprising: a breathing assistance apparatus that comprises a housing and an electrical component in the housing that comprises a socket; and the removable component as outlined above.

In some configurations, the electrical component comprises an electrical interconnecting assembly.

In some configurations, the electrical interconnecting assembly comprises the socket and a printed circuit board (PCB) for connecting to a power board of the apparatus.

In some configurations, the electrical interconnecting assembly comprises an overmould to provide a pneumatic seal.

Additionally, in accordance with certain features, aspects and advantages of at least one of the embodiments disclosed herein, a seal for use in a motor module for a breathing apparatus is disclosed, the seal comprising a fixed portion and a flexible portion configured to bend inwardly towards a gas flow path.

In some configurations, the seal has an operative position or orientation in which the flexible portion is flexed to contact a portion of the fixed portion. In the operative orientation, the seal forms a tortuous path for any gases to travel through.

Additionally, in accordance with certain features, aspects and advantages of at least one of the embodiments disclosed herein, a motor module for a breathing apparatus is disclosed, the motor module comprising a base, a cover layer, a sensing layer sandwiched between the base and the cover layer, and a seal between the base and the sensing layer and/or a seal between the sensing layer and the cover layer, the or each seal comprising a fixed portion and a flexible portion configured to bend inwardly towards a gas flow path.

In some configurations, the seal comprises an undulating shape.

In some configurations, the seal reduces in height to an operative position from an uncompressed position.

Features from one or more embodiments or configurations may be combined with features of one or more other embodiments or configurations. Additionally, more than one embodiment may be used together during a process of respiratory support of a patient.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
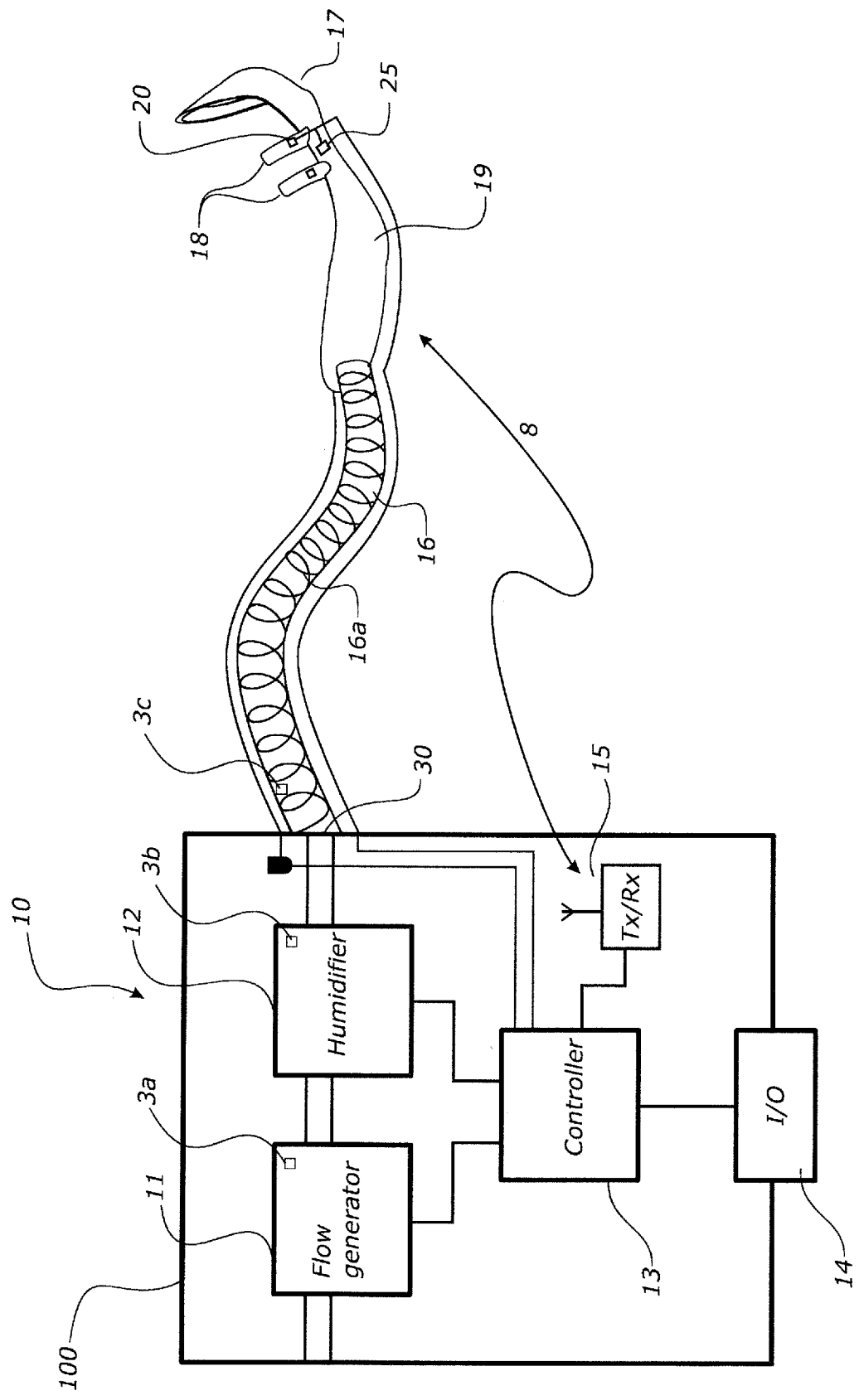
FIG. 1 shows in diagrammatic form a breathing assistance apparatus.

A breathing assistance apparatus 10 for delivering a flow of gas (which may contain one or more gases) to a patient is shown in FIG. 1. The apparatus 10 could, for example, be a CPAP apparatus or a high flow apparatus. An exemplary CPAP apparatus is described in WO 2011/056080. The contents of that specification are incorporated herein in their entirety by way of reference.

A CPAP apparatus is a gases supply and optionally gases humidification apparatus. The apparatus is operable to provide respiratory assistance to patients or users who require a supply of gas (humidified or otherwise) at positive pressure for the treatment of diseases such as Obstructive Sleep Apnea (OSA), snoring, or Chronic Obstructive Pulmonary Disease (COPD) and the like. A CPAP apparatus would typically include a humidifier liquid chamber, so as to form a combined assisted breathing unit and humidifier.

CPAP apparatuses, when used with a humidifier, typically have a structure where gases at a required pressure are delivered from an assisted breathing unit or blower unit to a liquid chamber downstream from the blower. As the gases pass through the liquid chamber, they become saturated with liquid vapour (e.g. water vapour). A flexible tubular gases conduit delivers the gases to a user or patient downstream from the humidifier chamber.

A high flow apparatus may be used to deliver a high gas flow or high flow therapy to a patient to assist with breathing and/or treat breathing disorders including chronic obstructive pulmonary disease (COPD). A high flow apparatus includes a gases supply and typically includes a humidification apparatus.

The breathing assistance apparatuses typically have one or more accessories such as a breathing conduit and a patient interface such as a cannula or mask for delivering gases to a patient. The conduit enables gases to be delivered from the housing of the breathing assistance apparatus to the patient. For example, the apparatus may be placed on a floor or other support surface, and the patient may be in a bed. The breathing assistance apparatus may have a recess for receipt of a humidifier liquid chamber. The liquid chamber will receive liquid from, for example, a flexible liquid bag that delivers liquid to a humidifier liquid chamber via one or more tubes. Alternatively, the liquid chamber can be removed and refilled as required. The recess will contain a heater plate to heat the liquid chamber, to humidify gases passing through the liquid chamber. The humidified gases are then delivered to the patient.

In general terms, the apparatus 10 comprises a main housing 100 that contains a flow generator 11 in the form of a motor/impeller arrangement, a humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gas flow) for delivery to a patient, operating the humidifier 12 to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is connected to a gas flow output or patient outlet port 30 in the housing 100 of the breathing assistance apparatus 10, and is connected to a patient interface 17 such as a nasal cannula with a manifold 19 and nasal prongs 18. Additionally, or alternatively, the patient breathing conduit 16 could be connected to a face mask. Additionally, or alternatively, the patient breathing conduit could be connected to a nasal pillows mask, and/or a nasal mask, and/or a tracheostomy interface, or any other suitable type of patient interface. The gas flow, which may be humidified, that is generated by the breathing assistance apparatus 10 is delivered to the patient via the patient breathing conduit 16 through the patient interface 17. The patient breathing conduit 16 can have a heater wire 16a to heat gas flow passing through to the patient. The heater wire 16a is under the control of the controller 13. The patient breathing conduit 16 and/or patient interface 17 can be considered part of the breathing assistance apparatus 10, or alternatively peripheral to it. The breathing assistance apparatus 10, breathing conduit 16, and patient interface 17 may together form a breathing assistance system or, in some configurations, a flow therapy system.

General operation of an exemplary breathing assistance apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and/or controls the humidifier 12 to humidify the gas flow and/or heat the gas flow to an appropriate level. The gas flow is directed out through the patient breathing conduit 16 and patient interface 17 to the patient. The controller 13 can also control a heating element in the humidifier 12 and/or the heating element 16a in the patient breathing conduit 16 to humidify and/or heat the gas to a desired temperature that achieves a desired level of therapy and/or comfort for the patient. The controller 13 can be programmed with, or can determine, a suitable target temperature of the gas flow.

Operation sensors 3a, 3b, 3c, 20, and 25, such as flow, temperature, humidity, and/or pressure sensors, can be placed in various locations in the breathing assistance apparatus 10 and/or the patient breathing conduit 16 and/or patient interface 17. Output from the sensors can be received by the controller 13, to assist it to operate the breathing assistance apparatus 10 in a manner that provides optimal therapy. In some configurations, providing optimal therapy includes meeting a patient's inspiratory flow. The apparatus 10 may have a transmitter and/or receiver 15 to enable the controller 13 to receive signals 8 from the sensors and/or to control the various components of the breathing assistance apparatus 10, including but not limited to the flow generator 11, humidifier 12, and heater wire 16a, or accessories or peripherals associated with the breathing assistance apparatus 10. Additionally, or alternatively, the transmitter and/or receiver 15 may deliver data to a remote server or enable remote control of the apparatus 10.

The breathing assistance apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute (LPM) to about seventy liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

For example, in some configurations, for an adult patient 'high flow therapy' may refer to the delivery of gases to a patient at a flow rate of greater than or equal to about 10 liters per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may, in some configurations, deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory flow, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available for each and every breath, while minimising re-breathing of carbon dioxide, nitrogen, etc.

In one example for high flow therapy, an unsealed or non-sealing user interface, e.g. a nasal cannula, is used. For CPAP a sealed interface is typically used, e.g. a nasal mask, full face mask, or nasal pillows.

The patient interface 17 may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As described below, the breathing assistance apparatus 10 has various features to assist with the functioning, use, and/or configuration of the breathing assistance apparatus 10.

As shown in FIGS. 2 to 5, a first configuration breathing assistance apparatus 10 comprises a breathing assistance apparatus base unit 50 having a main housing 100. The main housing 100 has a main housing upper chassis 102 and a main housing lower chassis 104.

The main housing of the base unit 50 has a peripheral wall arrangement. The peripheral wall arrangement defines a recess 108 that provides a humidifier liquid chamber bay for receipt of a removable humidifier liquid chamber 151. The removable liquid chamber 151 contains a suitable liquid such as water for humidifying gases that will be delivered to a patient.

The base unit 50 of the apparatus 10 may have a movable finger guard 140 that guards against a user touching a base flange 155 of the liquid chamber when the liquid chamber is in place in the recess 108 and when a barrier 141a of the finger guard is in a covering position as shown in the figures. The barrier 141a is movable between the covering position and a lowered access position in which the recess 108 is less covered or is uncovered by the barrier 141a.

Figure 36:
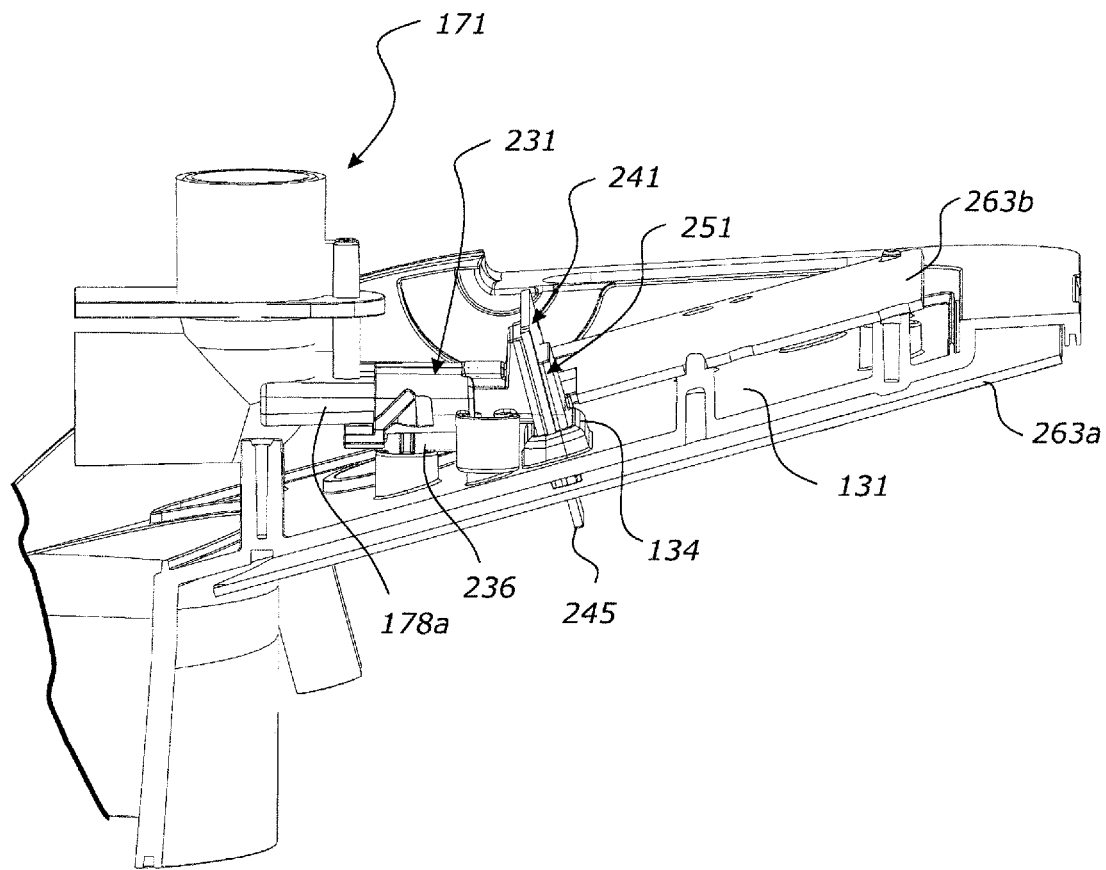
FIG. 36 is a right side overhead perspective sectional view of the breathing assistance apparatus showing the engagement of the electrical connector assembly with the main power board and the display/interface power board.
Figure 37:
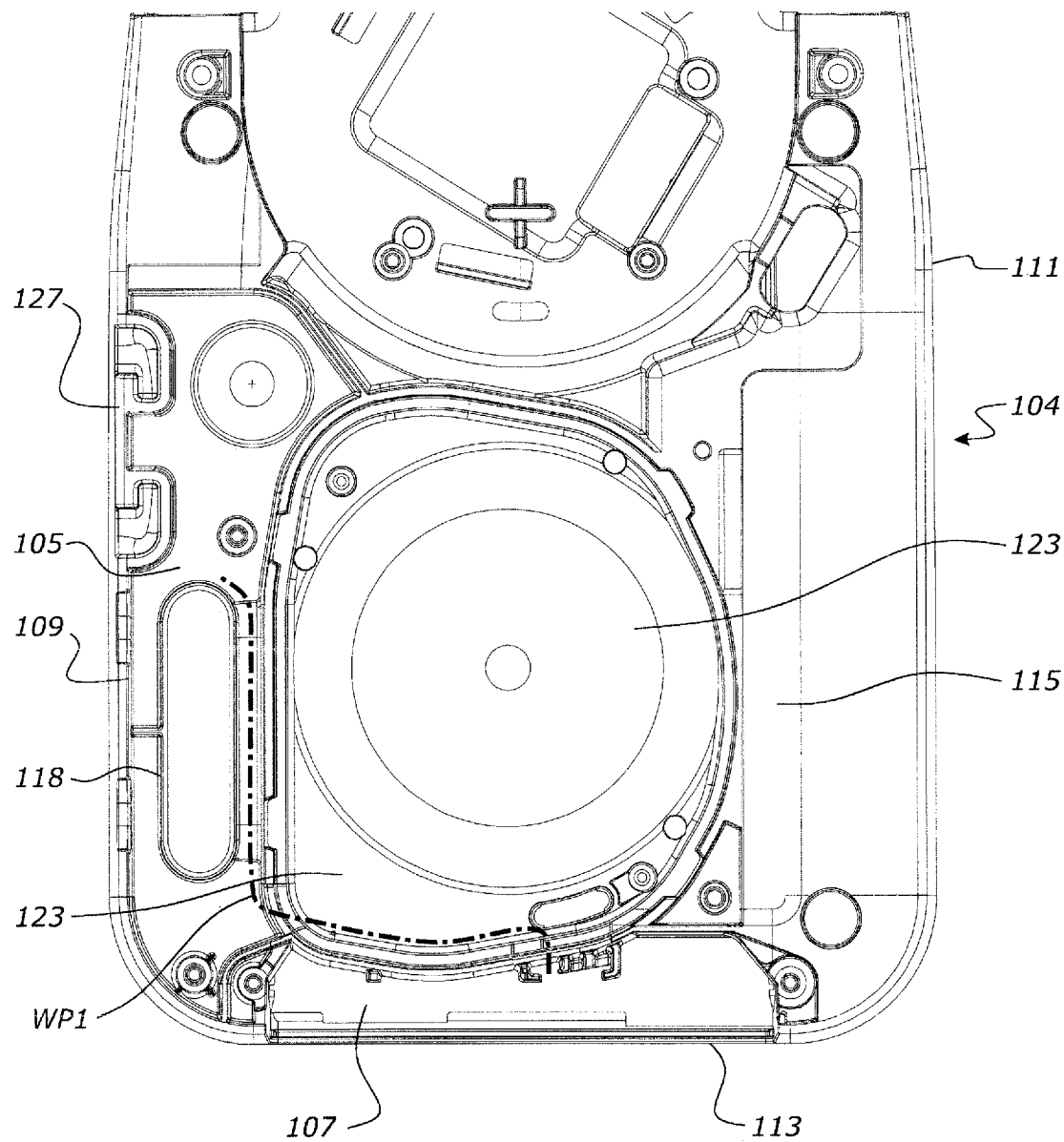
FIG. 37 is a bottom view of a rear portion of the lower chassis.

In the form shown, the main housing lower chassis 104 peripheral wall arrangement comprises a substantially vertical left side outer wall 109 that is oriented in a front-to-rear direction of the main housing 100, a substantially vertical right side outer wall 111, and a substantially vertical rear outer wall 113 (FIG. 37) that extends between and connects the walls 109, 111. As shown in FIGS. 36 and 37, a bottom wall 115 extends between and connects the lower ends of walls 109, 111, 113, and forms a base of the apparatus and a substantially horizontal floor portion of the liquid chamber bay.

The floor portion of the recess 108 has a receptacle portion 108a to receive a heater arrangement such as a heater plate 140 or other suitable heating element(s) for heating liquid in the liquid chamber 151 for use during a humidification process. The heater plate would typically have a shape that substantially corresponds to the shape of a base 154 of the liquid chamber 151, such as a circular shape for example. The heater plate 140 is resiliently mounted; for example, on biasing device(s) such as spring(s). The resilient mounting enables the heater plate to move downwardly to accommodate the liquid chamber 151 in the recess 108, while maintaining good contact between the heater plate 140 and the base of the liquid chamber once the liquid chamber is inserted in the recess 108.

The main housing lower chassis 104 is attachable to the upper chassis 102, either by suitable fasteners or integrated attachment features such as clips for example. When the main housing lower chassis 104 is attached to the main housing upper chassis 102, the walls of the upper and lower chassis engage with each other.

The lower chassis 104 has a motor recess 122 (FIG. 39) for receipt of a motor module which may be permanently inserted in the motor recess 122 or may be removable from the motor recess 122. A recess opening is provided in the bottom wall 115 adjacent a rear edge thereof, for receipt of the removable motor module. A base 123 of the motor module covers the opening into the motor recess 121. The motor module comprises a motor that forms a blower to cause gas flow, and may comprise one or more sensors to sense properties of the gas passing through the motor module. The motor module may comprise sensor(s) to sense parameters of gases flowing through the motor module.

The motor module and housing of the base unit 50 of the apparatus 10 are provided with suitable tubes and/or gas flow passages to deliver gases from one or more gases inlets of the base unit 50 of the apparatus, to a gas inlet port 157 of the liquid chamber 151 to humidify the gases. The gases are delivered from a gas outlet port 159 of the liquid chamber 151 to the patient outlet port 30 (via a humidified gas inlet port 163) and thereby to the patient via the patient breathing conduit 16 and patient interface 17.

The motor recess 122 comprises a recess opening in a bottom wall 115 of the housing. Alternatively, the recess opening could be in a different part of the housing, such as a side, front, or top of the housing.

The base unit 50 of the apparatus 10 may have a battery module 125 to provide power to the apparatus when there is a power outage or for portable use. The battery module comprises a battery cover 126 containing a battery. The battery of the battery module 125 may be replaceable.

In the form shown, the battery cover 126 of the battery module 125 is coupled to an exterior of the back wall 113 of the apparatus housing 100. This provides a large surface area to cool the battery and reduces the amount of heat entering the apparatus from the battery. Additionally, this configuration reduces the influence of heat generated by components of the apparatus on the battery, particularly when the battery is being charged. In an alternative configuration, the battery may be internally mounted in the main housing.

The housing may be provided with a battery cover 126 (FIGS. 48a, 48b) to cover the battery once installed. Alternatively, the battery may mount directly to the housing 100 without a cover. The battery, and therefore the battery cover 126, may be sized to not extend beyond the bottom wall 115 of the housing. Alternatively, the battery cover 126 may be longer and extend beyond the bottom wall 115 of the housing to accommodate a larger battery.

Figure 3:
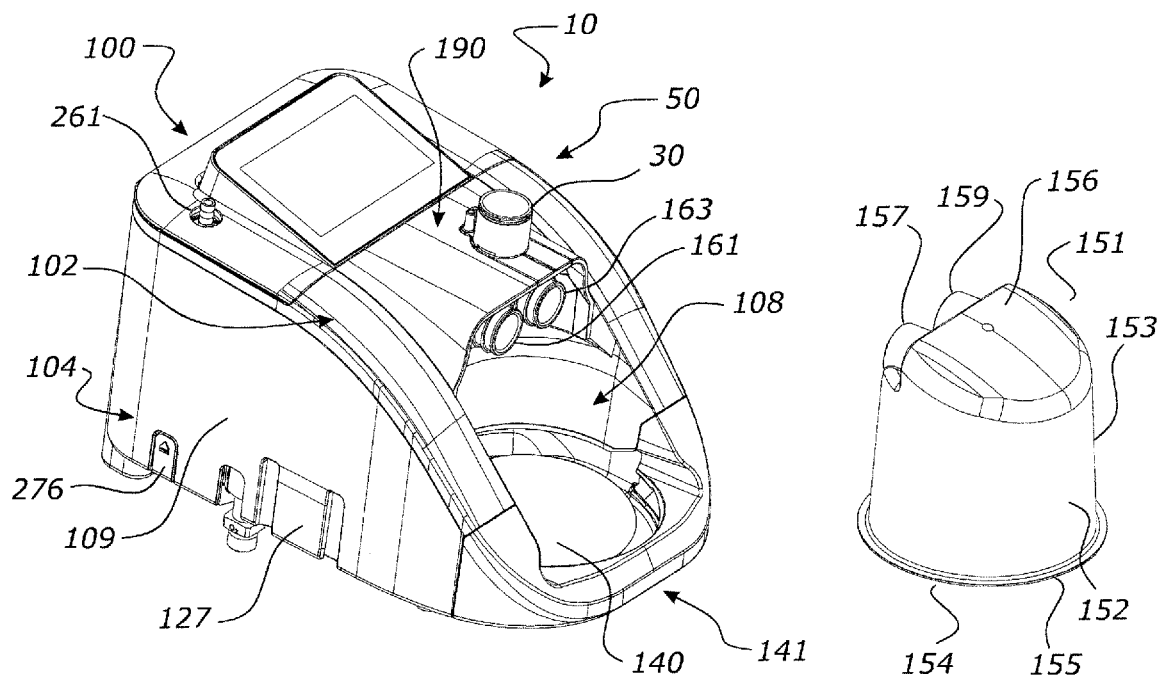
FIG. 3 is a front/left side overhead perspective view of the breathing assistance apparatus with the liquid chamber removed from the recess of the breathing assistance apparatus base unit.
Figure 4:
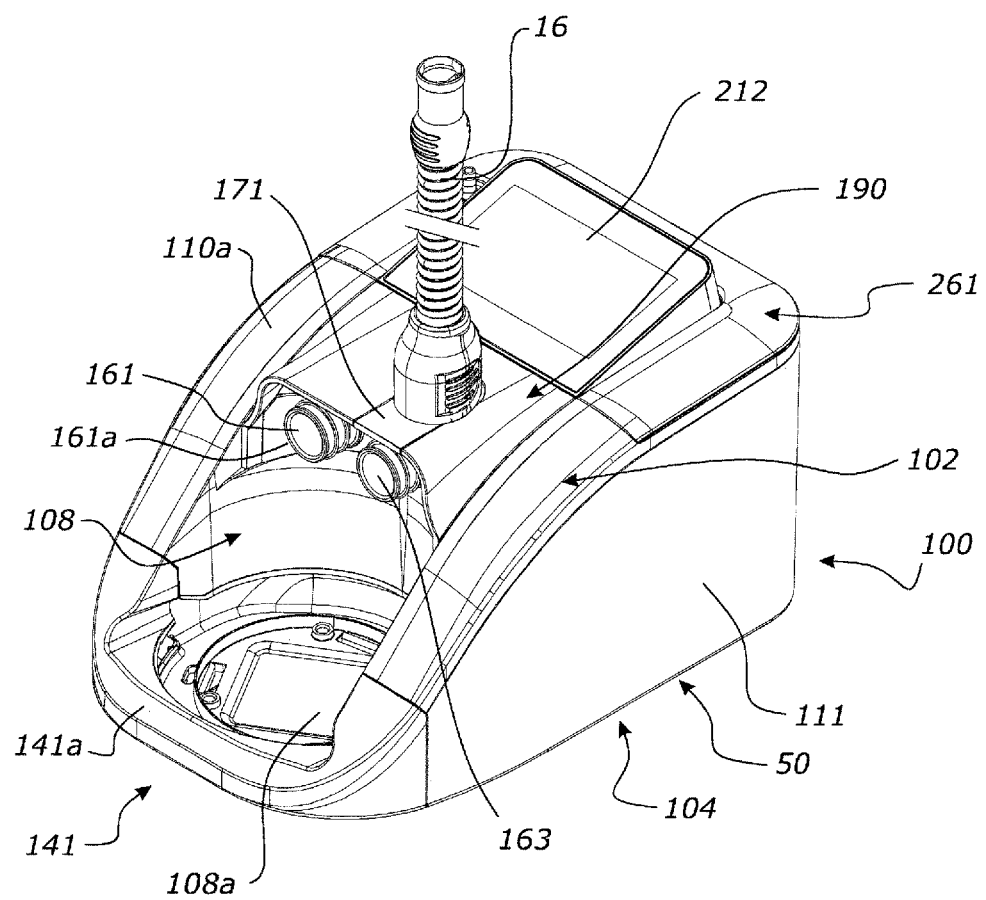
FIG. 4 is a front/right side overhead perspective view of the breathing assistance apparatus base unit with the liquid chamber and heater plate not shown.
Figure 5:
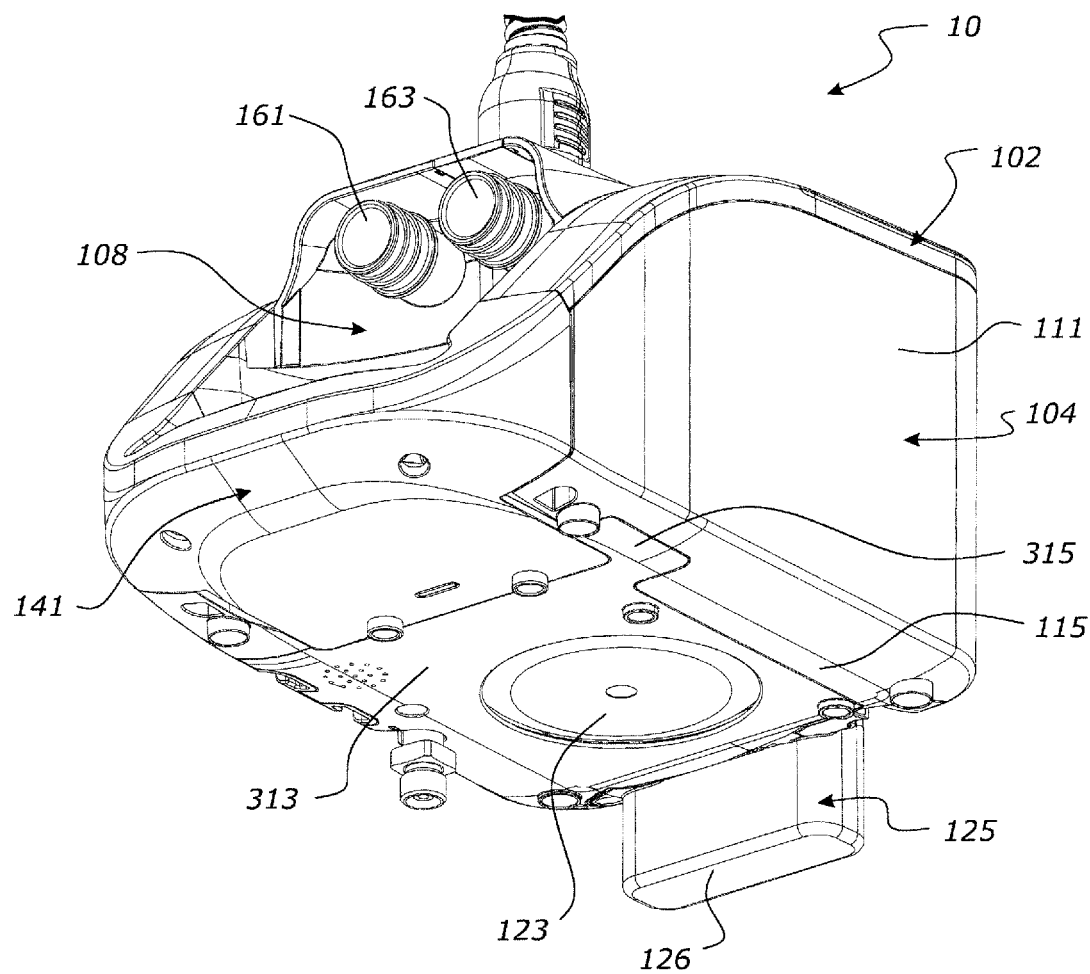
FIG. 5 is a front/right side bottom perspective view of the breathing assistance apparatus base unit with the liquid chamber not shown.

As shown in FIG. 3, the base unit 50 of the apparatus 10 has a mounting feature 127 for mounting the apparatus to a support apparatus.

The mounting feature 127 may be integrally formed with part of the main housing of the base unit 50 of the apparatus 10. In the form shown, the mounting feature 127 is integrally formed with the left side wall 109 the lower chassis 104 of the housing 100. The mounting feature 127 could instead be integrally formed with any of the other walls of the housing 100, such as a rear wall, right side wall, or other wall.

The main housing 100 of the apparatus may be formed from any suitable material that will allow the mounting feature 127 to be integrally formed. For example, the housing 100 may be formed from polycarbonate.

The integral mounting feature 127 has greater impact strength compared to an additional, screwed in part. Strengthening of the mounting feature 127 may also be done by, for example, varying the wall thickness, ribbing, or varying in internal geometries.

FIG. 3 shows a humidifier liquid chamber 151 for use with the breathing assistance apparatus 10. The chamber 151 is a removable liquid chamber to be filled with liquid such as water for the humidification of respiratory gases. The liquid chamber 151 is removable from the base unit 50 of the breathing assistance apparatus 10 to be more easily re-filled or disposed of.

The liquid chamber 151 has a body 152 having a peripheral wall 153 and a roof 156. The body defines an internal chamber for receipt of a liquid. A base 154 is provided at the lower end of the peripheral wall, and comprises a base flange 155 that projects outwardly from the lower end of the peripheral wall 153. First and second base unit connection ports comprising a liquid chamber gas inlet port 157 and a liquid chamber gas outlet port 159 are in communication with the internal chamber of the liquid chamber 151. The breathing assistance apparatus base unit 50 comprises complementary chamber connection ports comprising a gas outlet port 161 and a humidified gas inlet port 163. When the liquid chamber is received in the recess 108 to engage with the housing 100, the liquid chamber gas inlet port 157 connects to the gas outlet port 161 that receives gases from the motor module via a gasflow passage, and the liquid chamber gas outlet port 157 connects to the humidified gas inlet port 163 to deliver humidified gases from the liquid chamber to the patient outlet port 30.

The liquid chamber 151 could have a generally circular peripheral shape, or could be any other suitable shape, with the recess 108 shape modified accordingly if required.

In the form shown, the liquid chamber 151 has a substantially cylindrical shape.

The base 154 of the liquid chamber 151 is heat conductive. In particular, the base 154 of the liquid chamber 151 is made from a highly heat conductive material, which allows heating of the liquid in the chamber when in contact with the heater plate 140 of the base unit 50 of the breathing assistance apparatus 10 during use.

The liquid chamber 151 can be fluidly coupled to the base unit 50 of apparatus 10 in a rearward insertion direction CID of the liquid chamber 151 into the recess 108, from a position at the front of the housing 100 in a direction toward the rear of the housing 100. The gas outlet port 161 is in fluid communication, via a fixed L shaped elbow, with a gas flow passage from the motor/impeller unit.

The humidified gas inlet port 163 is embodied in a removable component comprising removable elbow 171 (FIGS. 6 to 13) that can be removably connected to the housing. The removable elbow 171 is L-shaped, and further comprises the upstanding patient outlet port 30 for coupling to the patient breathing conduit 16 to deliver gases to the patient interface 17. In different configurations, the removable component may not have an elbow shape, and could instead, for example, have aligned inlet and outlet ports.

The gas outlet port 161, humidified gas inlet port 163, and patient outlet port 30 each comprise soft seals such as wiper seals, L-seals, X-rings, or O-rings to provide a sealed gases passageway between the apparatus 10, the liquid chamber 151, and the patient breathing conduit 16 and optionally one or more other accessories.

The gas outlet port 161 and gas inlet port 163 comprise multiple sealing elements. The sealing elements may be wiper seals, L-seals, X-rings, or O-rings. The wiper seals may have a T-shaped cross-section. The gas outlet port 161 and the gas inlet port 163 may each comprise two, three, or more sealing elements. In one configuration, each of the gas inlet port 163 and gas outlet port 161 comprises a pair of wiper seals. In this configuration, the gas inlet port 163 has two wiper seals positioned adjacent each other on the gas inlet port 163. Similarly, the gas outlet port 161 comprises a pair of wiper seals positioned adjacent each other on the gas outlet port 161. The pair of wiper seals (or of the other types of sealing elements) on each port 161, 163 improves the seal with the corresponding base unit connection ports 157, 159 and provides improved protection against liquid ingress into the interior of the housing of the base unit 50 of the apparatus where electronics are located. When the liquid chamber 151 is coupled to the gas inlet port 163 and gas outlet port 161 of the base unit 50, one wiper seal may be positioned inside each base unit connection port 157, 159 and one wiper seal may be located outside each base unit connection port 157, 159, when the liquid chamber is assembled with the base unit 50. Alternatively, both wiper seals are positioned inside the respective base unit connection ports 157, 159 when the liquid chamber 151 is assembled onto the heater plate 140 in the recess 108. The arrangement of using two wiper seals per port 161, 163 provides redundancy for liquid ingress. Similar arrangement can be used for L-seals, X-rings, or O-rings. The gas outlet port 161 and gas inlet port 163 of the base unit 50 are structured to have an elongate portion; i.e., a length of the ports 161, 163 is such that the wiper seals, L-seals, X-rings, or O-rings are retained on the ports 161, 163.

The gas inlet port 157 of the liquid chamber is complementary with the gas outlet port 161 of the breathing assistance apparatus base unit 50, and the gas outlet port 159 of the liquid chamber is complementary with the humidified gas inlet port 163 of the breathing assistance apparatus base unit 50. The axes of those ports may be parallel and/or horizontal enable the liquid chamber 151 to be inserted into the recess 108 in a substantially linear movement to form gas connections between the ports.

The chamber connection ports 161, 163 are parallel cylindrical features extending from the housing of the breathing assistance apparatus base unit 50. The ports 161, 163 will typically have an equal profile, and equal length, and axes located on the same horizontal plane. The ports 161, 163 will typically terminate on the same vertical plane at their distal ends. The ports 161, 163 have a port separation distance or pitch, which is the horizontal distance between the centre or axis of each port 161, 163. This is substantially equal to the horizontal distance between the centres of the base unit connection ports 157, 159 of the liquid chamber.

The chamber connection ports 161, 163 (which in the form shown are male connection members) of the breathing assistance apparatus base unit 50 insert into the base unit connection ports 157, 159 (which in the form shown are female connection members) of the liquid chamber in a concentric manner. The inner diameter of the base unit connection ports 157, 159 is larger than the outer diameter of the chamber connection ports 161, 163.

The liquid chamber 151 may initially be inserted into the recess 108 on an angle, and then tilted to be substantially horizontal, so that a rear part of movement of the liquid chamber 151 is substantially linear. The recess 108 may comprise one or more guide rails to assist with holding the liquid chamber in position in the recess 108.

The breathing assistance apparatus 10 may have any one or more of the features and/or functionality of the breathing assistance apparatus described and shown in WO2016/207838A9 (WO'838). The contents of that specification are incorporated herein in their entirety by way of reference.

In order to prevent gas leaking from either of the two connections (port 157 to port 161, and port 159 to port 163), one or more sealing elements are provided for each connection. The one or more sealing elements may be on the outer surface of male ports, and seal against the inner surface of female ports. In one configuration, the gas inlet port 157 of the liquid chamber and the gas outlet port 159 of the liquid chamber are the female ports, and the housing ports, i.e. the gas outlet port 161 and the humidified gas inlet port 163 are the male ports. Alternatively, the ports 157, 159 of the liquid chamber may be the male ports and the ports 161, 163 of the breathing assistance apparatus base unit 50 may be the female ports.

FIGS. 6 to 12 show details of the removable elbow 171. Although this section describes the features of the humidified gas inlet port 163 and its interaction with the gas outlet port 159 of the liquid chamber, including a seal 173, the features of the gas outlet port 161 of the housing and its interaction with the gas inlet port 157 of the liquid chamber will be the same.

The humidified gas inlet port 163 comprises a generally horizontally oriented extended portion 162 that is configured to insert within the gas outlet port 159 of the liquid chamber. The terminal end 163a of the port has a rounded edge to aid in aligning the gas outlet port 159 with the humidified gas inlet port 163. Additionally, the terminal end 163a is slightly smaller in diameter than the gas outlet port 159.

At least one recessed portion 163b is provided on the port 163. This recessed portion allows a seal 173 to be attached to the port. The seal 173 can be attached by being overmoulded directly onto the port 163. Alternatively, the seal 173 can be stretched over the terminal end 163a of the port in order to place it in the recess 163b. The seal may be shaped so that it remains in a stretched state once it has been placed in the recess, to assist with maintaining the seal in position. Once the seal 173 is located in the recess 163b, the boundaries of the recess 163b prevent any movement of the seal 173 along the port 163. This allows the liquid chamber 151 to be connected/disconnected in a lateral motion without dislodging the seal 173 from the port 163.

The humidified gas inlet port 163 may comprise a plurality of seals or sealing elements located in the recess 163b. The plurality of seals 175 may be a pair of wiper seals, L-seals, X-rings, or O-rings. The wiper seals may have a T-shaped cross-section. In some configurations, the gas inlet port 163 may comprise three or more seals or sealing elements. A similar seal arrangement can also be on the outlet port 161 of the base unit 50. The wiper seals, i.e. double seals, prevent or reduce breathing gas leak and/or condensate from moving towards the electronics in the removable elbow 171 and the electrical connector 178 (described below) of the elbow. Similarly, the seals reduce the chance of, and preferably prevent, liquid, i.e. condensate, from moving and dripping back into the gas outlet port 161 of the base unit 50 to prevent water ingress into the electronics chamber of the base unit.

The seal 173 may be made from silicone rubber. In an alternative configuration, the seal 173 could be made from any suitable elastomer, such as polyurethane. Alternatively, the seal 173 may be made from thermoplastic elastomer(s) and/or thermoplastic vulcanisate(s), particularly if the seal will be overmoulded onto the removable elbow.

As discussed above, a plurality of sealing elements may be provided on the port 163 in order to seal against the port 159 of the liquid chamber at a plurality of locations. The plurality of sealing elements could be achieved by having a plurality of seals 173, with the port 163 having a corresponding plurality of recesses 163b to accommodate each seal. Alternatively, in the configuration shown, the plurality of sealing elements 175 are incorporated into a single seal 173 that is located in a single recess 163b.

Having a plurality of sealing elements 175 on a single seal 173 is preferable to having a plurality of seals on the port 163, as it reduces the number of seals that need to be attached during manufacturing. Additionally, the increased width of the seal when providing a plurality of sealing elements 175 reduces the chance of the seal turning inside out during assembly onto the port 163.

Having a plurality of sealing elements 175 is beneficial in providing redundancy in the seal between the breathing assistance apparatus base unit 50 and the liquid chamber 151. This reduces the chance of a breathing gas leak and/or liquid moving into the base unit 50 occurring as it would require the seals provided by each of the sealing elements 175 to fail. Additionally, having one sealing element 175, i.e. a forward sealing element, closer to the terminal end 163a of the port 163 (compared to a single centrally-located sealing element) allows a seal to be formed between the liquid chamber 151 and the breathing assistance apparatus 10 even if the liquid chamber is not fully connected onto the port 163. Having a plurality of sealing elements 175 also helps to align the liquid chamber 151 in the recess 108 and align the ports 159, 163, by providing multiple points of contact between the ports 159, 163. The rearmost sealing element 175 on the port 163 limits the position of the liquid chamber 151 more than the forward sealing element on the port. That is because the rearmost sealing element is further from the centre of the liquid chamber 151, so tolerance between that sealing element and the liquid chamber port 159, 163 equates to a smaller available amount of angular rotation of the liquid chamber 151.

When a plurality of sealing elements is provided, the sealing elements may be spaced equally apart with respect to each other along the base 173a. In other configurations, the distance between the sealing elements may not be equal.

In some configurations, the distance between the sealing elements is equal to the distance between the forward sealing element and the terminal end 163a of the gas inlet port 163. In other configurations, the distance between the sealing elements may not be equal to the distance between the forward sealing element 175 and the terminal end 163a.

The forward sealing element is the primary sealing element, and the rearmost sealing element is the secondary sealing element. The sealing elements create an effective outer diameter of the ports 161, 163 of the base unit 50 which is slightly larger than the inner diameter of the ports 157, 159 of the liquid chamber, prior to connection.

The elastomeric nature of the seals allows for connection between the rigid bodies of the ports 157, 159, 161, 163. Having multiple sealing elements 175 allows for a pneumatic seal between the base unit 50 of the breathing assistance apparatus 10 and the humidifier liquid chamber 151, even if one seal fails.

The degree to which a successful seal is created is dependent on the depth of the base unit connection port 157, 159 of the liquid chamber into which the corresponding chamber connection port 161, 163 of the breathing assistance apparatus base unit 50 locates so that one or more seal elements 175 are engaged. This assumes the diameter of the chamber connection ports 161, 163, base unit connection ports 157, 159, and seals 175 are of appropriate dimensions to allow one or more seals to engage. Advantageously, both seals 175 are engaged to minimise any possible rotation or rocking of the liquid chamber 151, by constraining an additional degree of freedom, during use as well as to provide the pneumatic seal. Engaging both seals 175 also provides redundancy if a singular seal were to fail.

It should be understood that while a complete seal between the base unit connection ports 157, 159 of the liquid chamber and the chamber connection ports 161, 163 of the breathing assistance apparatus base unit 50, some leakage may be accommodated between those components while still providing sufficient gas flow to a user.

One or more of the sealing elements 175 may be a wiper seal. In the form shown in FIGS. 7 and 11, the wiper seal is a flexible annular rim that runs around the circumference of the port 163. As shown in the cross-section in FIG. 12, the wiper seal has a bulbous radially outwardly located tip 175a which may have a circular cross-section for example. The tip 175a is configured to contact the inner surface of the base unit connection port 159 of the liquid chamber. The wiper seal may advantageously have a narrowed web section 175b leading from the base of the seal to the tip 175a. The narrowed web section 175b allows the wiper seal to flex more easily, while the enlarged bulbous tip 175a provides a larger surface area for the sealing contact with the inner surface of the base unit connection port 159 of the liquid chamber. In some configurations, the wiper seal may not have the bulbous tip 175a.

Figure 12:
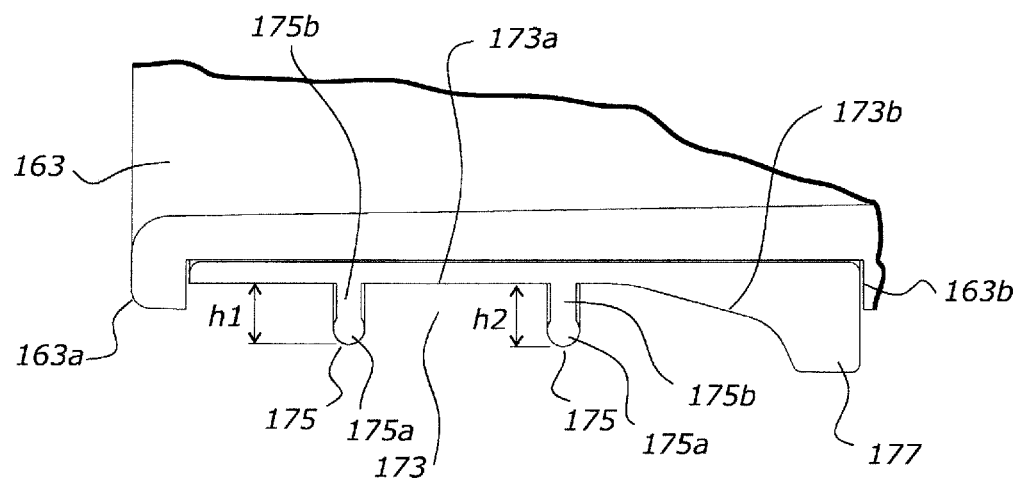
FIG. 12 is a right side view of part of the elbow showing details of the seals.

Referring to FIG. 12, the radial height h1, h2 of each wiper seal is such that in an unflexed position, the diameter of the wiper seal is greater than the inner diameter of the base unit connection port 159 of the liquid chamber. When the liquid chamber 151 is inserted into the recess 108, the wiper seal will contact the inner wall of the base unit connection port 159 of the liquid chamber and will flex downwards towards the base 173a of the seal 173 to accommodate the smaller inner diameter of the base unit connection port 159 of the liquid chamber. The elasticity of the seal will mean that the wiper seal 175 resists this flexing, thereby providing a sealing force between the points of contact on the base unit connection port 159 of the liquid chamber and the tip 175a of the wiper seal. This configuration accommodates slight variations in sizes of both the wiper seals 175 and the port 159 of the liquid chamber due to manufacturing tolerances, as the wiper seals would flex to accommodate the exact diameter of the liquid chamber port.

Another advantage of the wiper seals 175 is the low resistance they provide to axial movement. Unlike other seals, the wiper seals' ability to flex and conform to the inner surface of the base unit connection port of the liquid chamber results in a low amount of friction, thereby making it easier to connect and disconnect the liquid chamber 151 from the housing 100 of the base unit 50 of the breathing assistance apparatus 10.

A wiper seal 175 does, however, provide slightly more resistance movement of liquid chamber 151 in one scenario. When the liquid chamber is being moved in a first direction (e.g. towards the housing 100 in an insertion direction CID when being connected), the wiper seal 175 will be flexed in a first orientation. When the liquid chamber is being moved in a second direction (e.g. away from the housing 100 in a removal direction CRD when being disconnected), the wiper seal 175 will be flexed in a second orientation. Therefore, when the liquid chamber 151 first moves in one direction after moving in the other direction, the wiper seal 175 will also swap from one orientation to the other. This occurs by the wiper seal 175 folding over itself in the gap between the base 173a of the seal and the inner surface of the liquid chamber port 159. This folding results in the wiper seal 175 flexing more than it regularly would during ordinary movement of the two components, and as such temporarily provides greater resistance to movement of the liquid chamber 151 than usual.

This increased resistance can be beneficial, as it will likely occur after the liquid chamber 151 has been connected, right before the user initially attempts to remove the liquid chamber from the recess 108. In this situation, the effect of the wiper seal 175 changing orientation would provide a temporary resistance that needs to be overcome before the liquid chamber 175 can removed. This helps prevent the liquid chamber 151 from accidentally becoming dislodged from engagement with the breathing assistance apparatus 10, but does not inhibit the removal of the liquid chamber 151 once it has begun moving relative to the housing 100.

In an advantageous configuration, the chamber connection ports 161, 163 of the breathing assistance apparatus base unit 50 would each have a single seal 173 located in a single recess, the seal having two sealing elements 175 in the form of two wiper seals. The wiper seal closer to the terminal end 163a of the gas port 163 could have a larger diameter than the other wiper seal (i.e. h1>h2). A longer wiper seal provides a more reliable seal and accommodates variation in the inner diameter of the respective base unit connection port 157, 159 of the liquid chamber, but also requires a greater amount of travel in order to settle in the correct position. This greater amount of travel is provided by the liquid chamber 151 contacting the front wiper seal earlier when connecting the liquid chamber.

In an alternative configuration, the wiper seal closer to the terminal end 163a of the gas port 163 could have a smaller diameter than the other wiper seal (i.e. h2>h1), but due to an internal taper of the ports 157, 159 of the liquid chamber 151, there will be a greater interference between the port 157, 159 and the wiper seal closer to the terminal end 163a of the gas port 163 than the other seal. Similarly, h1 and h2 could be equal, with greater interference between the port 157, 159 and the wiper seal closer to the terminal end 163a of the gas port 163 than the other seal, due to the internal taper of ports 157, 159.

In another alternative configuration, the wiper seals may have the same dimensions. In another alternative configuration, the wiper seals may have three or more sealing elements 175.

In another alternative configuration, the wiper seals could be shaped to follow an internal taper of the ports 157, 159, so that there is the same interference between each wiper seal and the port 157, 159.

Alternatives to the wiper seal include using an O-ring, L-seal or an X-ring. A wiper seal is preferred to these alternatives as it provides less resistance to the movement of the liquid chamber 151, and is easier to assemble and replace. The O-ring and X-ring have the advantage of having a higher pressure threshold; however, the pressure threshold for the wiper seal exceeds the pressures that would be used in the breathing assistance apparatus 10.

As a further alternative, one or more wiper seals could be used in addition to one of the alternative types of seals listed above or other suitable seal(s).

Figure 11:
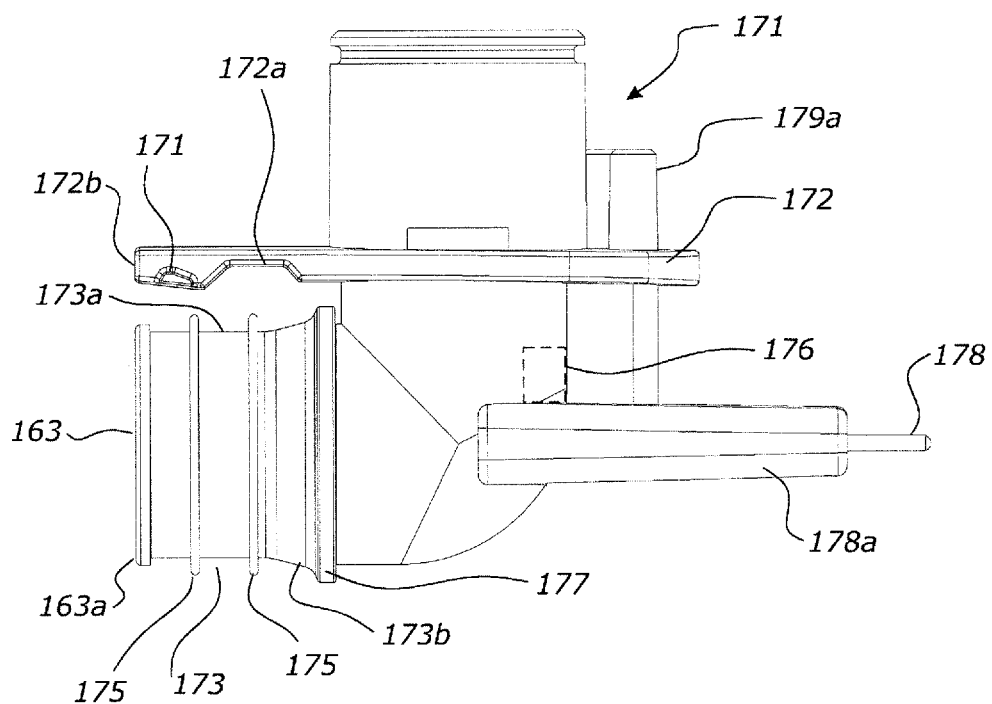
FIG. 11 is a right side view of the elbow showing the location of temperature sensor(s) in broken lines.

As shown in FIGS. 11 and 12, the seal 173 has a further sealing element at or adjacent an opposite end of the seal 173 from the terminal end 163a of the gas port 163. In one configuration, the base 173a of the seal 173 also has an outward taper 173b leading to a radially projecting flange 177. The flange 177 is positioned at or adjacent an end of the seal 173 that is at or adjacent the proximal end 163b of the port 163 that is opposite to the terminal end 163a. The flange 177 is configured to form a seal with a component that differs from the first component (the base unit connection port 157, 159 of the liquid chamber). Therefore, the flange 177 has a configuration that differs from the wiper seals 175. In the form shown, the flange projects radially further outwardly than the wiper seals 175, so that the portion of the seal 173 with the flange has a larger diameter to connect with a second component having a larger internal diameter than the liquid chamber port 157, 159. The outward taper 173b assists with guiding the different component into contact with the flange 175.

Figure 13:
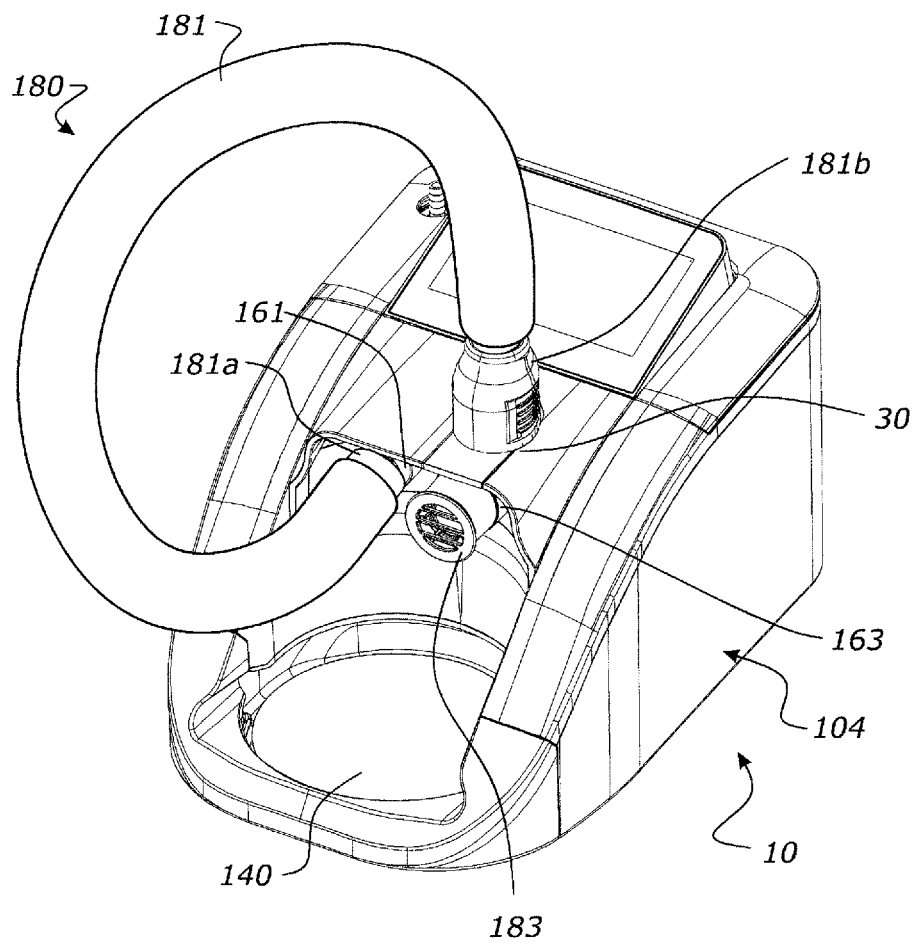
FIG. 13 is a front/right side overhead perspective view showing a disinfection kit mounted to the breathing assistance apparatus.

For example, the larger component may comprise part of a disinfection kit. FIG. 13 shows the components of a disinfection kit 180 connected to the base unit 50 of the breathing assistance apparatus 10. A disinfection tube 181 is connected to the gas outlet port 161 and the patient outlet port 30. An inner surface of a first coupling 181a of the disinfection tube 181 forms an interference fit with the flange 177 on the seal 173 on the gas outlet port 161. The first coupling 181a may have a tapered surface that forms the interference fit. An inner surface of a second coupling 181b of the disinfection tube 181 forms an interference fit with a seal on the patient outlet port 30.

A filter cap 183 is connected to the humidified gas inlet port 163. An inner surface of the filter cap 183 forms an interference fit with the flange 177 on the seal 173 on the humidified gas inlet port 163. The filter cap 183 may have a tapered surface that forms the interference fit.

In one configuration, the disinfection tube 181 and the filter cap 183 do not contact the wiper seals 175, due to the larger diameter of the flange 177. This means that the disinfection kit may operate to disinfect the wiper seals 175 as well as the ports 161, 163, 30, and elbow 171. In an alternative configuration, the disinfection tube 181 and the filter cap 183 could seal with the wiper seals 175 in addition or as an alternative to the seal formed with the flange 177.

In an alternative configuration, the flange 177 could be an integral part of the port 161, 163 instead of the seal 173, and therefore made of hard plastic. In this configuration the disinfection tube 181 and filter cap 183 could still form an interference fit between the tapered surfaces and the flanges 177.

The terminal ends 161a, 163a of the ports 161, 163 may contact a step on the internal surface of the liquid chamber 151, thereby limiting the insertion depth of the ports 161, 163 during use. The flange 177 and taper 173b would not have any interaction with the liquid chamber 151 during use of the device, as the liquid chamber 151 does not contact the flange 177 and/or taper 173b. In an alternative configuration, the liquid chamber 151 could contact the flange 177 and/or taper 173b. This contact could result in an additional seal between the breathing assistance apparatus 10 and the liquid chamber 151.

The flange 175 and taper 173b can serve an additional purpose of providing a surface for the user to push on when connecting the removable elbow 171 to the housing 100.

Figure 2:
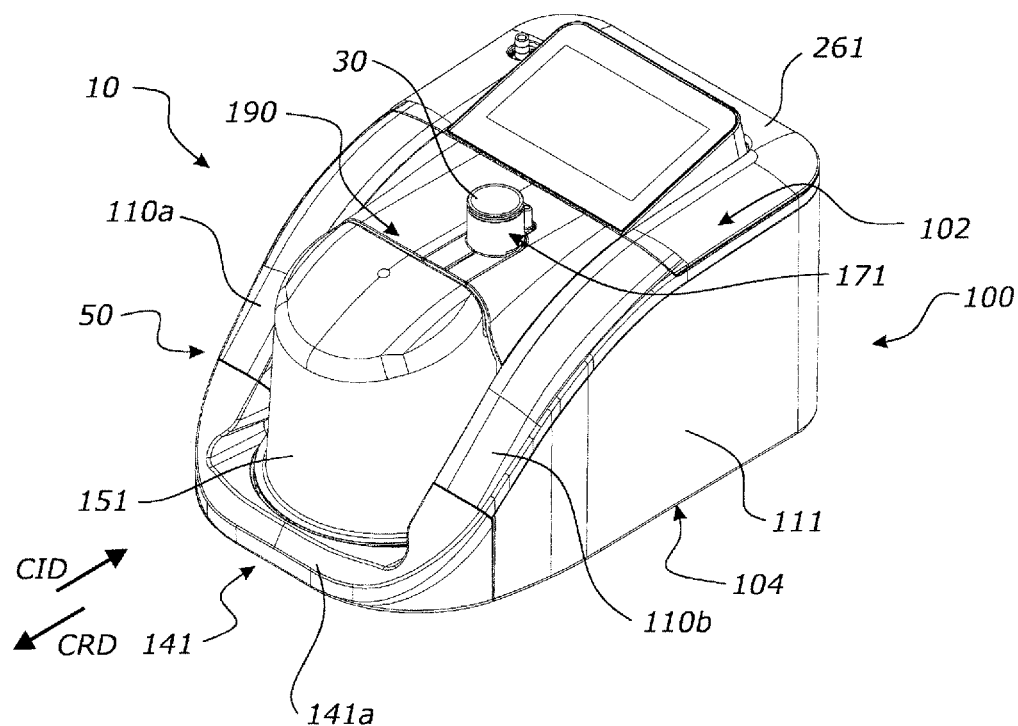
FIG. 2 is a front/right side overhead perspective view of a breathing assistance apparatus with a humidifier liquid chamber positioned in the recess of the breathing assistance apparatus base unit.
Figure 6:
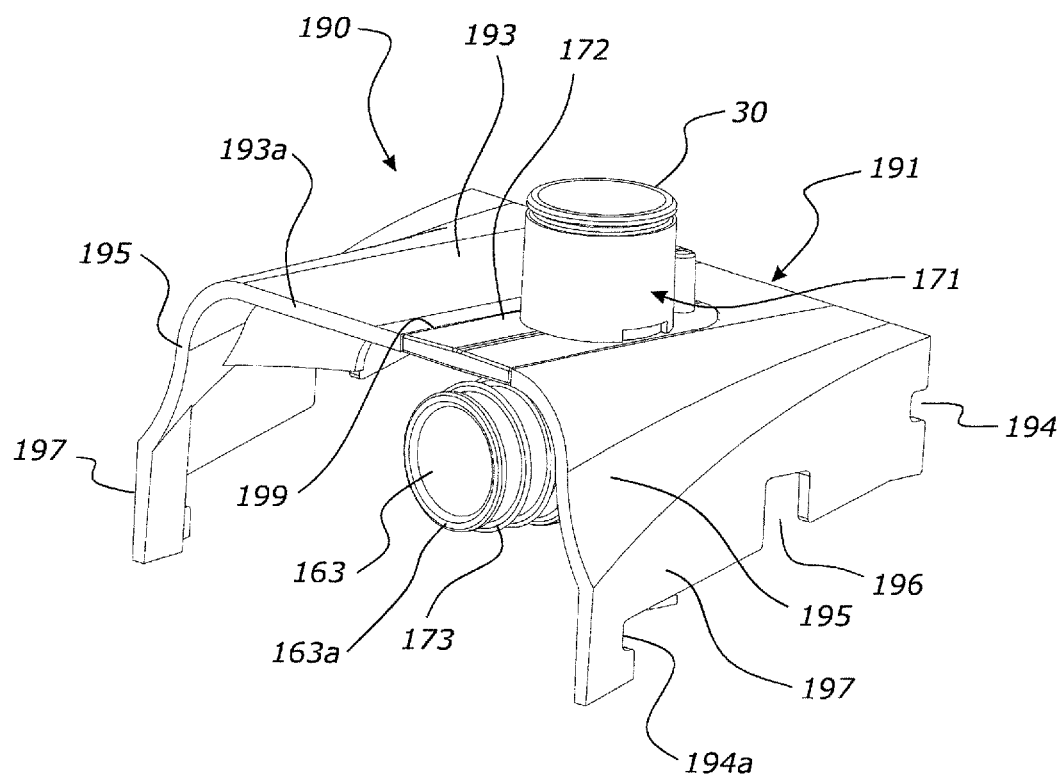
FIG. 6 is a front/right side overhead perspective view of a removable elbow and shroud of the breathing assistance apparatus base unit.

The base unit 50 of the apparatus comprises a shroud 190 that cooperates with the housing 100 and the removable elbow 171. FIG. 6 shows the removable elbow 171 connected to the shroud 190. As shown in FIG. 2 for example, the shroud 190 serves to create a uniform upper surface of the housing 100 of the apparatus 10, with the patient outlet port 30 of the removable elbow 171 protruding upwardly through the shroud 190. The shroud 190 is configured such that it is not removable from the housing 100 in normal use of the apparatus 10.

Figure 9:
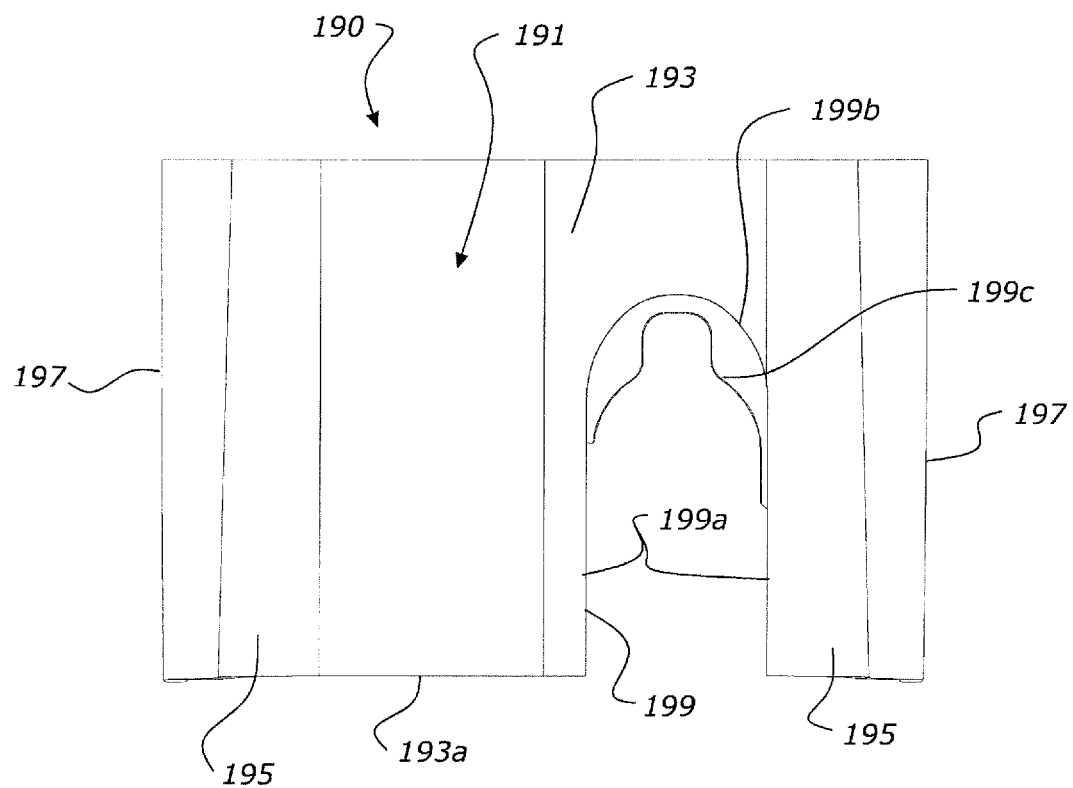
FIG. 9 is a top plan view of the shroud and elbow, prior to insertion of the elbow into the shroud.
Figure 9:
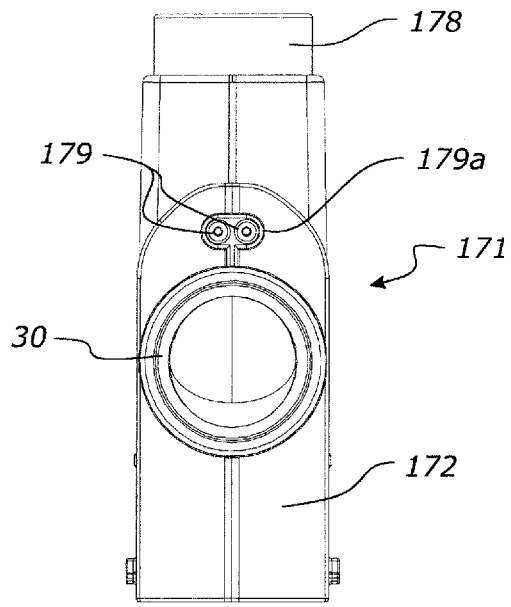

As shown in FIGS. 6 and 9, the shroud 190 comprise a body 191 having a substantially flat horizontal upper surface 193, two contoured shoulders 195 having a substantially sinuous configuration that extend downwardly and outwardly from opposite sides of the upper surface 193, and two substantially vertical downwardly extending outer side walls 197. A recess 199 extends rearwardly into the upper surface 193 from a forward edge 193a of the upper surface 193. The recess 199 is sized and configured to receive part of the removable elbow 171, to provide an unobstructed path for the removable elbow 171 to be connected to the housing 100 of the base unit 50 of the apparatus 10. In the form shown, the recess is defined by a pair of substantially parallel side walls 199a and an upper arcuate rear wall portion 199b. A contoured tapering rear wall region 199c projects into the recess from the arcuate rear wall portion, and is positioned beneath the arcuate rear wall portion 199b. The contoured tapering rear wall region is configured to receive a chimney 179a of the removable elbow.

Similarly, the removable elbow 171 has a flat horizontal tab 172 extending from the elbow that has a shape that is complementary to the shape of the recess 199 in the shroud, such that when the removable elbow 171 is assembled with the apparatus 10, the flat horizontal tab 172 is received in the recess 199 to create a uniform surface. This tab 172 can additionally provide an upper surface for the conduit 16 to contact when connecting the conduit 16 to the patient outlet port 30 of the elbow.

Figure 7:
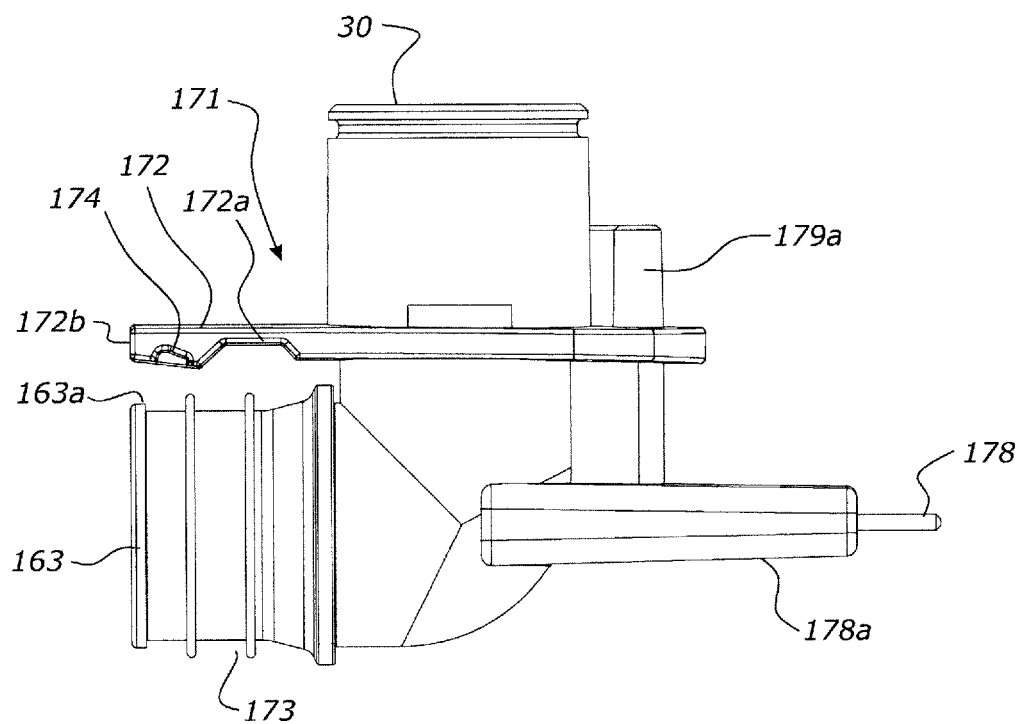
FIG. 7 is a right side view of the elbow.
Figure 8:
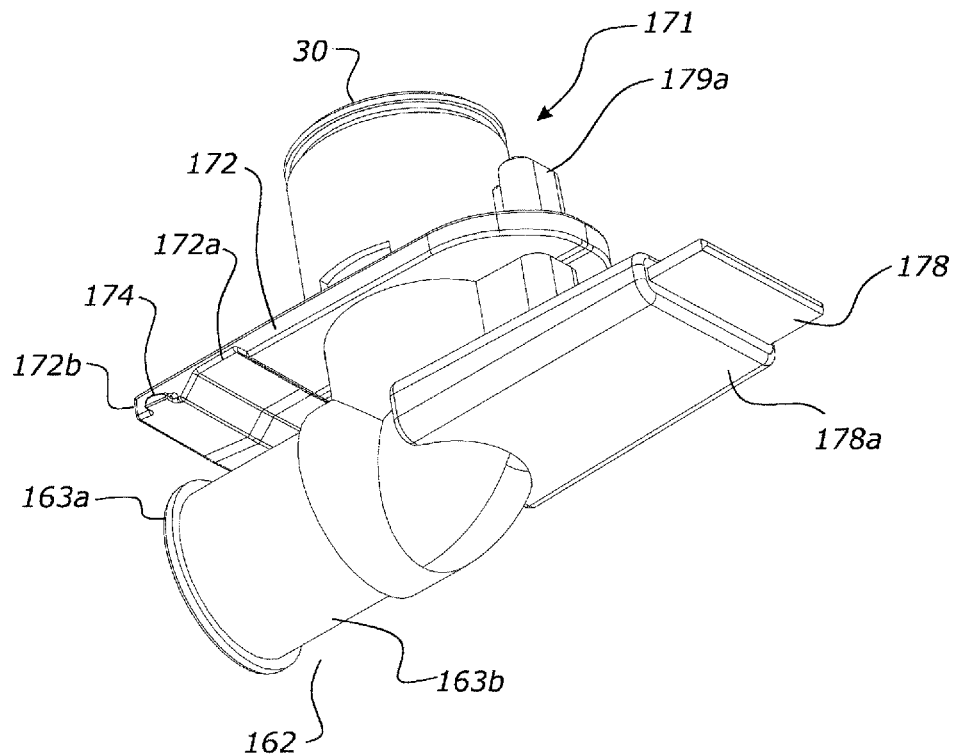
FIG. 8 is a rear/right side perspective view showing the elbow from below, and with the seal not shown.

As shown in FIGS. 7 and 8 for example, the flat horizontal tab 172 can have a thinned portion 172a adjacent the terminal forward end portion 172b, located between the patient outlet port 30 of the elbow and the terminal forward end portion 172b of the tab. This allows the terminal forward end portion 172b to flex vertically relative to the rest of the elbow 171.

Figure 10:
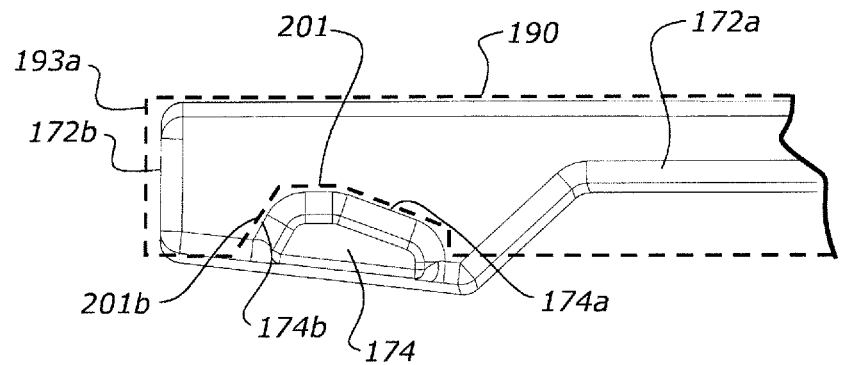
FIG. 10 is an enlarged right side view showing engagement features on the elbow engaging with the shroud (broken lines).
Figure 14:
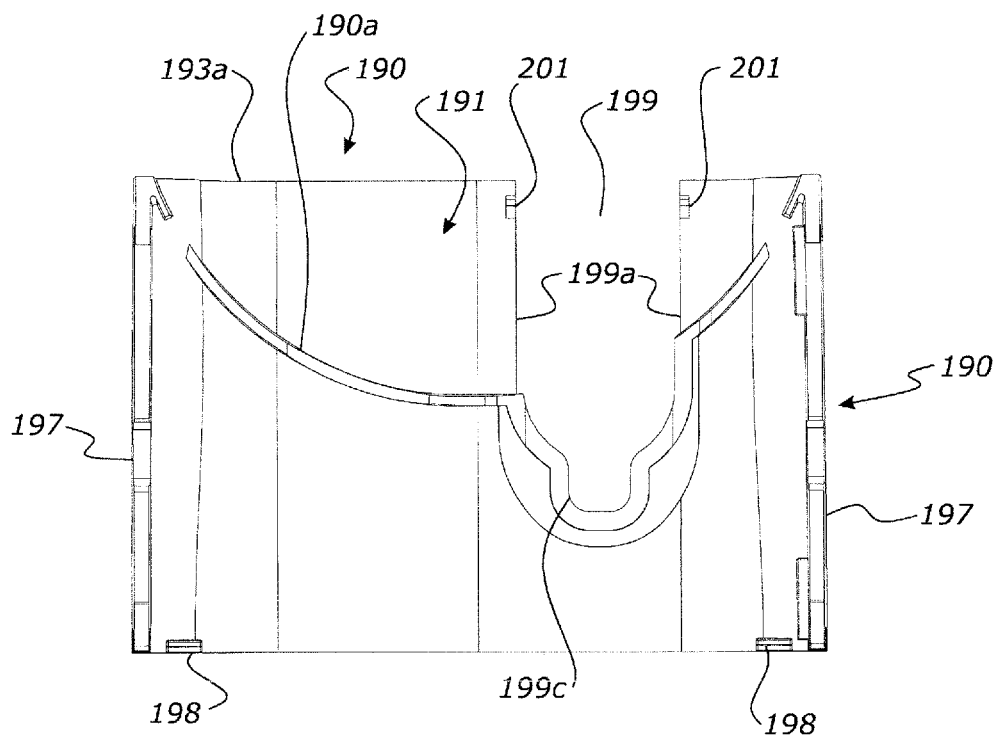
FIG. 14 is an underside view of the shroud showing engagement protrusions.

The flat horizontal tab 172 also has engagement features comprising two protrusions 174 extending outwardly from opposite sides of the terminal forward end portion 172b of the tab. The protrusions 174 are configured to interact with engagement features comprising complementary engagement recesses 201 extending outwardly from either side wall 199a of the recess 199 of the shroud of the housing, on the underside of the shroud, as shown in FIGS. 10 and 14. The removable elbow 171 is configured to connect to the housing by moving the removable elbow in a first direction relative to the housing (rearwards towards the housing). The removable elbow 171 is configured to disconnect from the housing by moving the removable elbow 171 in a second direction (forwards relative to the housing) that is opposite to the first direction. Due to the interaction of the engagement features, the removable elbow 171 is configured to inhibit movement of the removable elbow 171 in the second direction in the absence of actuating part of the removable elbow, e.g. the terminal forward end portion 172b, relative to another part of the removable elbow to flex the tab. That inhibits removal of the removable elbow 171 from the shroud 190 of the housing 100.

The rear portion of each protrusion 174 is designed with an angled surface 174a (FIG. 10). When the elbow 171 is inserted into the housing 100, this surface 174a contacts the underside of the front edge 193a of the shroud, causing the terminal end 172b of the tab to flex downwards by bending in the thinned section 172a. Once the elbow 171 has been fully inserted, the protrusion 174 will reach the complementary engagement recess 201 in the shroud. At this point the protrusion 174 will engage with the recess 201 as the tab 172 flexes back into a flat and horizontal position. When engaged, the front surface 174b of the protrusion will contact a complementary surface 201b of the engagement recess.

The front surface 174b of the protrusion is steeper, i.e. more vertical, than the rear surface 174a, such that if a user attempts to pull out the elbow 171 from the shroud 190, and thereby from the housing 100, the contact between the front surface 174b of the protrusion and the complementary surface 201b of the recess should not cause the tab to flex downwards, unless a sufficiently high force is applied to the elbow 171.

In an alternative configuration, the removable elbow 171 and shroud 190 may each have a single one of the engagement features 174, 201, rather than each having two engagement features.

In order to remove the elbow 171 from the housing 100, the user would typically first press downwards on the upper surface of the terminal forward end portion 172b of the tab 172, in order to actuate that part of the tab 172 by flexing the tab and disengage the protrusions 174 from the engagement recesses 201. Only once the tab has been flexed can a user then pull the elbow 171 out from the housing 100. One advantage of this is that it helps prevent the elbow 171 from coming loose when the liquid chamber 151 is being removed from the apparatus by pulling the liquid chamber 151 out of the recess 108.

This configuration allows a user to easily assemble the elbow 171 with the housing 100 in a single one-handed motion, but requires more complex interaction to then disassemble it. If a user does not understand how to correctly remove the elbow 171 and attempts to remove the elbow by pulling on it without actuating the tab 172, the engagement features will ultimately disengage from each other under a sufficiently high force. This will avoid damage of the removable elbow 171 and/or shroud 190.

In an alternative configuration, the engagement features may be configured such that the removable elbow 171 cannot disconnect from the shroud 190 of the housing 100 in the absence of actuating the tab 172, e.g. the terminal forward end portion 172b. This could be achieved by having vertical front surfaces 174b, 201b rather than angled front surfaces.

FIG. 11 schematically shows a position 176 of temperature sensor(s) such as thermistor(s) in the removable elbow 171. The thermistors are located in the rear vertical wall of the upstanding portion of the elbow, close to the curved transition region between the vertical and horizontal elbow portions. At this location, the thermistors are relatively shielded from the heat produced by the heater plate 140, allowing for more accurate estimations of the temperature of gases flowing through the removable elbow 171 to be made.

The elbow 171 has electrical connectors 179 positioned in an upstanding chimney 179a, the connectors configured to provide power from a main power board of the apparatus 10 to the heater wires 16a in the conduit 16.

As mentioned above, the shroud 190 is designed to not be removed during regular use. The shroud has features that allow it to be clipped onto a screen carrier 211, which in turn is fastened to the upper chassis 102 to become part of the housing 100. The screen carrier 211 can connect to and support a display 212. In alternative configurations, the screen carrier 211 may not be provided, and the shroud 190 may clip directly to part of the housing 100, such as an upper surface or upper chassis 102 of the housing.

FIGS. 16 to 19 show features on the shroud 190 and screen carrier 211 for attaching the components together without the use of fasteners. The shroud 190 is configured to attach to the screen carrier 211 of the housing 100 via two movements; an initial movement of the shroud in a first direction followed by a subsequent movement of the shroud in a second direction that is offset from the first direction. In one configuration, the second direction is transverse to the first direction. In the form shown, the shroud 190 is configured to initially be moved in a first downward direction DD, followed by a movement in a second rearward direction RD, relative to the screen carrier 211 and thereby the housing 100. In the form shown, the downward direction DD is vertical and the rearward direction RD is horizontal.

The shroud 190 is configured so that the shroud cannot be detached from the screen carrier 211 of the housing solely by pulling the removable elbow 171 in the second forwards direction relative to the housing 100.

Figure 17:
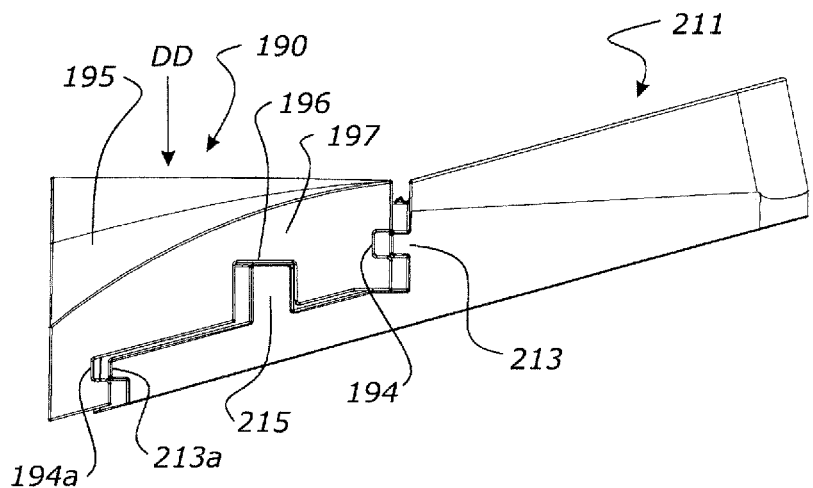
FIG. 17 shows a first step of engaging the shroud with the screen carrier of the upper chassis.
Figure 18:
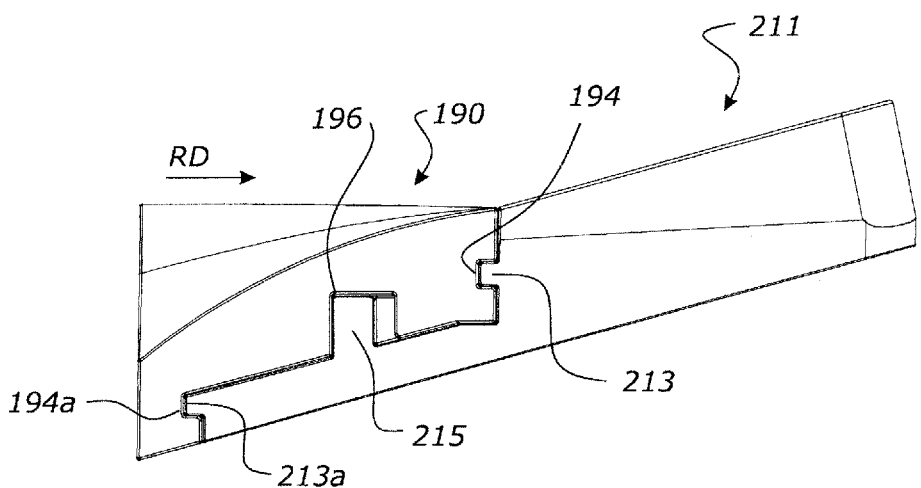
FIG. 18 shows the shroud once engaged with the screen carrier.
Figure 19:
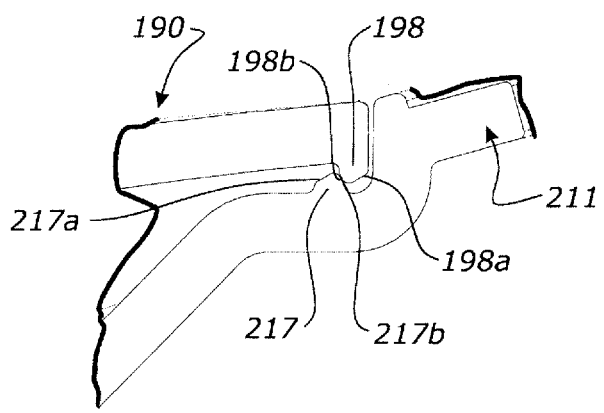
FIG. 19 shows engagement of the engagement protrusions of the shroud and the screen carrier.

As shown in FIGS. 17 and 18, each side 197 of the shroud 190 is shaped to be complementary to the shape of the screen carrier 211. The sides of the screen carrier 211 of the housing 100 have two forwardly directed horizontal protrusions 213 (one per side wall) that engage with complementary rearwardly open recesses 194 in rear walls on each side of the shroud 190 as the shroud is moved in the rearward direction relative to the housing. Once the shroud 190 is connected to the screen carrier 211, the horizontal protrusions 213 being received in the recesses 194 prevent vertical movement of the shroud 190.

Similarly, the screen carrier 211 of the housing 100 has an upstanding vertical protrusion 215 on each side that engages with a complementary downwardly open recess 196 in the bottom of each side wall 197 of the shroud as the shroud is moved in the downward direction relative to the housing. Unlike the horizontal protrusions, the vertical protrusion 215 is narrower than the complementary recess 196 in the shroud. This allows for a small amount of horizontal movement in the rearward direction RD as shown in FIGS. 17 and 18. The vertical protrusion 215 and recess 196 aid in aligning the shroud 190 with the screen carrier 211 during assembly.

The shroud 190 is first placed above the screen carrier 211 and moved in the downward direction DD to the position shown in FIG. 17. The shroud is then slid horizontally in the rearward direction RD such that the horizontal protrusions 213 engage with the complementary recesses 194 in the shroud, as shown in FIG. 18.

The shroud 190 and screen carrier 211 may have a second set of forwardly extending horizontal protrusions 213a and rearwardly open recesses 194a toward a forward end of the screen carrier 211 and shroud 190, to further inhibit vertical movement of the shroud 190 relative to the screen carrier 211.

The shroud 190 and screen carrier 211 of the housing 100 additionally have features to inhibit horizontal movement of the shroud relative to the screen carrier when they are fully engaged in the position shown in FIG. 18, to therefore inhibit removal of the shroud from the housing. As shown in FIGS. 14-16 and 19, the shroud has one or more downwardly extending engagement protrusions 198 (two in the configuration shown) that extend downwards from the back of the lower surface of the shroud 190. The engagement protrusions 198 are configured to engage with complementary upwardly extending engagement protrusion(s) 217 extending from an upper surface of the screen carrier 211. Both sets of engagement protrusions 198, 217 have a first side 198a, 217a with a relatively flat angle, and a second side 198b, 217b with a relatively steep angle. When attaching the shroud 190 to the screen carrier 211 by moving the shroud in the rearward direction RD, the first sides 198a, 217a of each set of engagement protrusions will interact with each other by contacting each other, and the relatively flat angle on the surface of each engagement protrusion will cause the shroud 190 to briefly and easily flex as the engagement protrusions clip into place. That is, the first sides 198a, 217a are configured to interact with each other when attaching the shroud to the screen carrier.

Once the shroud 190 is connected to the screen carrier 211, the second sides 198b, 217b of each set of protrusions will contact each other. The steeper angle on the surface of the second sides 198b, 217b of the engagement protrusions means that a larger horizontal force is required in order to cause the shroud 190 to flex in the same way as before. The result of this is that assembly of the shroud 190 and screen carrier 211 requires less force than disassembly. The second sides 198b, 217b are configured to interact with each other once the shroud is attached to inhibit removal of the shroud from the screen carrier of the housing. The shroud can still be removed by moving the shroud 190 forwards in direction opposite to the rearward direction RD, if a large enough force is applied. However, this would only be done by a technician if some form of maintenance were being performed on the apparatus. The features above are designed such that the shroud 190 would not be removed during normal use (even accidentally).

It can be seen from FIGS. 14-19 that the engagement features on the shroud 190 and screen carrier 211 are such that the upper surface of the screen carrier can be configured so that there are no, or a minimal number of, exposed fasteners (such as screws) on the underside of the shroud and the upper surface of the screen carrier, meaning that the shroud and upper surface of the screen carrier are easy to clean.

Figure 15:
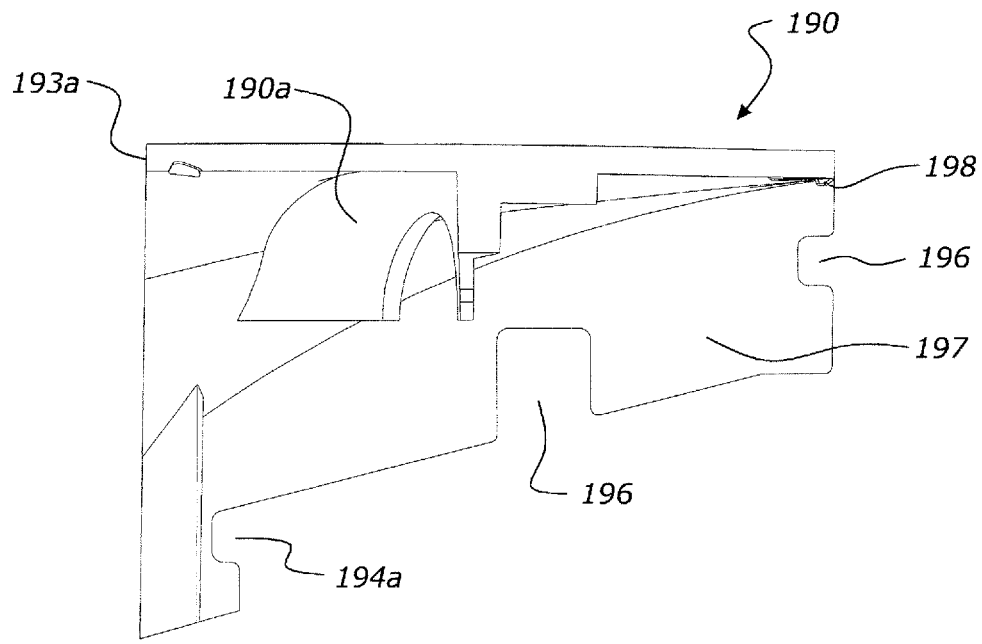
FIG. 15 is a right side sectional view of the shroud.
Figure 16:
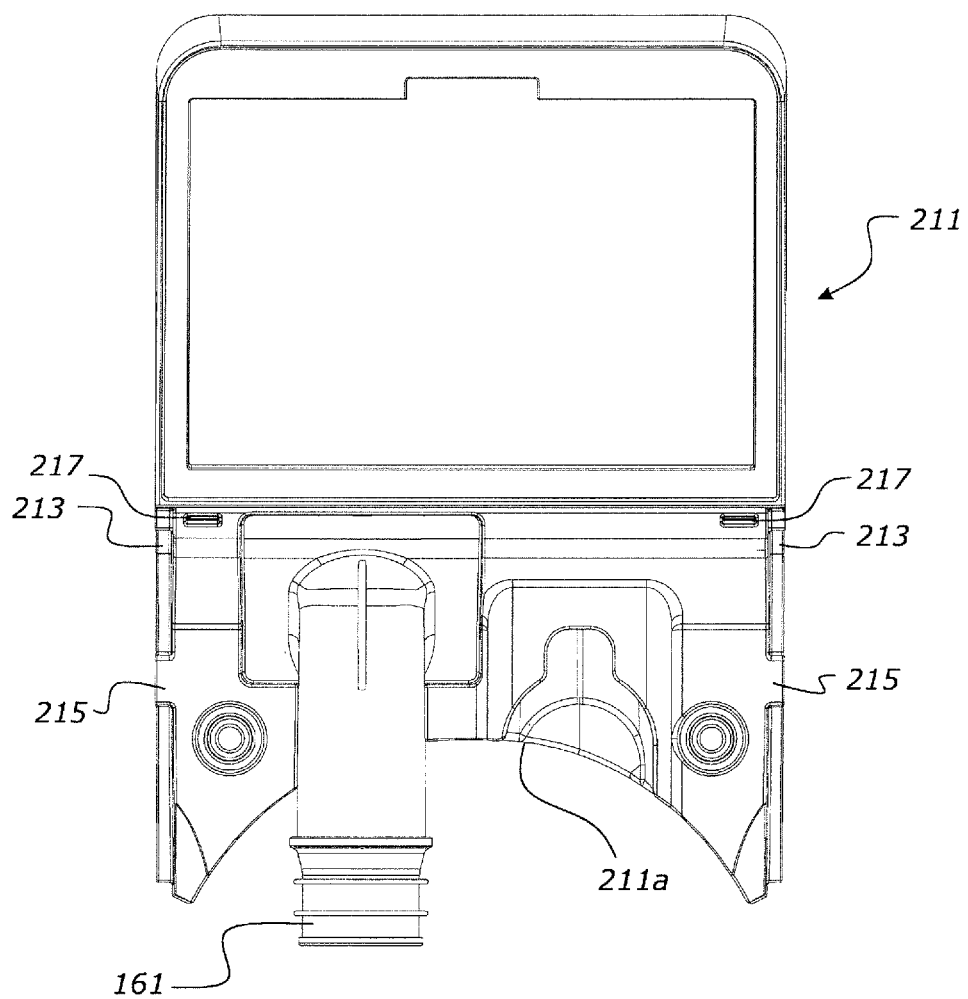
FIG. 16 is a top plan view of the screen carrier of the housing of the breathing assistance apparatus base unit, showing complementary protrusions.

Referring to FIGS. 14 to 16, the shroud 190 has a downwardly projecting forward wall 190a that is complementary to a surface 211a of the screen carrier 211 of the housing. The forward wall 190a is configured to contact the surface 211a of the screen carrier 211 when the shroud is attached to the screen carrier. In the form shown, the forward wall 190a and the surface 211a are arcuate, to follow the shape of a rear wall of the recess 108 for receipt of the liquid chamber 151. Alternatively, the forward wall 190a and the surface 211a could have different shapes, such as a substantially straight shape for example.

Once the shroud 190 is assembled with the screen carrier 211, the forward wall 190a and surface 211a contact each other. This avoids an exposed gap between forward portions of those components, which would need to be cleaned if the gap was present. Due to the tight complex geometry, such a gap would be difficult to clean, which might mean the shroud would need to be removed for satisfactory cleaning. Avoiding such a gap enables the shroud 190 to be non-removable or difficult to remove, without creating cleaning issues.

The removable elbow 171 is removable from the housing 100 when the shroud 190 is attached to the housing.

In an alternative configuration, one or more of the engagement protrusions 198, 217 can be replaced with an engagement recess. One side of the engagement recess would have a surface that is complementary to the second side of the engagement protrusion in order to inhibit disassembly in a similar way to the above configuration. In a further configuration, one or more of the engagement protrusions 198, 217 could be replaced with a combination of an engagement protrusion and engagement recess, such that a complementary engagement protrusion engages over the engagement protrusion and within the engagement recess.

A similar shroud 190 and screen carrier 211 and/or housing 100 engagement configuration could be used where the shroud 190 acts as a cover for part of the housing or another component, but where the component that is covered is not removable.

Referring to FIGS. 7 and 8, the removable elbow 171 also includes an electrical connection. The elbow 171 has an inlet for pneumatically connecting to a first accessory for the breathing assistance apparatus 10, such as the liquid chamber 151, an outlet for pneumatically and optionally electrically connecting to a second accessory for the breathing assistance apparatus, such as the patient conduit 16, and a printed circuit board (PCB) electrical connector 178 for electrically connecting to the breathing assistance apparatus 10 to form an electrical connection with an electrical component in the housing. The electrical connection provides an electrical link between the base unit 50 of the apparatus 10 and the temperature sensors 176 embedded in the elbow, as well as between the base unit 50 of the apparatus 10 and the conduit 16 (when the conduit has one or more sensors and/or a heating element), via an electrical interconnecting assembly 221 in the housing which will be described below. The PCB electrical connector 178 electrically connects to the electrical interconnecting assembly 221 when the removable elbow 171 is connected to the housing 100.

The pneumatic inlet connection of the removable elbow 171 is provided by the humidified gas inlet port 163, the pneumatic outlet connection is provided by the patient outlet port 30, and the outlet electrical connection is provided by connectors 179 (FIG. 9) that are provided in the chimney 179a that extends upwardly parallel to an axis of the port 30.

The humidified gas inlet port 163 and the patient outlet port 30 are in fluid communication with each other via a gas flow path in the removable elbow. Electrical connectors 178, 179 of the removable elbow are pneumatically isolated from the gas flow path between the humidified gas inlet port 163 and the patient outlet port 30, via at least one wall of the removable elbow. For example, the body of the removable elbow may be injection moulded plastic material, with isolated regions provided for the electrical connectors that are separate and isolated from the gas flow path.

Because the portion of the removable elbow, namely PCB electrical connector 178, that is configured to form the electrical connection with the electrical component in the housing (the electrical interconnecting assembly 221) is pneumatically isolated from the gas flow path of the removable elbow, coupling the removable component to the housing solely provides an electrical connection between the PCB electrical connector 178 and the electrical interconnecting assembly 221. It does not form a direct pneumatic connection between the gas flow path in the removable elbow 171 and the housing 100. Instead, the gas flow path in the removable elbow provides a pneumatic connection between the first accessory (the liquid chamber 151) and the second accessory (the patent conduit 30).

In the configuration shown, the PCB electrical connector 178 is partly housed in a housing 178a that is integrally formed with the elbow. The PCB electrical connector projects rearwardly from the housing 178a to insert into an electrical connector on the base unit 50 of the apparatus 10 in a horizontal direction (i.e. the same rearward insertion direction CID in which the liquid chamber 151 connects to the housing 100 of the base unit 50 and the same rearward direction RD in which the shroud 190 connects to the screen carrier 211). As such, the removable elbow 171 can be horizontally connected to the apparatus in the rearward direction RD, with the liquid chamber 151 being horizontally connected to the two apparatus ports 161, 163 after that. Alternatively, the liquid chamber 151 can initially be connected to the removable elbow 171, with the assembled liquid chamber 151 and elbow 171 then being connected to the base unit 50 of the apparatus together by moving them in the rearward direction together.

This allows the components to be assembled and disassembled in multiple ways. Specifically, the elbow 171 will make three connections during assembly. These three connections are the connection between the elbow 171 and the patient conduit 16, the connection between the elbow 171 and the liquid chamber 151, and the connection between the elbow 171 and the housing 100. Each of these three connections can be made in any order. Similarly, when disassembling the components, these three connections can be broken in any order. This is advantageous as different orders of assembly and disassembly may be preferred in different scenarios.

For example, the removable elbow 171 may be assembled with the housing 100 initially as the removable elbow may have come assembled with the housing 100, with the liquid chamber 151 and the conduit 16 not being attached until the apparatus 10 is to be used. As the removable elbow 171 is removed much less frequently than the liquid chamber 151 and/or conduit 16, this will be the most common order of assembly. Additionally, in a hospital setting, the liquid chamber 151 and conduit 16 would be replaced between each patient, while the removable elbow 171 may only be cleaned/disinfected between uses. As such, the removable elbow 171 can be assembled with the housing 100 after being cleaned, with the liquid chamber 151 and conduit 16 again only being connected when a patient needs to use the apparatus 10.

The liquid chamber 151 and conduit 16 may also be removed prior to removing the elbow 171 after the apparatus 10 has been used in order to first throw these components away, with the removable elbow 171 then remaining with the apparatus 10 until it is to be cleaned. The removable elbow 171 may be cleaned while connected to the housing 100 through use of a disinfection kit as described above.

The conduit 16 and/or liquid chamber 151 may be preassembled with the removable elbow 171 after having cleaned the elbow 171, thereby allowing all three components to be able to quickly connect to the housing 100 in one motion when required.

The removable elbow 171 may be disconnected from the housing 100 with the conduit 16 and liquid chamber 151 still attached, which may be useful, for example, in situations in which the patient has a particularly infectious disease. In these situations, it may be desirable to disconnect the removable elbow 171 in this way, such that the circuit is largely still contained and can easily be thrown away in its entirety.

Connecting and disconnecting the preassembled removable elbow 171, conduit 16 and liquid chamber 151 to/from the housing 100 is facilitated by the removable elbow 171 and liquid chamber 151 connecting in the same direction (i.e. rearwardly in a horizontal direction), as well as the shroud 190 not needing to be attached over the removable elbow 171 after the removable elbow 171 has been inserted.

As shown in FIGS. 28 to 36, the PCB electrical connector 178 of the removable elbow 171 inserts into an electrical interconnecting assembly 221 of the base unit 50 of the apparatus 10. The interconnecting assembly 221 is made up of three components; a socket 231, a PCB 241, and an overmould 251. The socket defines a receptacle to receive the PCB electrical connector of the removable elbow.

Figure 29:
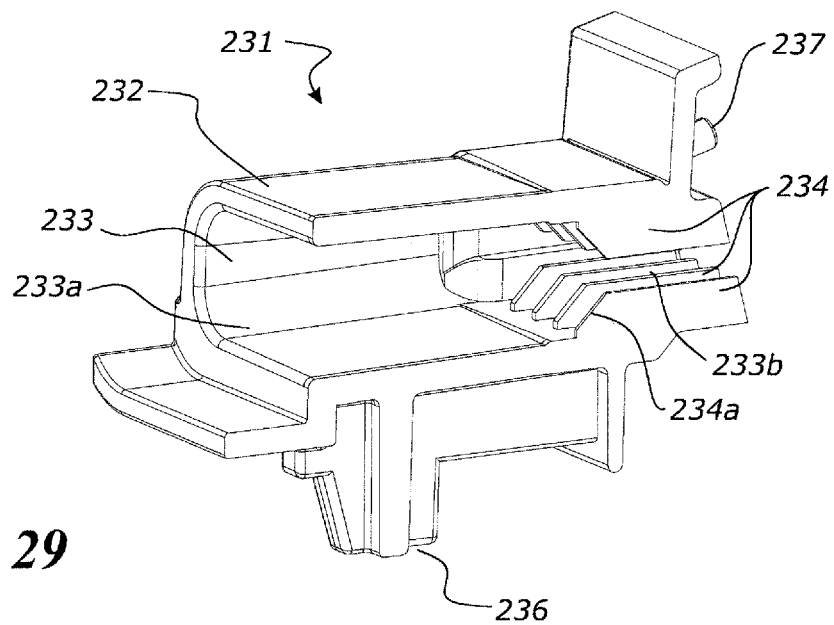
FIG. 29 is a front/right side overhead perspective sectional view of a socket of the interconnecting assembly.
Figure 30:
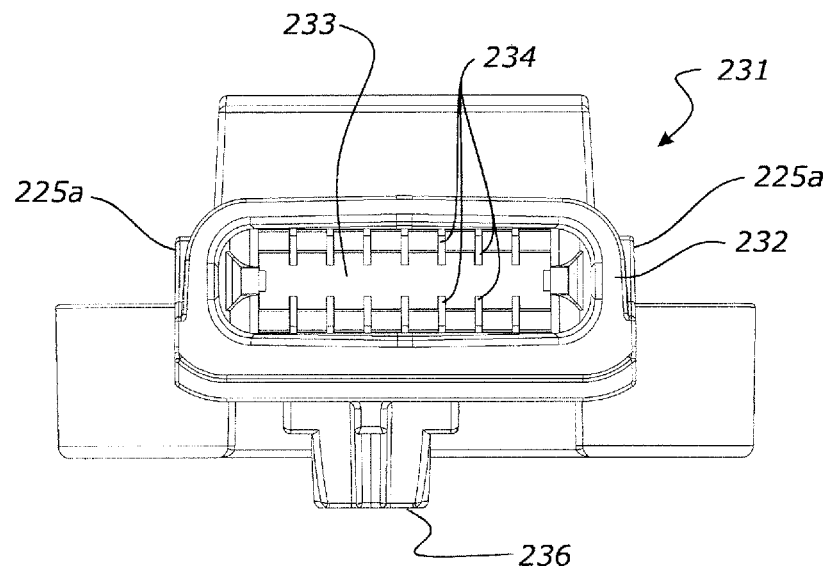
FIG. 30 is a front view of the socket.

As shown in FIGS. 29 and 30, the socket 231 comprises a housing 232 that defines a receptacle 233 to receive the PCB electrical connector 178 of the removable elbow 171. A forward portion 233a of the receptacle 233 has relatively large vertical and horizontal dimensions to receive the housing 178a of the electrical connector. A rear portion 233b of the receptacle 233 has relatively small vertical and horizontal dimensions to receive the portion of the PCB electrical connector 178 that projects rearwardly from the housing 178a. The rear portion 233b is defined between upper and lower ribs 234 that extend into the rear part of the receptacle from upper and lower walls thereof. The rear portion 233b of the receptacle is configured to form a close or tight fit with the PCB electrical connector 178 to assist with holding the removable elbow 171 in connection with the socket 231 via contact between the rear portion 233b of the receptacle and the PCB electrical connector 178. The forward portion 233a of the receptacle may be configured to form a close or tight fit with the housing 178a of the PCB electrical connector 178 to assist with holding the removable elbow 171 in connection with the socket 231. Alternatively, that may form a looser fit.

The interaction of the socket 231 with the PCB electrical connector 178 and/or housing 178a, and the interaction of the protrusions 174 and engagement recesses 201, form two spaced apart engagement regions of the removable elbow 171 and the housing 100 (via the shroud 190); at or adjacent a rear part of the removable elbow and at or adjacent a forward part of the removable elbow. This assists with securing the removable elbow to the housing, reducing the likelihood of the removable elbow 171 inadvertently being removed from the housing 100 when the liquid chamber 151 is being removed from the recess 108.

Forward edges 234a of the ribs 234 are angled such that there is a taper region between the forward portion 233a and rear portion 233b of the receptacle 233, to assist with guiding the PCB electrical connector 178 into engagement with the rear portion 233b of the receptacle 233.

Figure 27:
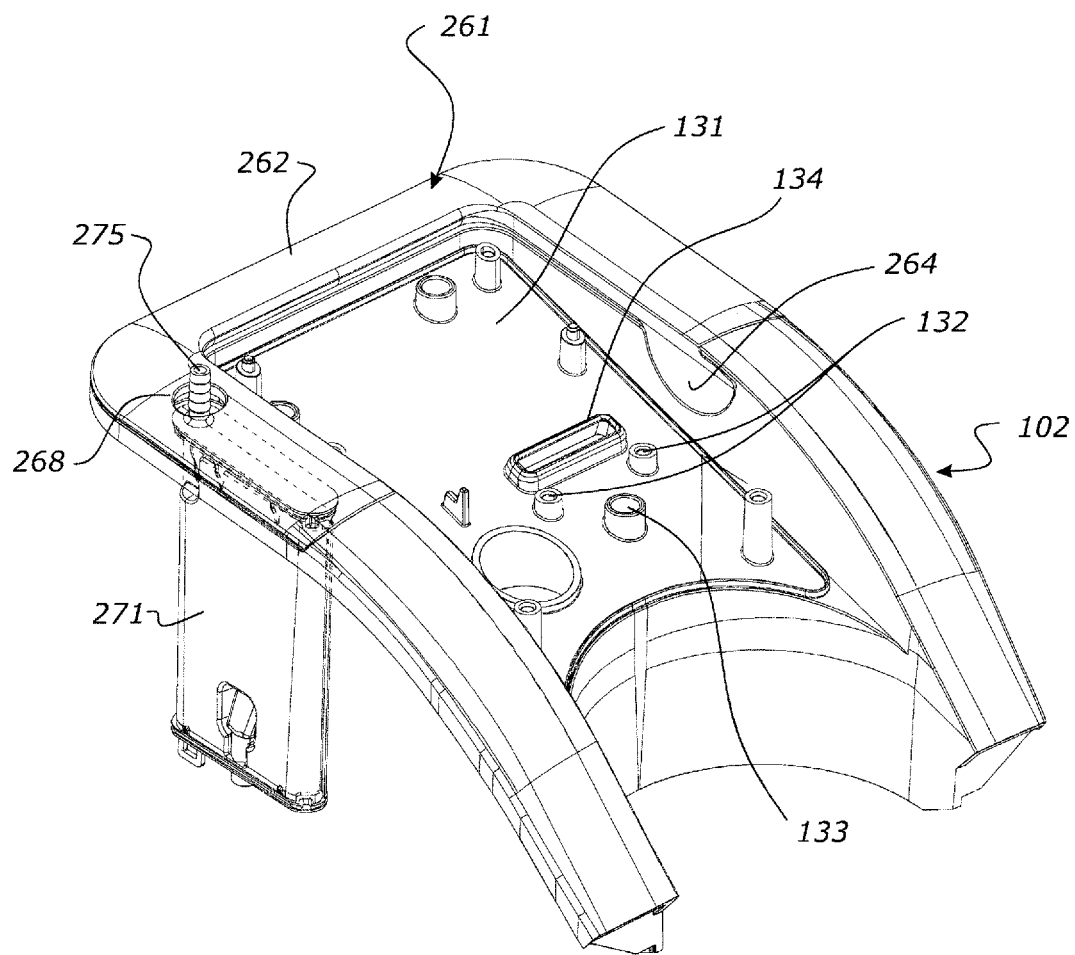
FIG. 27 is a front/left side overhead perspective view showing the filter module in place in the upper chassis and the handle lowered.
Figure 31:
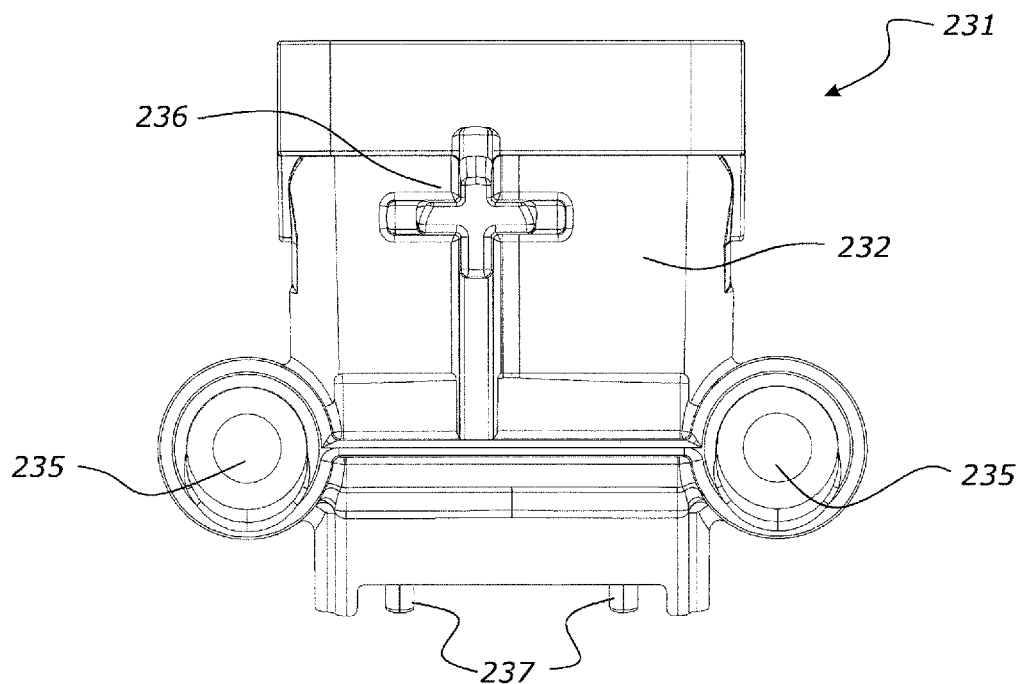
FIG. 31 is a bottom view of the socket.

The socket 231 has multiple features to hold it in place with respect to the housing 100 of the apparatus 10. As shown in FIG. 31, two fastener apertures 235 are located on opposite sides of the socket 231. These apertures 235 are designed for receiving fasteners, such as screws, in order to fasten the socket 231 to the upper chassis 102 of the housing, thereby securing the interconnecting assembly to the housing 100. As shown in FIG. 27, an upper angled surface 131 of the upper chassis 102 that is configured to receive the screen carrier 211, has two complementary apertures 132 for receipt of the fasteners.

The socket 231 also has a mounting protrusion 236 extending downwardly from the underside of the body 232 of the socket. The mounting protrusion 236 is configured to engage with a complementary recess 133 on the angled upper wall 131 of the upper chassis 102 of the housing. In the configuration shown, the mounting protrusion 236 has a cross-shaped cross section, wherein the width and length of the cross will match the internal diameter of the circular recess 133. The engagement between the mounting protrusion 236 and the recess 133 prevents lateral movement of the socket 131 relative to the housing 100, such as could otherwise be caused by connecting and disconnecting the elbow 171. As shown in FIG. 30, the mounting protrusion 236 may be tapered so that its lower end has a smaller dimension than its upper end, to assist with guiding the mounting protrusion 236 into engagement in the recess 133.

Figure 28:
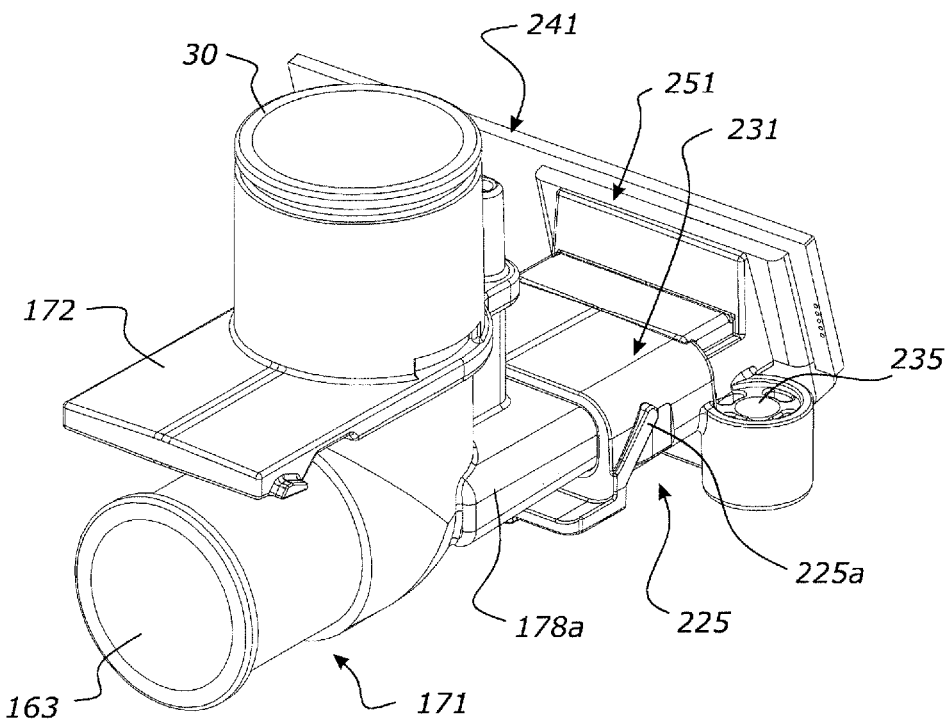
FIG. 28 is a front/right side overhead perspective view showing an electrical interconnecting assembly and the removable elbow.

The angled projections 225a visible on the side of the socket in FIGS. 28 and 30 help create a better seal between the socket 231 and the screen carrier 211 of the housing 100, and help prevent liquid ingress into the screen carrier 211.

Figure 33:
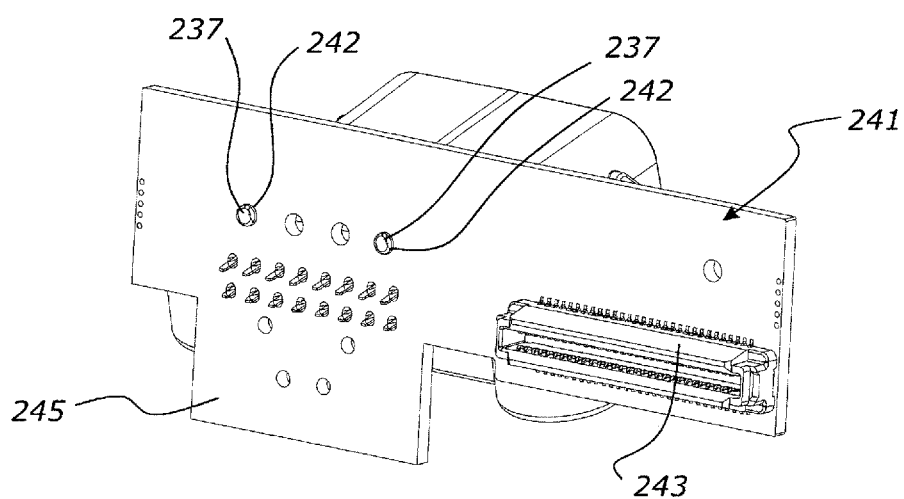
FIG. 33 is a rear perspective view of the PCB and socket of the interconnecting assembly.

As shown in FIG. 33, the PCB 241 of the interconnecting assembly 221 has multiple apertures 242 that engage with complementary protrusions 237 that project rearwardly from a rear wall of the socket 231 in order to correctly position the two components together. More or fewer projections and apertures can be provided.

Once assembled with the housing 100, the interconnecting assembly 231 connects with both the main power board 263a and the display/interface PCB 263b of the apparatus (FIG. 36). The PCB 241 has an electrical connector 243 (shown on the right side of FIG. 34) that connects to the display/interface PCB 263b, as well as a tab 245 (shown on the bottom left of FIG. 34) that forms an electrical connector to connect to the main power board 263a.

The main power board 263a is located between the upper chassis 102 and lower chassis 104 of the housing 100. As shown in FIG. 27, the angled upper surface 131 of the upper chassis 102 has a horizontal transversely extending elongate aperture 134. When assembled with the interconnecting assembly 221, a portion of the PCB 241 extends through this aperture 134 to connect with the main power board 263a.

Due to the main power board 263a operating at high power, the main power board 263a has greater requirements for being sealed against both gases and moisture than the display/interface PCB 263b. By using a PCB 241 in the interconnecting assembly 221 to connect to both the interface PCB 263b and the main power board 263a, the main power board 263a can be sealed simply by sealing the connection between the main power board 263a and the interconnecting PCB 241.

Figure 34:
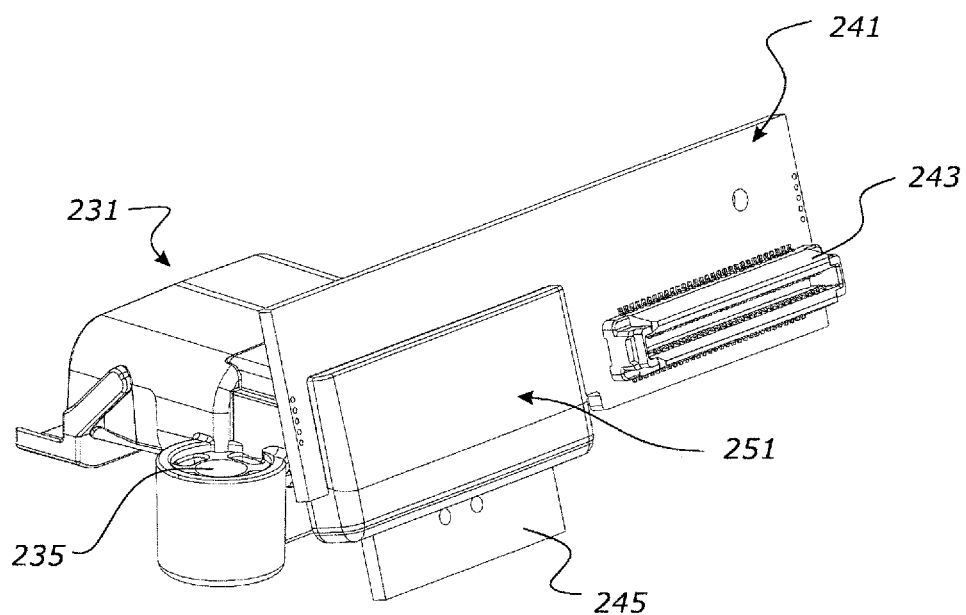
FIG. 34 is a rear overhead perspective view of the interconnecting assembly showing the overmould of the interconnecting assembly.
Figure 35:
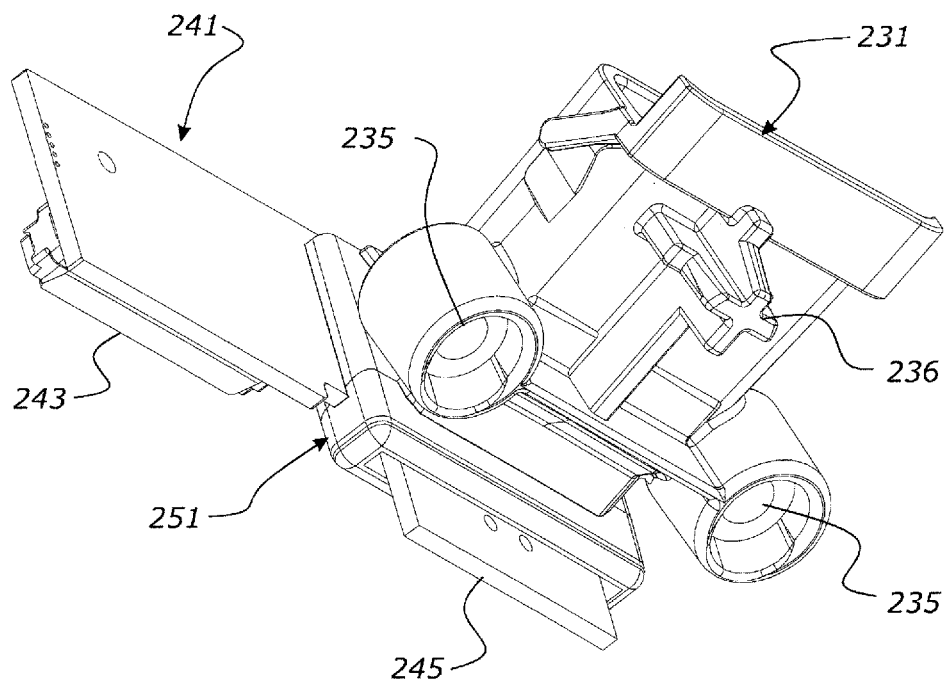
FIG. 35 is a front underside perspective view of the interconnecting assembly showing the overmould of the interconnecting assembly.

As shown in FIGS. 34 and 35, an overmould 251 is applied to the interconnecting assembly 221 to provide a pneumatic seal. The overmould is provided over at least a section of the PCB. The overmould is configured to create a pneumatic seal over the covered section of the PCB and between the overmould and another component of the breathing assistance apparatus. The overmould may moulded from any suitable material, such as polyurethane for example. Any thermoplastic elastomer that is soft and adheres to the board would be suitable. Alternatively, the overmould 251 could be made of silicone, which exhibits less stress relaxation. An interlock may be formed to enhance the adherence between the silicone overmould and the board.

The purpose of the overmould 251 is to pneumatically seal the high power electrical components. The higher power electrical components are the main power board 263a, the section of the PCB 241 that provides the electrical connection between the main power board 263a and the socket 231, as well as the electrical connections within the socket 231 itself. A portion of the PCB is exposed from the overmould 251 to form the electrical connector 245 to couple the higher power section of the PCB to the main power board 263a. In the form shown, the electrical connector 245 comprises a male tab of the PCB that is configured to engage in a complementary female socket of the main power board 263a. In an alternative connection, the electrical connector 245 comprises a female socket on the PCB that is configured to receive a complementary projecting tab of the main power board 263a. In either configuration, the entire higher power section of the PCB, other than the electrical connector 245, is advantageously encapsulated by, and pneumatically sealed by, the overmould 251.

The overmould also encapsulates electrical and/or electronics elements on the PCB.

The overmould 251 covers a section of the PCB 241 as well as the connection between the PCB 241 and the socket 231. The section of the PCB 241 that is covered is the section through which current flows from the main power board 263a to the socket 231. The remaining sections of the PCB 241 are used to provide current to the user interface via the display/interface PCB 263b, and do not require the same level of pneumatic sealing.

Therefore, another section of the PCB is exposed from the overmould. The section of the PCB that is exposed from the overmould is a lower power section of the PCB, whereas the higher power section of the PCB is substantially covered by the overmould. The lower power section of the PCB that is exposed from the overmould leads to the electrical connector 243. In the configuration shown, said electrical connector 243 is associated with a component having a lower power requirement than the main power board 263a. For example, the display interface PCB 263b that is associated with the display has a lower power requirement than the main power board 263a. Due to the lower power requirement, the portion of the PCB that leads to the electrical connector 243 does not need to be pneumatically sealed.

In an alternative configuration, the portion of the PCB that leads to the electrical connector 243 may be covered by the overmould. In yet another alternative configuration, the entire PCB other than electrical connector(s) may be covered by the overmould.

By also sealing the connection between the socket 231 and the PCB 241, any oxygen enriched gas that leaks out around the socket 231 during use would be prevented from entering the socket 231 via gaps between the socket 231 and the PCB 241. This is important as the socket 231 could be providing a large amount of power to the removable elbow 171, as the elbow in turn supplies the power for heating the conduit 16.

Figure 32:
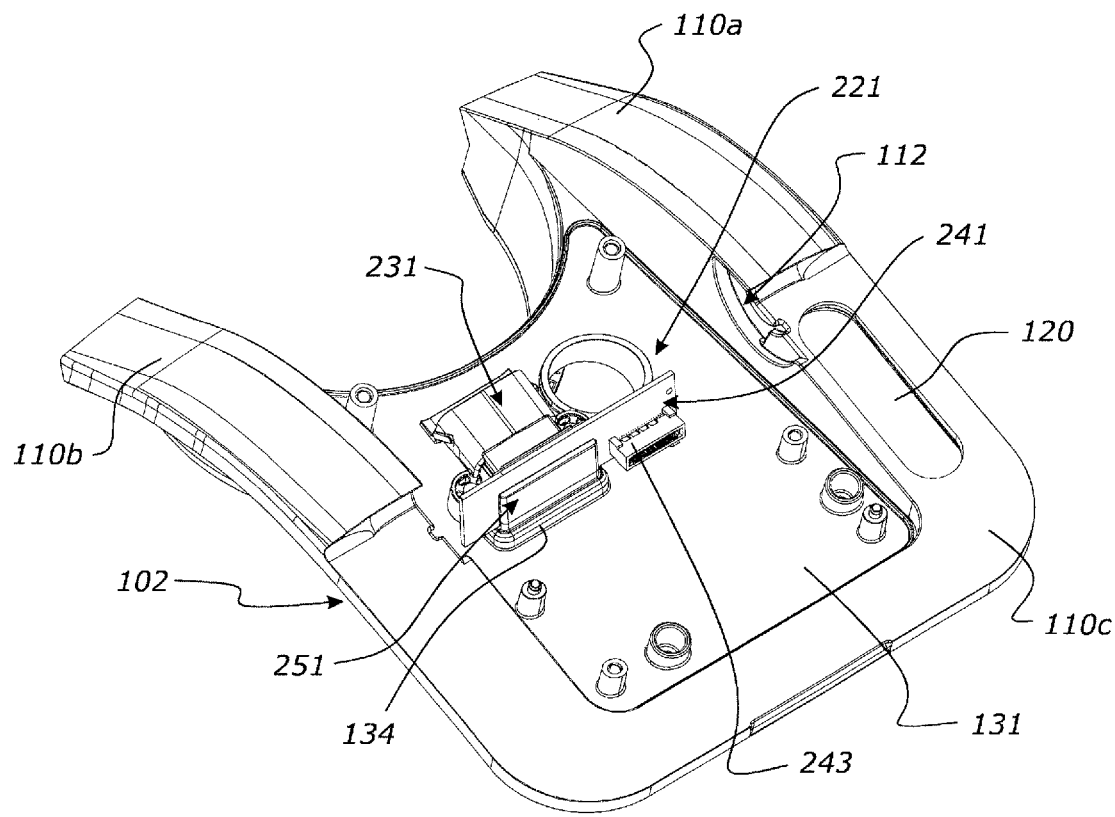
FIG. 32 is a rear/right side overhead perspective view showing the interconnecting assembly mounted to the upper chassis of the housing.

As shown in FIGS. 32 and 36, the overmould 251 on the PCB 241 can be configured such that it forms a tight fit with the aperture 134 in a wall of the upper chassis 102 of the housing. This serves to create a pneumatic seal between the PCB 241 and the aperture 134 in order to prevent ingress of moisture and gases into the interior of the housing 100, where the main power board 263a is located.

Referring to FIGS. 20 to 27, the housing of the base unit 50 of the apparatus 10 comprises a handle 261 connected to the upper chassis 102 of the housing 100. The handle 261 is movable between a lowered storage position shown in FIG. 23 and a raised carrying position shown in FIG. 24. In the raised carrying position, a user can use the handle to carry the apparatus 10.

When the handle 261 is in the lowered position, an upper surface of the handle 261 is substantially flush with upper forward wall portions 110a, 110b of the upper chassis 102 of the housing 100. A rearward peripheral upper wall portion 110c of the upper chassis forms a handle recess to receive the handle in the lowered position. An indent 102d (FIG. 20) is provided at a rear edge of the upper wall portion 110c to enable a user to insert their fingers under the handle to lift it from the lowered storage position.

Either side of the upper chassis 102 has an inwardly open connecting recess 112 for receipt of complementary connecting portions 263 of the handle. Although only the left side recess 112 is shown in the figures, the right side recess will be a mirror image thereof.

Figure 22:
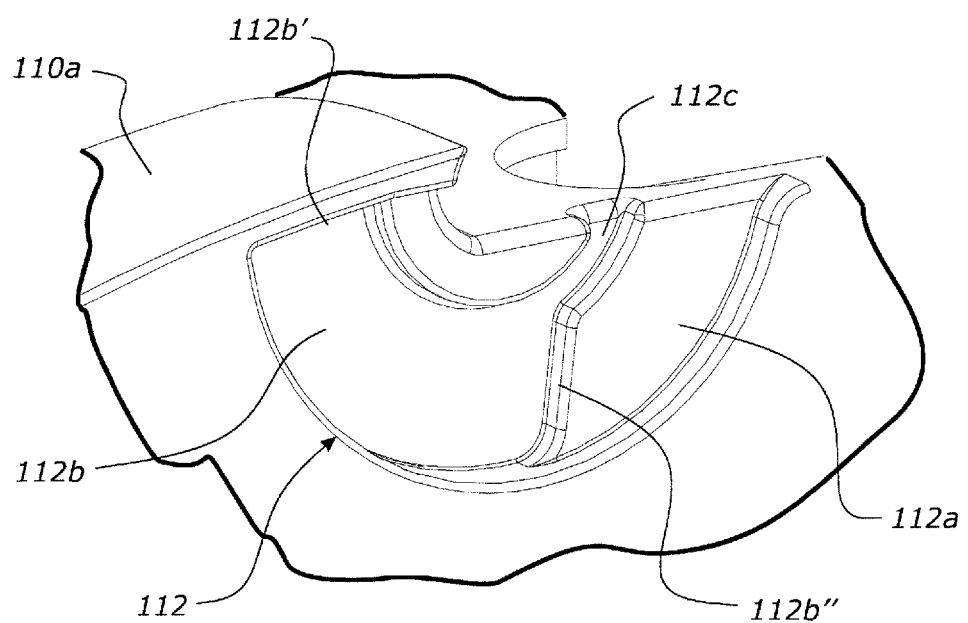
FIG. 22 shows part of the connection arrangement for receipt of the handle.

Referring to FIG. 22, the recess has a substantially half-circular configuration. The recess 112 has a transversely shallow rear portion 112a and a transversely deep forward portion 112b. An arcuate slot 112c extends upwardly and rearwardly from the transversely deep forward portion 112b and the upper end thereof is upwardly open.

The transversely deep forward portion 112b and the arcuate slot 112c define the boundary for the connecting features of the handle, thereby dictating the possible positions of the handle.

Figure 23:
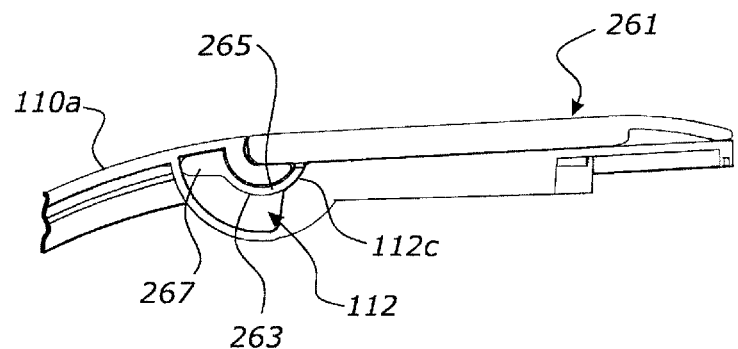
FIG. 23 is a right side view of the connection arrangement with the handle in a lowered position.
Figure 24:
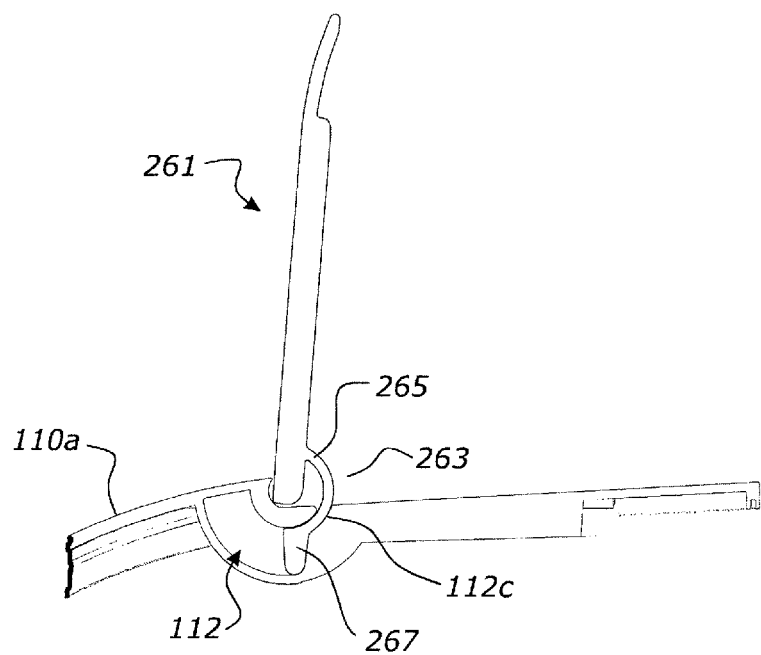
FIG. 24 is a right side view of the connection arrangement with the handle in a raised position.

FIGS. 23 and 24 show the connecting features on the connecting portion 263 of the handle. The connecting features comprise an arcuate arm 265 that extends from a position at or adjacent each end of the body of the handle. A distal end of the arm 265 is coupled to a tab 267 that projects forwardly and outwardly from the arm 265. The arcuate arm 265 and tab 267 project outwardly from a planar plate 264 (FIG. 27) that has an arcuate periphery. The planar plate 264 has dimensions corresponding to the dimensions of the transversely shallow rear portion 112a of the recess.

The connecting features 265, 267 of the handle 261 engage with the transversely deep forward portion 112b and arcuate slot 112c. The upper edge of the arcuate arm 263 forms a close fit with a semi-circular upper wall of the transversely deep forward portion 112b of the recess. Additionally, the arcuate slot 112c forms a close fit with upper and lower edges of the arcuate arm 263, so that the handle 261 follows the desired path of movement.

The tab 267 of the protrusion travels within the transversely deep forward portion 112b of the recess. The length of the tab 267 is configured to form a close fit with the upper and lower arcuate walls of the transversely deep forward portion 112b. When the handle 261 is lifted, the tab 267 rotates in the transversely deep forward portion 112b with respect to the housing 10, with the tab shifting between a forward boundary wall 112b' and a substantially vertical rear boundary wall 112b'' which is defined by the transversely shallow rear portion 112a of the recess. When the handle reaches an approximately vertical position as shown in FIG. 24, the tab 267 will contact the rear boundary wall 112b''', thereby limiting the movement of the handle 261.

Because the handle 261 connects to inner vertical walls of the upper chassis 102, the handle is prevented from being removed once the screen carrier 211 is attached to the upper chassis 102.

The handle 261 also includes an aperture 268 to accommodate a gas port 275 on a filter module 271, when the filter module is received in a filter recess 118 in the housing and when the handle is in a storage position. The aperture 268 is positioned along one side member of the handle, and is positioned closer to the transverse carrying portion 262 of the handle 261 that can be used to carry the apparatus 10, than it is to the connecting features 263-267 on that side member of the handle that movably connect the handle to the housing. The transverse carrying portion 262 extends from an end of the side member opposite to the end with the connecting features.

Figure 25:
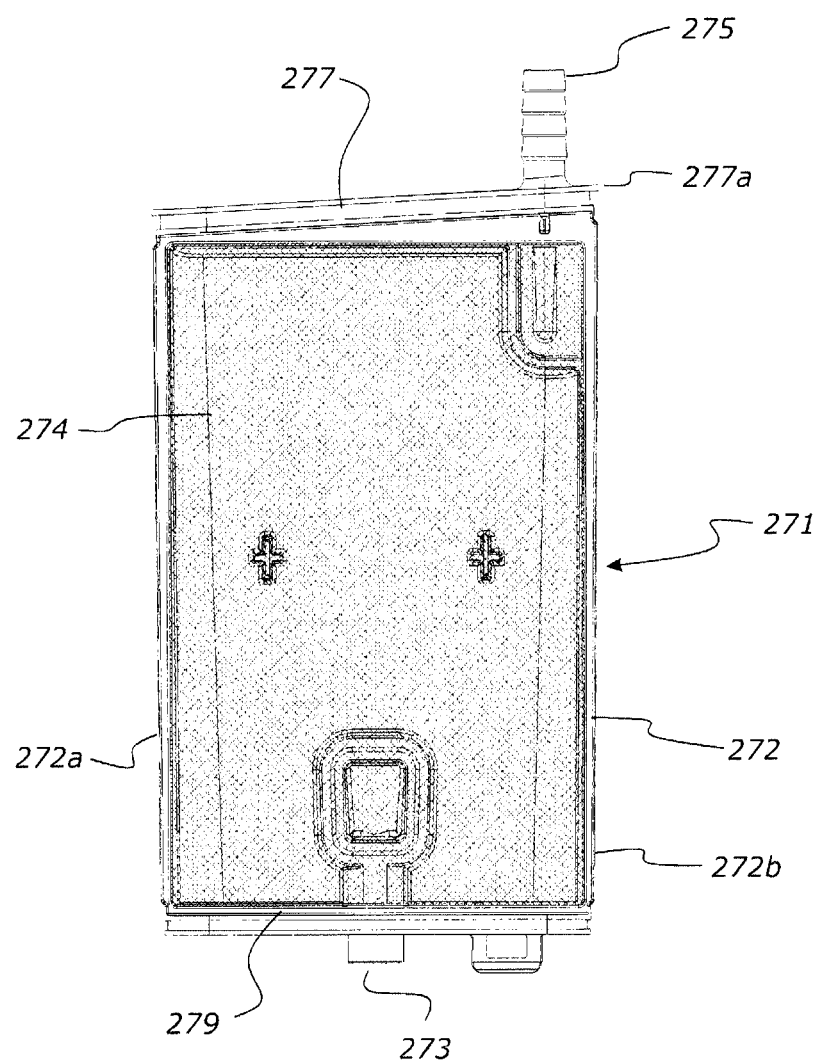
FIG. 25 is a right side view of a filter module.
Figure 26:
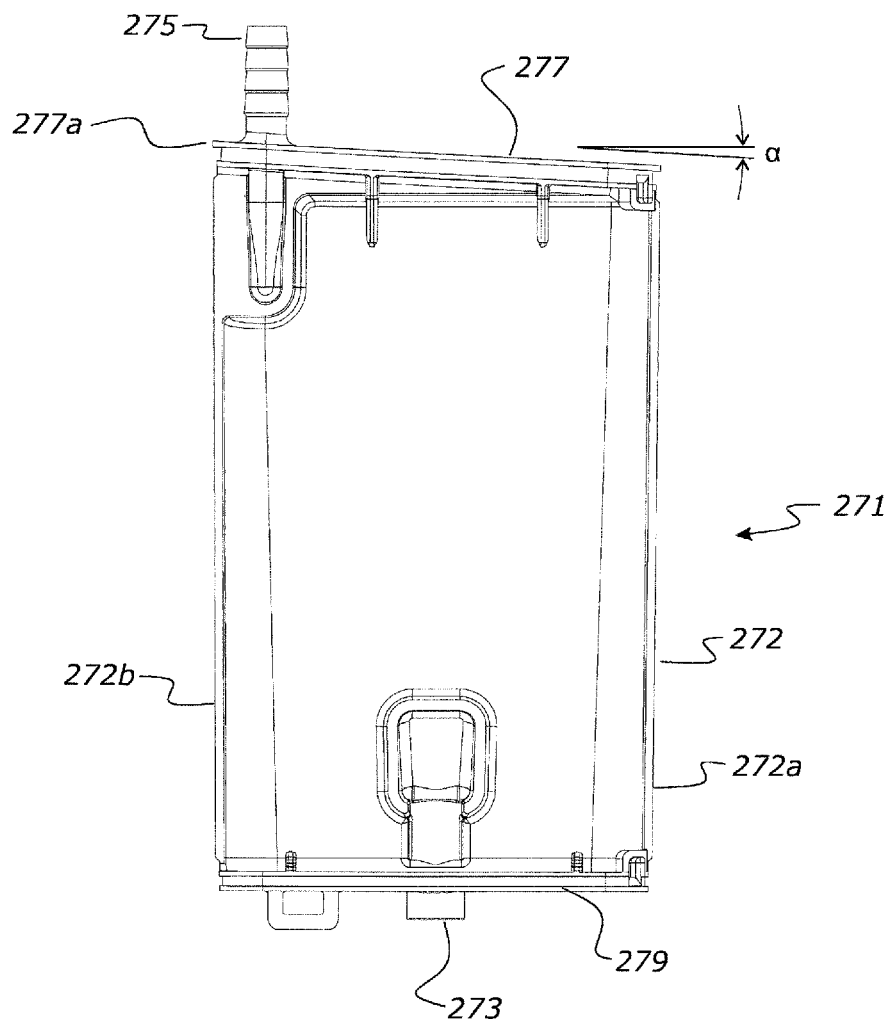
FIG. 26 is a left side view of the filter module.

The apparatus has a removable filter module 271 shown in FIGS. 25 and 26. Previous configurations of the filter module are described in WO2018/074935A1 (WO '935). Unless described below, the features and functioning of the filter module 271 are the same as the filter modules described in WO '935, and the contents of that specification are incorporated herein in their entirety by way of reference.

The filter module 271 has a filter body 272 having a plurality of walls including a first, front, upstanding wall 272a, an opposed second, rear, upstanding wall 272b, and upper wall 277 extending between the first wall 272a and the second wall 272b, and an opposite lower wall 279. The body 272 defines one or more filter chambers. A lower gas port 273 defines a first inlet at a base of the filter body and fluidly couples to an outlet port 307 of a valve module 301 (FIG. 40), to receive gases from the outlet port 307.

An upper gas port 275 defining a second inlet is provided at an upper end of the filter body 272 and extends upwardly from the upper wall 277. The upper gas port 275 is configured to interact with the aperture 268 in the handle. The upper gas port 275 can connect to a supplementary gas source. Ambient air inlets (not shown) are provided in the base of the filter body to allow for the entrainment of ambient air. These gases are then passed through a filter medium 274 of the filter 271 to filter gases as they exit the filter chamber(s) before being delivered to and mixed by the blower of the motor module.

The upper gas port 275 is in communication with at least one filter chamber, the lower gas port 273 is in communication with at least one filter chamber, and the ambient air inlets are in communication with at least one filter chamber. Two or more of the inlets may be in communication with the same filter chamber or with different filter chambers.

As shown in FIG. 37, the lower chassis 104 of the housing 100 has a filter recess 118 with a shape that is complementary to the shape of the body 272 of the filter module 271. An interior of the filter recess 118 is in communication with an interior of the recess 122 for receipt of the motor module, to enable the delivery of gases from the filter to the motor module.

Figure 20:
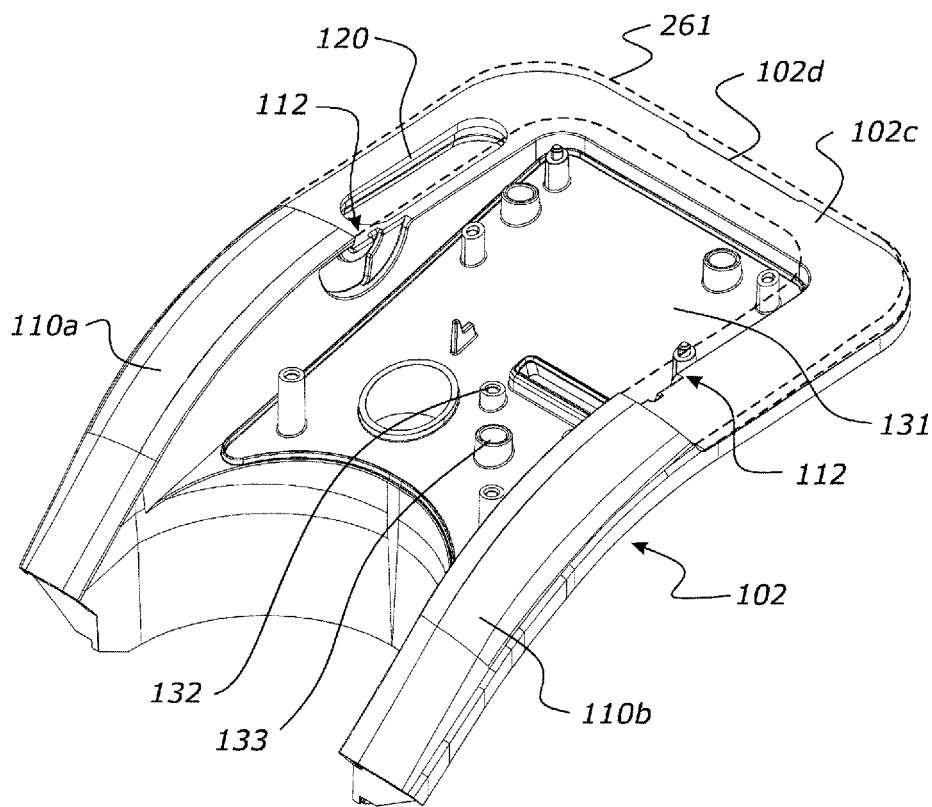
FIG. 20 is a front/right side perspective view of the upper chassis of the housing with a handle.
Figure 21:
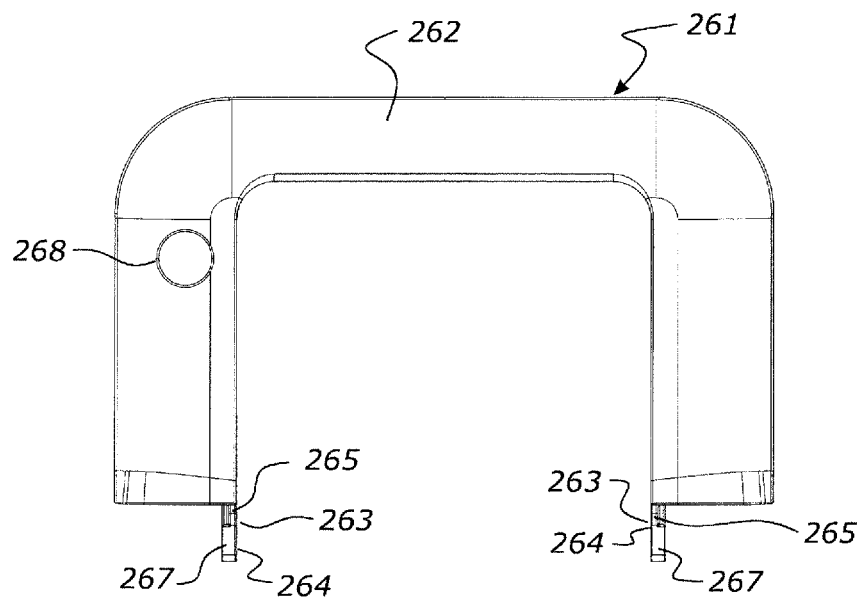
FIG. 21 is a top plan view of the handle.

Referring to FIGS. 20 and 32, a filter recess 120 is provided in the upper wall portion 110c of the upper chassis 102, and has a shape that is complementary to the shape of the upper portion of the body 272 of the filter module. The recess 120 is positioned above the recess 118 when the upper chassis 102 is coupled to the lower chassis 104.

As shown in FIGS. 25 and 26, the upper wall 277 of the filter body 272 is angled so as to be non-parallel to the lower wall 279 of the filter body. The angle α of the upper wall may be between about 2 degrees and about 10 degrees, optionally between about 2 degrees and about 5 degrees, optionally about 3 degrees, relative to the lower wall. Therefore, the second wall 272b is taller than the first wall 272a. That is, the upper wall 277 is offset from horizontal when the filter module 271 is installed in the housing 100, and is angled to match the upper surface 110c of the upper chassis 102 of the housing 100. In an alternative configuration, the upper wall 277 is parallel to the lower wall 279.

The upper gas port 275 is positioned closer to one of the first wall 272a and second wall 272b than it is to a centre of the upper wall 277. In particular, the upper gas port 275 is positioned at or adjacent the second wall 272b at one side of the filter body 272, and in the form shown is positioned at or adjacent the higher end 277a of the upper surface 277. This has a number of advantages, which can be explained with reference to the handle 261 and housing 100.

Firstly, by placing the upper gas port 275 at or adjacent one side of the filter body, the second inlet 275 only aligns with the aperture 268 in the handle 261 when the filter 271 is inserted in the correct orientation. If the filter were inserted backwards, the second inlet 275 would prevent the handle 261 from lying flat, indicating to a user that the filter is inserted incorrectly.

Secondly, the upper gas port 275 is located further from the axis of rotation of the handle 261. This results in a larger radius of curvature in the path the aperture 268 takes when the handle is moved 261. This is beneficial when a tube is connected to the upper gas port 275, as the handle 261 is less likely to get caught on the tube due to the aperture 268 moving in a smoother path. The end of the tube could have one or more flanges, which could be a location for the aperture 268 to catch on. With the large radius of curvature of the path of the aperture 268, the aperture 268 will be travelling substantially vertically as it passes over the flange(s) on the end of the tube. If the radius of curvature was smaller, the aperture 268 would be travelling at more of an angle as it passes over the flange(s), meaning the aperture 268 would be more likely to catch on the flange(s) of the tube.

Thirdly, as the upper gas port 275 is located further from the axis of rotation of the handle 261, the upper gas port 275 is also located further from the handle 261 when the handle is lifted. This is beneficial, as the user may use the upper gas port 275 to pull on the filter when removing it from the housing 100, and the increased distance between the upper gas port 275 and the handle 261 gives the user more room to grip the second inlet. The filter module 271 may have a grip feature at or near its upper surface for a user to grip to remove the filter from the housing 100.

It will be appreciated that these benefits can also be obtained with a filter that only has the upper gas port 275 and that doesn't also have the lower gas port 273 or the ambient air inlets.

While the filter module 271 is shown as being on the left side of the housing 100, it could instead be installed in filter recesses on the right side of the housing. In that configuration, the right side member of the handle 261 would have the aperture 268. Alternatively, both sides of the housing could have filter recesses for receipt of respective filter modules 271, with both sides of the handle 261 having the apertures 268.

The handle 261 is pivotally mounted to the housing 100 by a forward end of the handle, and the filter module 271 is installed in the housing so that the side of the filter having the upper gas port 275 is positioned rearwardly on the filter module. Alternatively, a rear end of the handle 261 could be pivotally mounted to the housing 100 (so that the transverse carrying portion 262 is positioned toward the front of the housing 100 rather than towards the rear of the housing), and the filter module 271 could be installed in the housing so that the side of the filter having the upper gas port 275 is positioned forwardly on the filter module.

As described above, the filter module 271 is removable and may be removed by pulling on the upper gas port 275, or alternatively on a grip feature. The housing may comprise a push button or a release latch. FIG. 3 shows a release latch in the form of a filter release tab 276. The filter release tab 276 comprises a pivoting member that pushes the filter module 271 away from the housing. In the form shown, the filter release tab 276 pushes the filter module 271 upwardly and outwardly. Alternatively, the push button may dislodge the filter module 271 from a secured position such that the filter module 271 can be pulled out by hand. An alternative method of removing the filter module 271 is by using a filter removal tool 280, which is shown in FIGS. 57 and 58.

The filter removal tool 280 comprises an engagement portion 281 and a gripping portion 282. The engagement portion 281 is generally cylindrical and comprises an internal recess 283 that corresponds to, and receives, the upper gas port 275. The internal recess 283 is shaped to match a standard medical taper, such as the shape of the upper gas port 275. The internal recess 283 may have a smooth surface as shown in FIG. 57. Alternatively, the internal recess may comprise one or more engagement features for engaging with features on the filter portion 275. For example, the inner surface of the internal recess 283 may comprise one or more ridges or one or more annular recesses located on an inner surface of the engagement portion 281, adjacent the recess defined by the terminal lip of the engagement portion.

Figure 57:
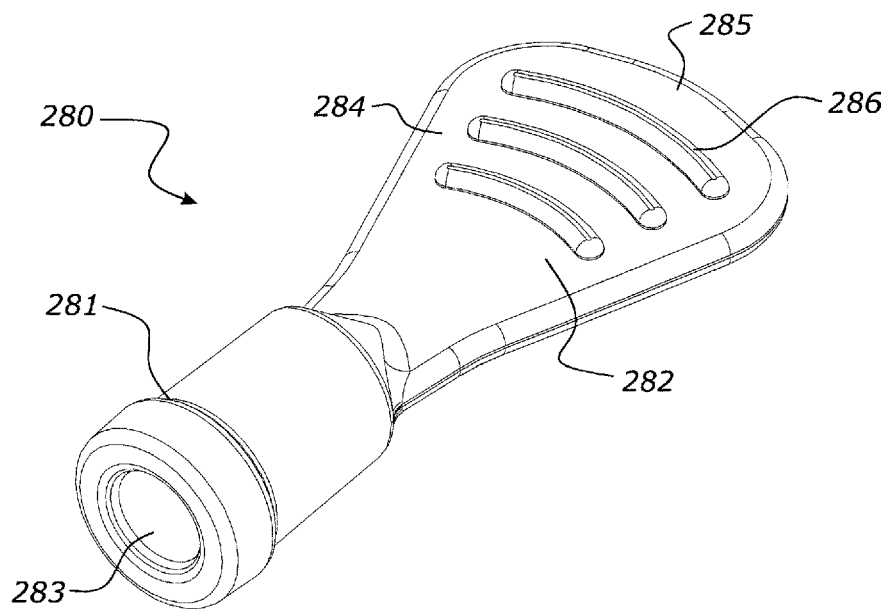
FIG. 57 is a perspective view of a filter removal tool.
Figure 58:
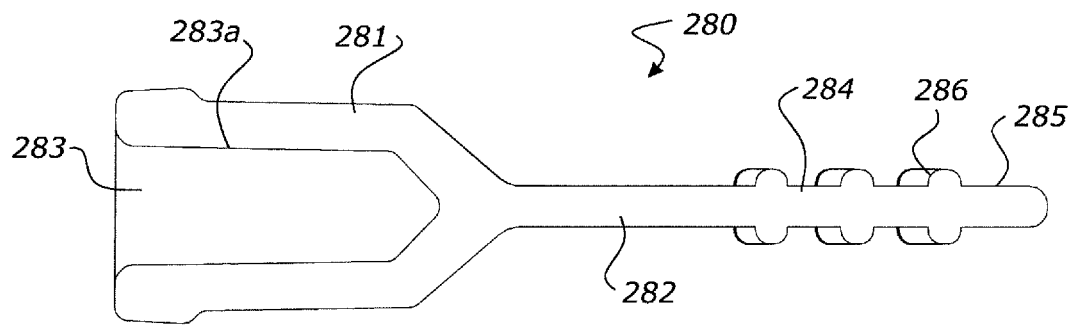
FIG. 58 is a cross-sectional view of the filter removal tool of FIG. 57.

FIG. 57 shows the gripping portion 282 comprises a tab 284 having an expanded flat region 285. The flat region 285 is configured to be manually gripped by a user, for example between the user's thumb and index finger. The expanded flat region 285 may also comprise a textured surface and/or one or more protrusions 286 configured to aid the user in gripping the filter removal tool 280.

In use, the user would initially press the filter removal tool 280 onto the upper gas port 275, such that the upper gas port 275 engages with the internal recess 283 of the engagement portion 281. In order to create a tighter fit between the internal recess 283 and the upper gas port 275, the user can twist the filter removal tool 280 relative to the upper gas port 275 as they press the tool 280 onto the upper gas port 275, an action which is made possible by the width of the tab 284. Once the filter removal tool 280 is engaged with the upper gas port 275, the user can press on the filter release tab 276 (FIG. 3) located on the side of the base unit 50. That will allow the filter to move relative to the main housing 100 of the base unit 50. The user can then proceed to pull the filter removal tool 280 away from the main housing 100 of the base unit 50, which will in turn pull the filter module 271 away from the main housing 100 of the base unit 50. If the user attempts to pull out the filter module 271 using the filter removal tool 280 without first pressing on the filter release tab, then the filter removal tool 280 will simply disengage from the upper gas port 275 without damaging the filter module 271 or the filter removal tool 280.

If the filter removal tool 280 has internal ridges or recesses, twisting the filter removal tool 280 may cause the internal ridges or recesses to engage with the corresponding ridges or recesses on the upper gas port 275 of the filter module 271. The engagement of the various ridges or recesses causes the tool to grip on to the upper port of the filter module 271 thereby making removal of the filter module 271 easier.

Once the filter module 271 is removed, the user can discard the filter removal tool 280 along with the filter module 271, and then proceed to insert a new filter module 271 into the device. As the filter removal tool 280 may be discarded along with the filter module 271, the filter removal tool 280 may comprise a bio-sourced and/or bio-degradable plastic in order to reduce waste. Alternatively, the filter removal tool may be made of a recyclable plastic.

The filter removal tool 280 is useful in situations in which the upper gas port 275 may be too small or awkward for some users to be grip well, thereby making it difficult to pull the filter module 271 out. Additionally, the filter removal tool 280 will only need to be assembled with the filter module 271 when the tool 280 is being used to remove the filter module 271—there is no need for the tool 280, or any similar other component, to protrude from the main housing 100 of the base unit 50 when not in use.

A filter removal tool 280 may be packaged with each filter module 271. The filter removal tool 280 may be placed in the same packaging as the filter module 271. Alternatively, the filter removal tool 280 may be positioned in a sealed packaging that is provided with or within the packaging of the filter module 271. The filter removal tool 280 being sealed from the filter module 271 reduces the chances of contamination of the filter module 271 prior to the filter module 271 packaging being opened.

Figure 40:
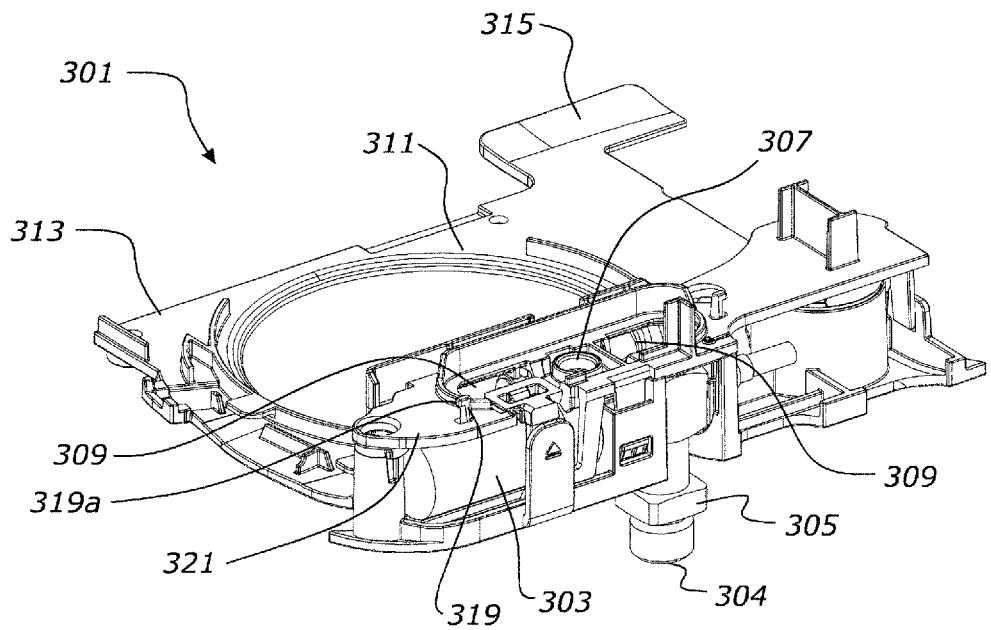
FIG. 40 is a rear/left side overhead perspective view of a valve module and valve housing.

The breathing assistance apparatus has a valve module 301 shown in FIG. 40. The valve module 301 controls the flow of oxygen and/or other gases entering the gas flow path of the apparatus 10, and enables the apparatus 10 to regulate the proportion of oxygen entrained in the airflow. The valve module 301 is formed as a modular component for ease of manufacture, assembly, servicing, or replacement, for example in the event of malfunction, routine maintenance, or future upgrade/improvement.

The valve module 301 is engaged with the main housing 100 of the base unit 50 of the apparatus, such that the valve module 301 is substantially received in the housing and is accessible from the exterior of the housing. The valve module 301 may be removable from the housing 100, or may not be removable. Part of the valve module 301 is arranged to be substantially flush with an external wall of the housing, for example the bottom wall 115 of the lower chassis 104, when the valve module is engaged with the housing. The valve module 301 comprises a flow control valve 303 that is arranged to control a flow of gas through a valve manifold. The valve 303 is arranged to control a flow of gas into part of the apparatus. For example, the valve 303 may be arranged to control a flow of gas to the filter module 271. Alternatively, the valve 301 may be arranged to control a flow of gas to another part of the apparatus 10. The valve module 301 and filter module 271 are positioned upstream of the blower of the motor module.

The valve 303 receives gases from an inlet port 304 which, in the form shown, is embodied in a swivel connector 305. The valve 303 delivers gases to an outlet port 307. The outlet port 307 is configured to fluidly couple to the first inlet 273 of the filter module 271.

The valve module 301 also comprises ambient air ports 309 to enable ambient air to be delivered to the ambient air inlets of the filter module 271.

A previous configuration of the valve module is described in WO2018/074935A1 (WO '935). Unless described otherwise herein, the features and functioning of the valve module 301 are the same as the valve module described in WO '935, and the contents of that specification are incorporated herein in their entirety by way of reference.

The valve module 301 is in electrical communication with the main power board 263*a* of the apparatus 10, to allow the apparatus 10 to power and/or communicate with the valve module 301. In WO '935, the lower chassis had a valve recess for receiving a valve module, and a battery recess for receiving the battery cover. These two recesses were separated by a wall, with a gap being provided in the wall to allow wires (or alternatively a flexible PCB) to pass from the valve module, through the battery recess, and then connect with the power board. In order to help prevent oxygen leaking from the valve recess into the battery recess, a grommet was located at the gap, with the flexible PCB being passed through the grommet.

Figure 38:
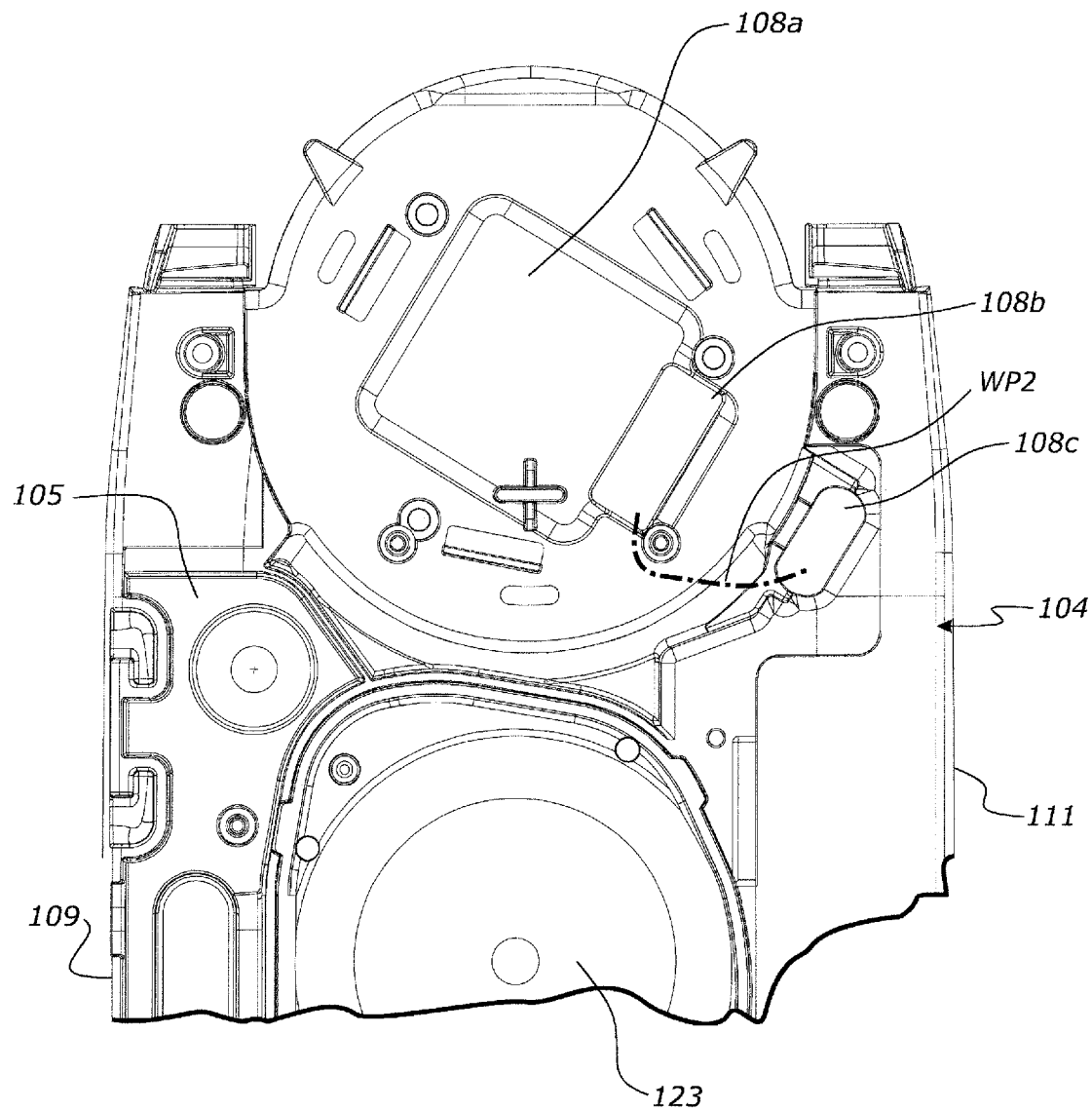
FIG. 38 is a bottom view of a front portion of the lower chassis.
Figure 39:
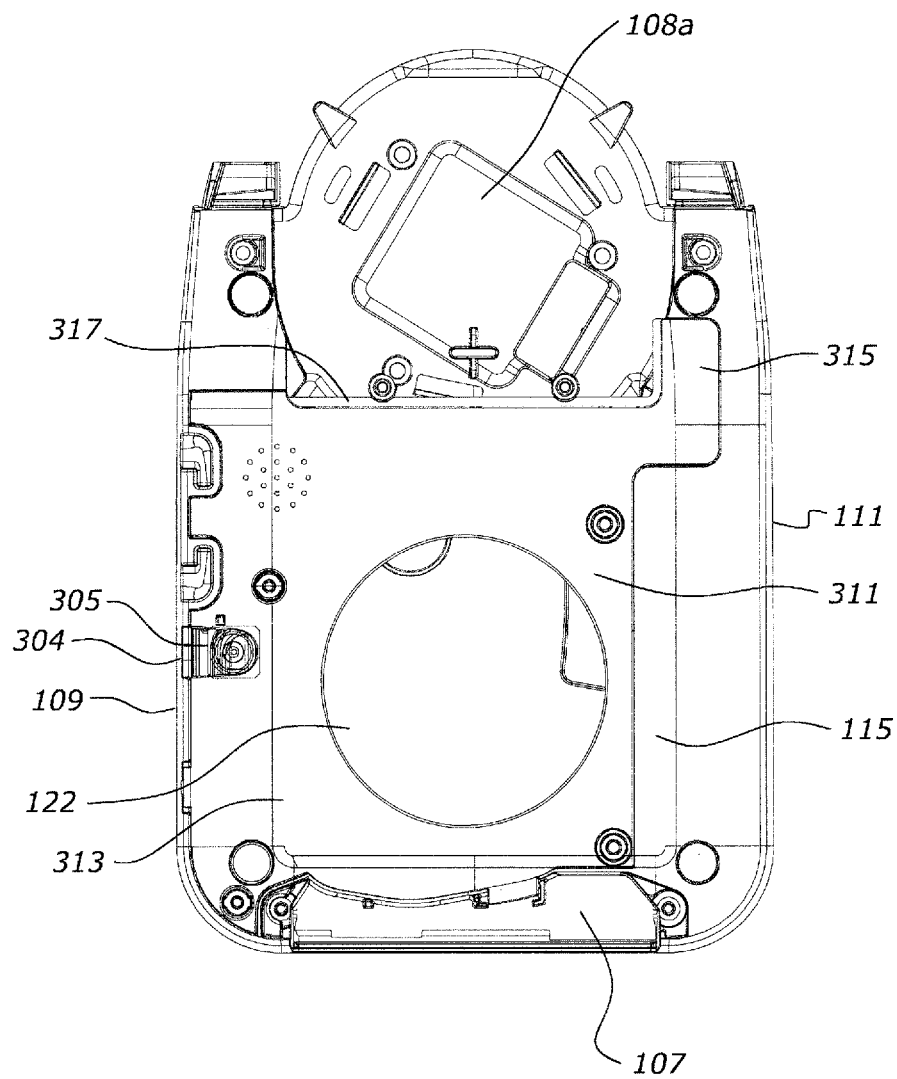
FIG. 39 is a bottom view of the lower chassis with a valve housing in place.

Referring to FIGS. 37 to 39, in the present configuration, the lower chassis 104 of the housing 100 comprises a valve recess 105 in its underside for receipt of the valve module 301 and a battery recess 107 in its rear side for receipt of the battery module 125. The wires from the valve module 301 do not pass directly from the valve recess 105 into the battery recess 107. Instead, the wires now pass from the valve recess 105 to the recess 122 for the motor module, and then from the recess 122 for the motor module to the battery recess 107. This offers a number of advantages. The wiring path WP1 is shown schematically by a broken line in FIG. 37.

Firstly, any oxygen that leaks from the valve module 301 should be prevented from flowing into the battery recess 107, as the battery recess contains a number of electrical connections, including the electrical connectors for the main power board 263*a*. By using the proposed routing WP1 for the wires, the wall between the valve recess 105 and the battery recess 107 can be left intact and impermeable to gas flow. In order for oxygen to get into the battery recess 107, it would need to flow into the motor module recess 122 first, and then from the motor module recess 122 into the battery recess 107. Due to the motor module recess 122 being unsealed, the oxygen in this scenario would disperse out of the apparatus from the motor module recess 122, with only an insignificant amount of oxygen at most continuing into the battery recess 107.

Secondly, as there is no gap in the wall between the valve recess 105 and the battery recess 107, the aforementioned grommet is no longer required. This reduces the number of components and simplifies manufacturing.

Another change to the valve module 301 comes as a result of changes to the wiring for the heater plate 141. In the previous configuration shown in FIG. 162 of WO2016/207838A9, the heater plate would connect to the upper chassis, with the wiring for the heater plate passing through a first gap in the upper chassis. After passing through this gap the wiring would be located between the upper and lower chassis (i.e. inside the housing) and connected to the power board.

In the present configuration, the heater plate 140 instead connects to the lower chassis 104. This is beneficial, as any liquid that spills around the heater plate 140 can drain through gaps in the lower housing and out underneath the housing 100, without having any chance of pooling between the upper chassis 102 and lower chassis 104.

As shown schematically in FIG. 38, wiring from the heater plate 140 exits the lower portion 108*a* of the liquid chamber recess 108, out through gap 108*b*, along the underside of the base wall beneath the recess 108, and back into the lower chassis 104 through a second gap 108*c*. The wiring path WP2 is shown schematically in FIG. 38. The second gap 108*c* provides an entrance for the wiring path into an internal area of the housing 100.

In order to prevent the wiring being exposed to an exterior of the apparatus 10 between the first gap 108*b* and the second gap 108*c*, a cover is provided over this section of the base of the lower chassis 104. Similarly, between leaving the valve recess 105 and entering the battery recess 107, the wiring running along the wiring path WP1 from the valve module 301 would also be exposed if it were not also provided with a cover.

The cover for these two sections is provided by a base housing member 311 of the valve module 301, as shown in FIG. 39. This enables the two sections to be covered without adding extra components to the housing 100. A main body portion 313 of the base housing member 311 provides the cover for a wiring path WP1. A forwardly and laterally extending finger portion 315 of the base housing member 311 provides the cover for the wiring path WP2. The main body portion 313 completely surrounds the edge of the base 123 of the motor module (not shown in FIG. 39), thereby better securing the motor module in the housing 100, such that it cannot be removed, unless the valve module is 301 is removable from the housing and is removed first. Additionally, the size of the base housing member 311 allows multiple fasteners to be used to fasten the valve module 301 to the lower chassis 104 of the housing, thereby better securing the valve module 301 to the housing 100.

The base housing member 311 has an overlap region 317, which is designed to overlap with the rear edge of a base of the guard 160. During assembly, the valve module 301 would be coupled with the lower chassis 104, with the guard 160 being coupled to the lower chassis 104 after that. The guard 160 would then overlap the base housing member 311 of the valve module 301, and prevent the valve module 301 from being removed without first removing the guard 160 from the housing. As the valve housing prevents the motor module from being removed, this also means that the guard 160 also indirectly prevents the motor module from being removed.

As shown in FIG. 40, the valve module 301 also has a post 319 extending upwardly from a portion of the valve housing, and in the form shown from a cover plate 321 above the valve 303. During assembly, the wires/flexible PCB from the valve module 301 would be wrapped around the post 319. Once wrapped around the post 319, any tensile force applied to the wires would cause the wires to tighten around the post, instead of becoming dislodged from the valve module 301. The post may also have a hooked end 319a in the form of a lateral or perpendicular protrusion at end of the post. This helps prevent the wires from sliding off the post 319.

Figure 41:
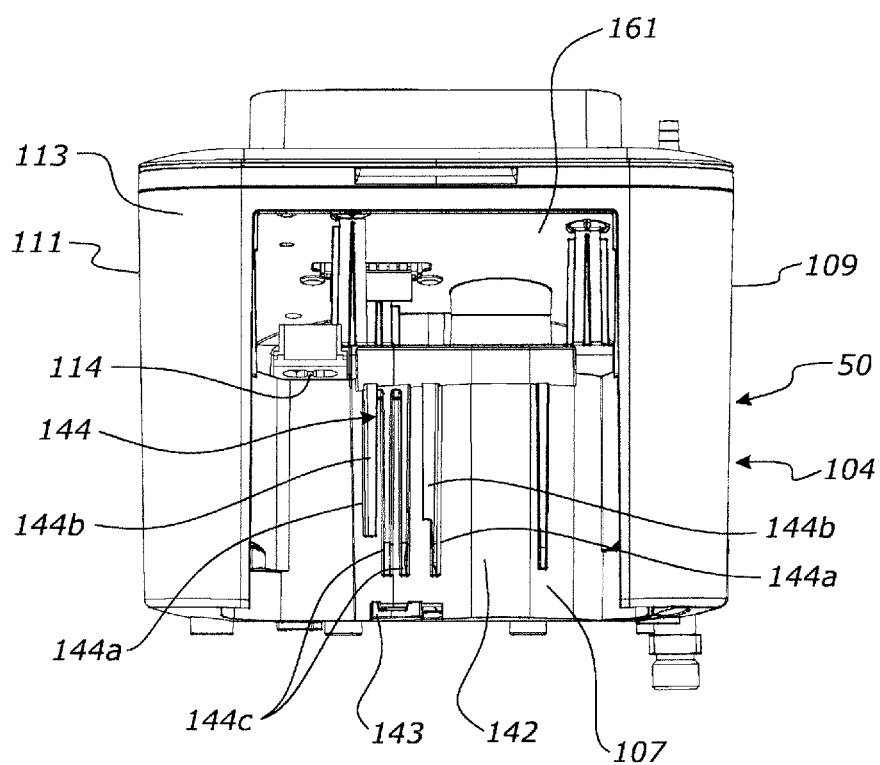
FIG. 41 is a rear view of the breathing assistance apparatus base unit showing features of the battery recess.
Figure 42:
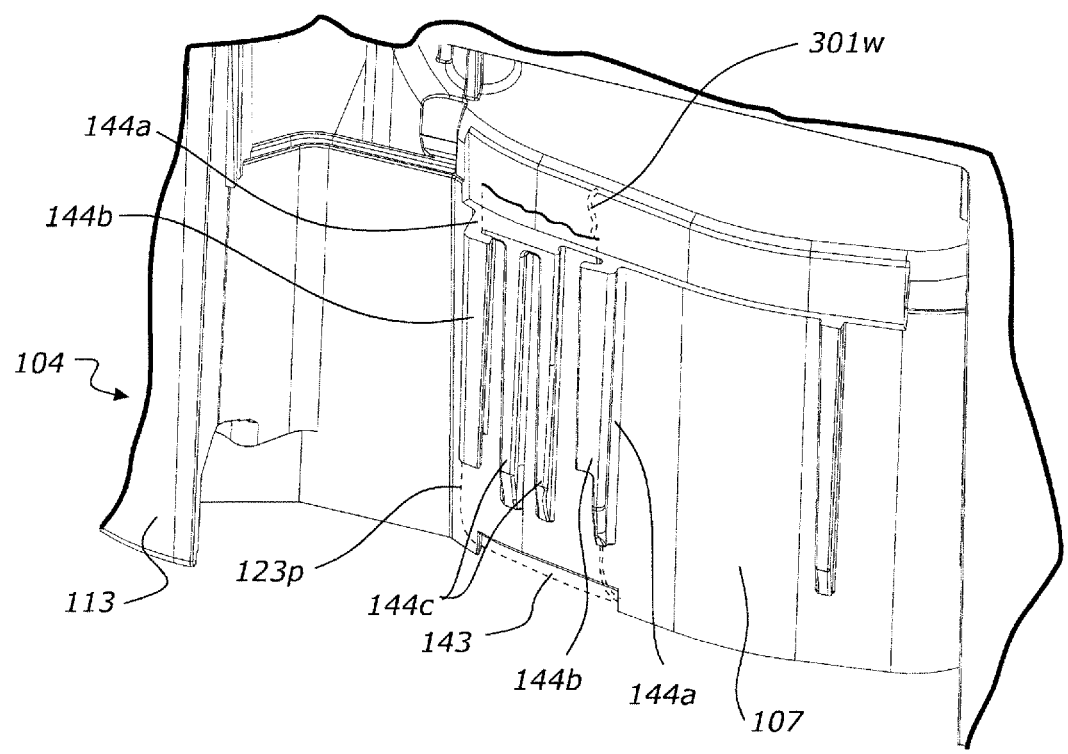
FIG. 42 is a rear perspective view of the battery recess features.

Referring to FIGS. 41 and 42, the lower chassis 104 has a battery recess 107, with a wall 142 separating the battery recess 107 from the recess 122 for receipt of the motor module. This wall has a gap 143 adjacent its bottom edge to allow wires 301w (shown in broken lines in FIG. 42) from the valve module 301 to pass between the two recesses. The wires 301w are used to provide power and/or communication to the valve module 301. Similarly, a flexible PCB 123p (shown in broken lines in FIG. 42) is used to provide power and/or communication to the motor module, and can also pass through this gap 143. Both the flexible PCB for the motor module and the wires for the valve module 301 run vertically through the battery recess 107 along the rear surface of the wall 142 of the lower chassis 104 in order to connect with the main power board 161.

The rear surface of the wall 142 of the lower chassis 104 has retaining features 144 designed to retain the flexible PCB. The retaining features are oriented substantially vertically and are positioned above the gap 143. The retaining features have two spaced apart ribs 144a that extend from the rear surface of the wall 142 of the lower chassis 104, with inwardly facing protrusions 144b extending from the terminal edges of the ribs 144a. The distance between the ribs 144a is configured to be complementary with the width of the flexible PCB 123p. The distance between the protrusions 144b is smaller than the width of the flexible PCB 123p. Once assembled, the flexible PCB 123p would sit between the ribs 144a with the protrusions 144b retaining the flexible PCB in the desired position between the protrusions 144b and the wall 142.

The wires 301w for the valve module 301 can also run between the ribs 144a of the retaining features. The wires 301 would be placed between the flexible PCB 123p and the rear surface of the wall 142, such that the retaining features 144 retain the flexible PCB 123p, with the flexible PCB retaining the wiring 301w. The rear surface of the wall 142 of the lower chassis 104 can additionally have one or more grooves to further aid in retaining the wiring in the desired position.

Also located between the ribs 144a are one or more supports 144c extending from the wall 142 to support the flexible PCB. The supports 144c are positioned between the ribs 144a and have a forward-rearward depth smaller than that of the ribs 144a. The supports 144c support the flexible PCB 123p at the correct distance from the rear surface of the wall 142 to ensure the protrusions 144b of the ribs 144a contact the flexible PCB.

Additionally, the side(s) of the supports 144c form(s) a boundary for the track for the wires. As such, the track can be bounded on four sides during use by the rear surface of the wall 142, one of the ribs 144a of the retaining features, one side of one of the supports 144c, and the flexible PCB 123p. Alternatively, the track can be bounded on four sides during use by the rear surface of the wall 142, sides of two of the supports 144c (if a gap is provided between the upper ends of the two supports 144c), and the flexible PCB 123p. The depth of the supports 144c, as well as the distance between the support 144c and the rib 144a are configured to create a cross-sectional area that is complementary to the wires, such that the wires are tightly packed within the track once the apparatus is fully assembled.

In an alternative configuration, the flexible PCB 123p could be used for connecting the valve module 301 to the main power board 161, with the wires 301w then used for connecting the motor module to the main power board 161. In a further alternative configuration, the motor module and the valve module 301 could both have a flexible PCB, with the flexible PCBs being stacked together between the retaining features 144. The track for receipt of wires would not be required in this configuration.

The gap 143 is advantageously positioned directly vertically below the base of the retaining features 144, so that that flexible PCB and wires can extend directly vertically upwardly from the gap 143, through the retaining features 144, and to the main power board 161 so as to not kink the flexible PCB and wires.

Figure 43:
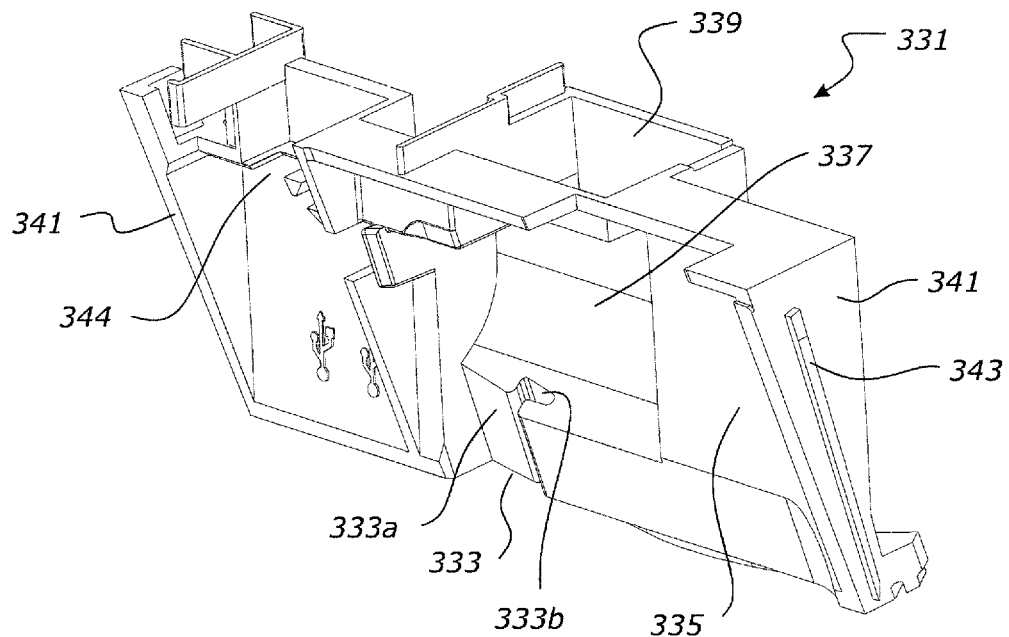
FIG. 43 is an overhead perspective view of a receptacle for receipt of electrical connectors.
Figure 44:
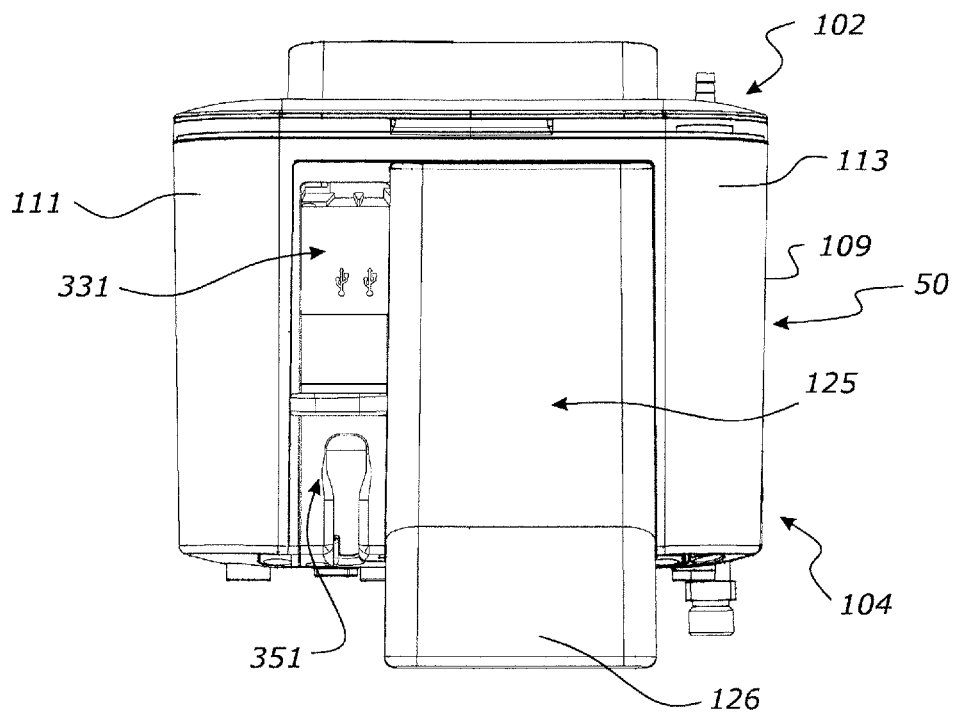
FIG. 44 is a rear view of the breathing assistance apparatus base unit with the battery module in place.
Figure 45:
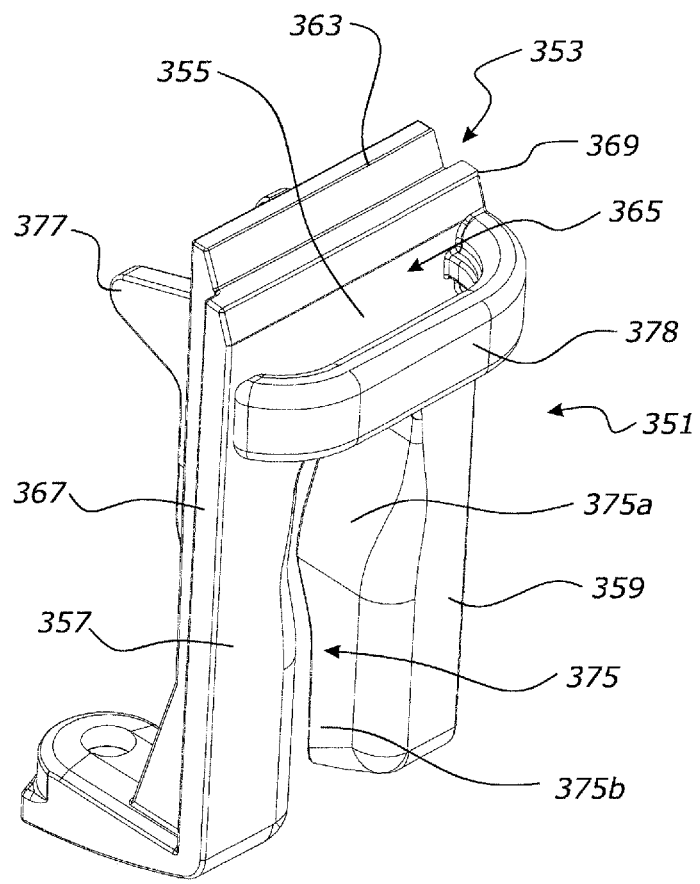
FIG. 45 is a rear/right side overhead perspective view of a power cord retainer.
Figure 46:
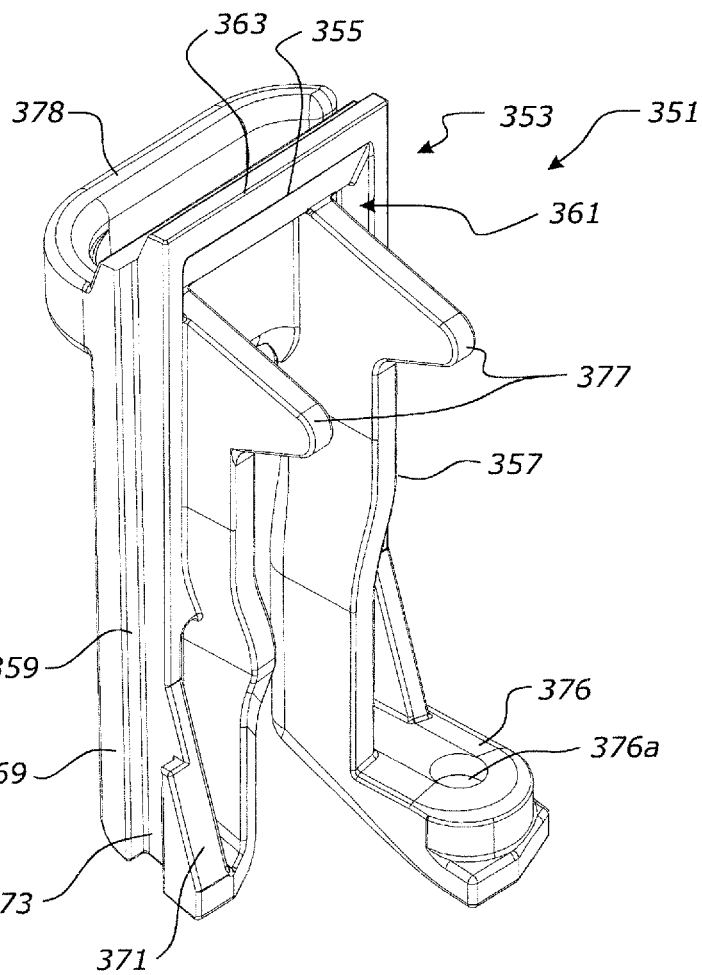
FIG. 46 is a front/left side perspective view of the power cord retainer.
Figure 47:
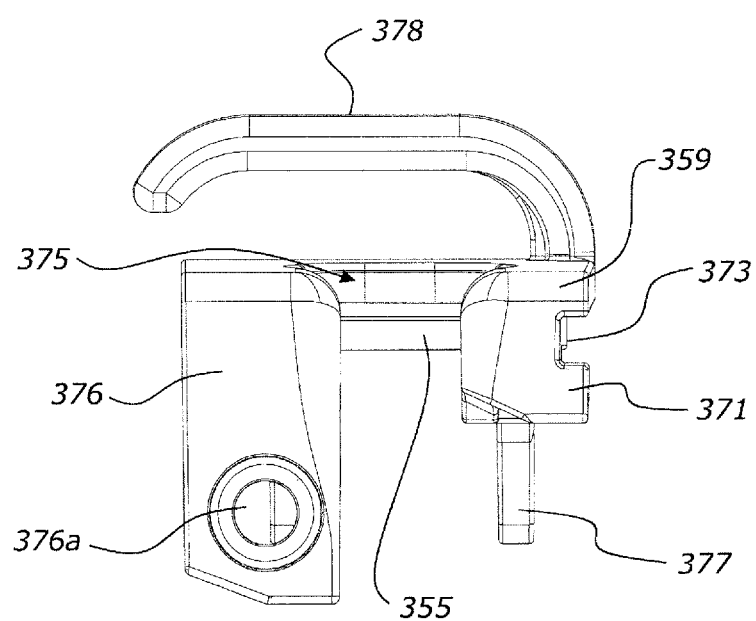
FIG. 47 is a bottom view of the power cord retainer.

The power panel 331 shown in FIG. 43 is located directly vertically above the retaining features 144. The power panel is retained between the upper chassis 102 and the lower chassis 104, and has multiple receptacles to allow the electrical connectors to extend through the power panel. The power panel 331 has a slot 333 extending into the bottom of a rear surface of a body portion 335 of the power panel 331.

The slot comprises a first enlarged region 333a configured for receipt of the flexible PCB 123p, and an auxiliary transversely extending smaller region 333b in the form of a hooked recess for receipt of the wires 301w. When assembled with the housing 100, the slot 333 is located above the retaining features 144. The upper end of the slot is in communication with a recessed portion 337 which extends to a receptacle 339 at an upper edge of the power panel 331. When assembled, the receptacle 339 contains electrical connectors for the main power board 263a that the flexible PCB and the wires will connect to. The flexible PCB and the wires extend from the retaining features 144, through the slot 333, and into a recessed portion 337 to couple with the main power board connectors in the receptacle 339.

The power panel 331 has two tapered side walls 341 with projecting retention features 343 in the form of elongate ribs. The retention features 343 are received in complementary grooves in the upper chassis part 102 and/or lower chassis part 104 to mount the power panel 331 to the housing 100.

During assembly, the rear surface of the wall 142 of the lower chassis 104 is exposed such that the flexible PCB and the wiring can easily be assembled with the retaining features 144 and connected to the connectors of the main power board 263a that are in the receptacle 339. Once this has been done, the battery module 125 can be connected, thereby covering the flexible PCB and the wiring. This protects the flexible PCB and the wiring, as well as helping to retain it in place.

The back walls 113, 142 of the housing form a close fit with the battery once the battery and battery cover 126 are assembled to the housing 100. This holds the battery in the correct position without requiring additional fasteners or adhesive. This makes assembly, maintenance, and repair more simple.

Referring to FIG. 41, an electrical socket 114 is provided in a recess in the back of the lower chassis 104, and is configured to connect a power cord to the main power board 263a to power the main power board 263a. The power cord removably connects to the electrical socket 114, such that if the power cord becomes damaged during use it can be replaced without having to perform any rewiring of the apparatus 10.

However, during typical use it would be desirable to prevent the power cord from being disconnected from the base unit 50 of the apparatus 10. Firstly, this would prevent the power cord from accidentally being disconnected such that the apparatus 10 loses mains power. Secondly, this prevents the power cord from being separated from the base unit 50 of the apparatus 10 and potentially being misplaced.

In order to prevent the power cord from being removed from the base unit of the apparatus 10, a power cord retainer 351 as shown in FIGS. 45 to 51 is used. In one configuration, the power cord retainer 351 connects to a battery cover 126 of the battery module 125, such that during assembly the power cord would be attached to the base unit 50 of the apparatus 10 after the battery cover 126, with the power cord retainer 351 being attached last. Alternatively, the power cord retainer 351 could be connected to a different part of the housing 100, such as directly to the lower chassis 104 for example.

Figure 48A:
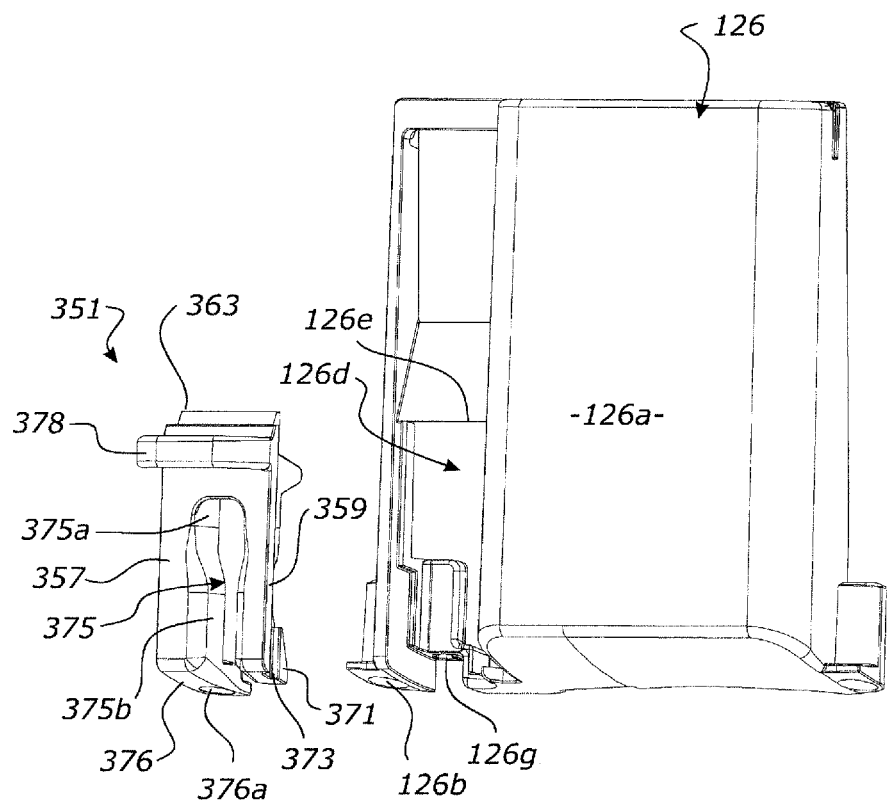
FIG. 48A is an exploded perspective view of the power cord retainer and battery cover of the battery module.
Figure 48B:
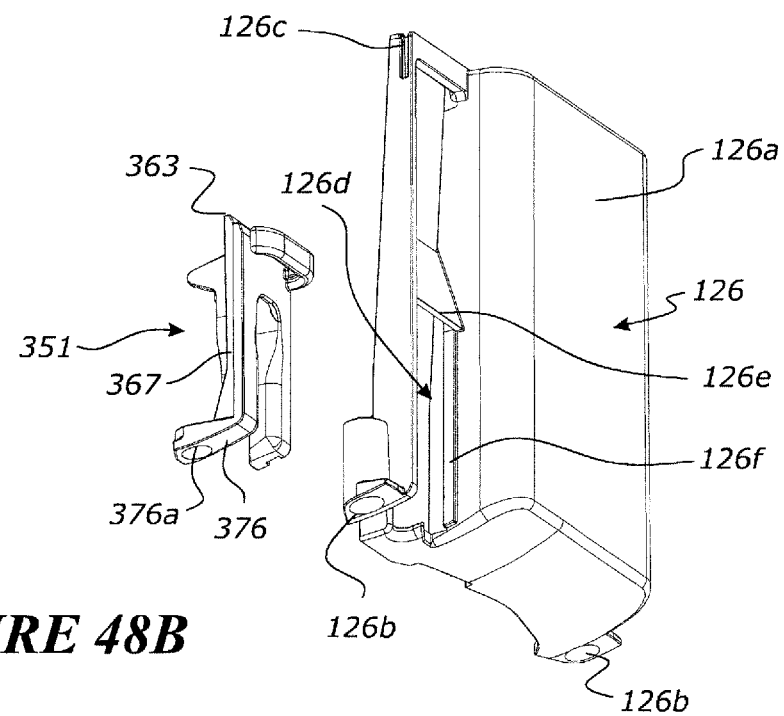
FIG. 48B is another exploded perspective view of the power cord retainer and battery cover.
Figure 49:
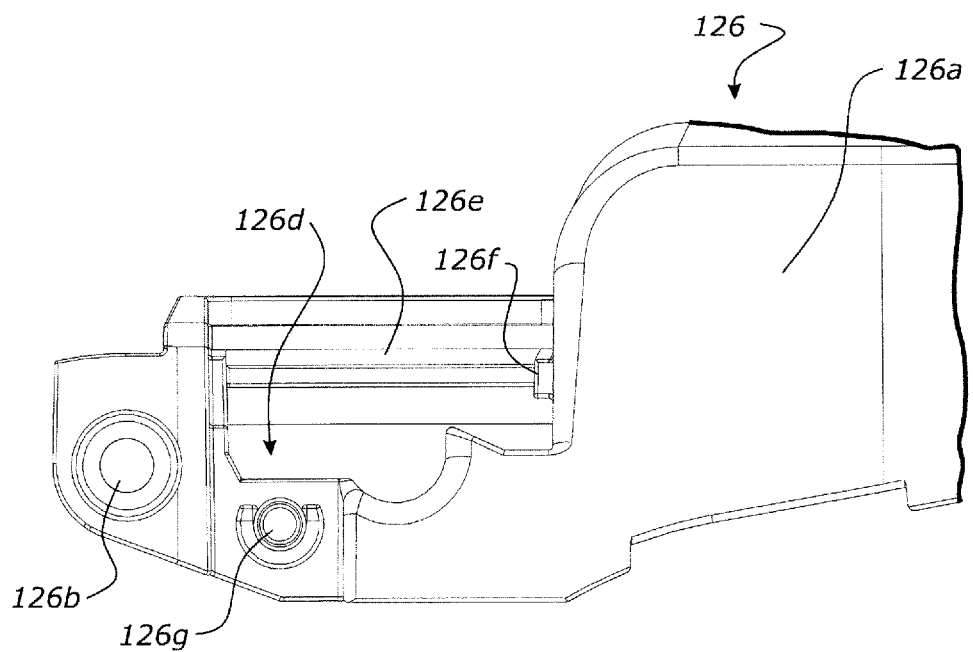
FIG. 49 is a bottom view of a part of the battery cover for receipt of the power cord retainer.
Figure 50:
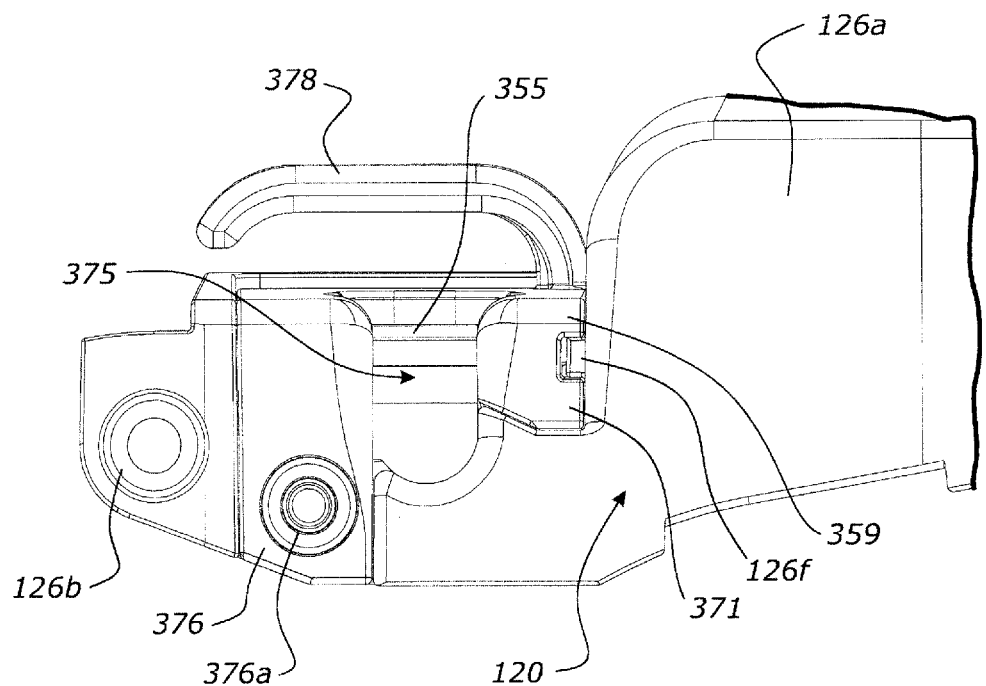
FIG. 50 is a bottom view showing the power cord retainer coupled to the battery cover.
Figure 51:
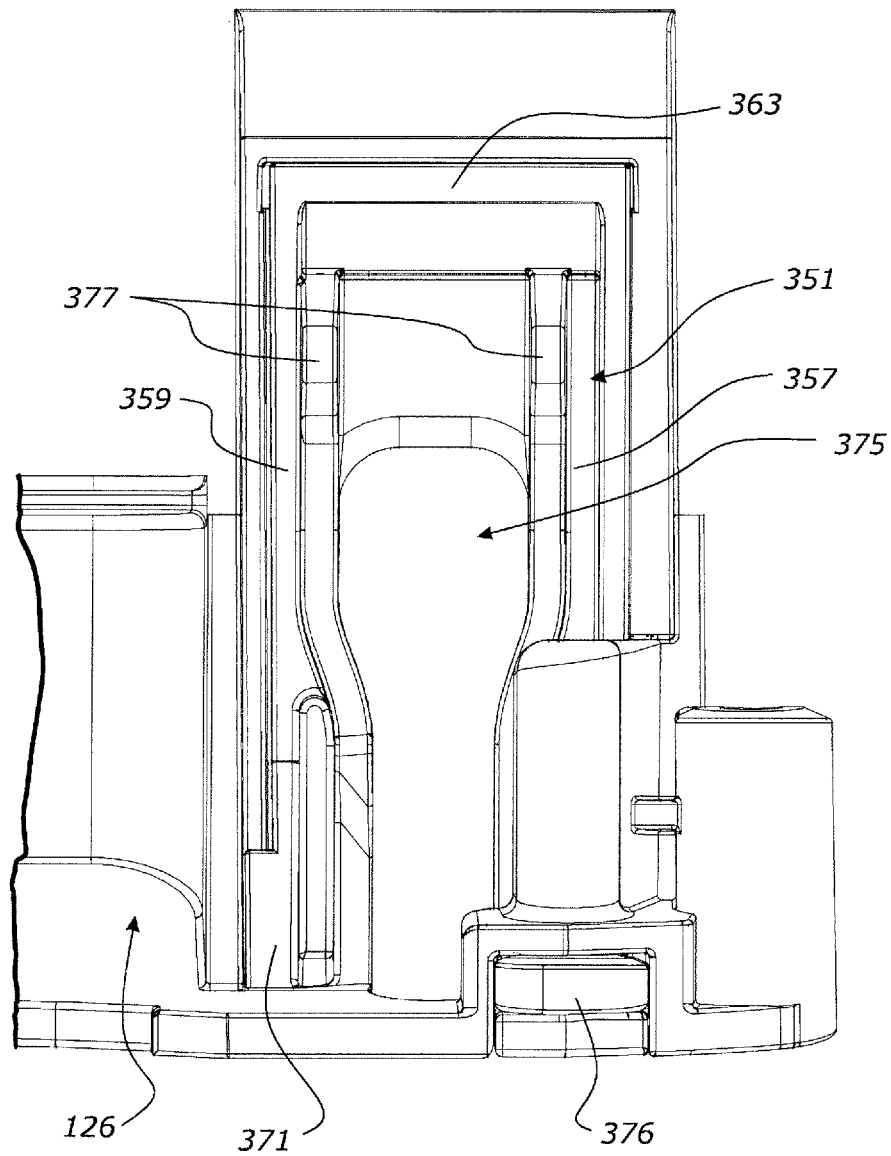
FIG. 51 is a front view of the coupled power cord retainer and battery cover.

Referring to FIGS. 48a and 48b, the battery cover 126 comprises a receptacle housing 126a for receipt of the battery module 125, fastener apertures 126b for receipt of fasteners to mount the battery cover 126 to the lower chassis 104, upper retention features 126c to interact with complementary mounting features on the lower chassis 104 or upper chassis 102, and a retainer cavity 126d for receipt of the power cord retainer 351.

Referring to FIGS. 45, 46, 48A, and 48B, the power cord retainer 351 comprises an inverted substantially U-shaped body portion 353, with an upper transverse cross-member 355, a right side downwardly extending leg 357, and a left side downwardly extending leg 359 (with the left and right sides viewed from the front of the apparatus 10 in use). The body portion 353 comprises a relatively narrow and tall forward body portion 361 having an upwardly extending upper flange 363 corresponding to the upper transverse cross-member 355. The body portion 353 further comprises a relatively wide and short rearward body portion 365 having a right side outer flange 367 corresponding to the right side leg and a left side outer flange 369 corresponding to the left side leg. The left side leg is further provided with a left side inner flange 371 that is defined by a wedge portion having an upper narrow end and lower wide end. A vertical channel 373 is provided between the left side outer flange 369 and the left side inner flange 371.

A power cord passage 375 is provided between the right side leg 357 and the left side leg 359. The upper part 375a of the passage 375 is wider than the lower part 375b of the passage 375.

Forwardly projecting prongs 377 are provided in an upper section of the body, above the upper part 375a of the power cord passage.

Referring to FIGS. 48A and 48B, the power cord retainer 351 is mounted to the housing 100 by moving the power cord retainer vertically upwardly relative to the lower chassis 104 and battery cover 126. The upper flange 363 of the power cord retainer abuts an upper horizontal lip 126e of the cavity 126d of the battery cover. This lip 126e helps retain the power cord retainer in position. A vertical rib 126f extends downwardly from the lip 126e and abuts the left side outer flange 369 of the power cord retainer 351 to aid the user in correctly aligning the upper flange 363 with the lip 126e. Once fully inserted, the left side inner flange 371 also abuts the vertical rib 126f such that the vertical rib 126f is located in the channel 373 between the left side inner and outer flanges 371, 369, further retaining the power cord retainer 351 in the correct position.

A foot 376 extends forwardly from the lower end of the right side leg 357 and has a fastener-receiving aperture 376a that aligns with, and is complementary to, a fastener-receiving aperture 126e in the cavity 126d of the battery cover 126 when the power cord retainer is fully inserted into the cavity 126d. Once assembled, a fastener, such as a screw, can be inserted through the apertures 376a, 126g to fasten the power cord retainer 351 to the battery cover 126. This assembly is designed such that the power cord retainer 351, and in turn the power cord, are unable to be removed except by a technician.

In the assembled configuration, the prongs 377 of the power cord retainer engage with electrical connecter of the power cord in order to hold it in engagement with the electrical connecter 114 of the apparatus 10. The prongs 377 have a gap between them that allows the cord itself to pass through but not the electrical connector of the power cord. The cord is then passed through the power cord passage 375.

The power cord retainer 351 is also shown as having a clip 378. In the form shown, the clip 378 is on an upper part of the body 353 above the power cord passage 375. The clip 378 can be used to help retain one or more cables. One side of the clip may be open to enable cable(s) to be inserted into the clip.

For example, as shown in FIG. 43, the power panel 331 can also have additional receptacles 344 for additional electrical connecters (such as USB connections) located above the electrical connecter 114 for the power cord. When cables are connected to these electrical connectors in the receptacles 344, the cables can be attached to or received in the clip 378 to help prevent the cable from accidentally being dislodged from the receptacles 344.

FIGS. 52 to 56 show an alternative configuration of the removable component comprising a removable elbow 1171. Unless described differently below, the features, functioning, and options of the removable elbow 1171 are the same as for removable elbow 171, and like reference numerals indicate like parts with the addition of 1000.

Although it is not shown in FIGS. 52-56, the removable elbow 1171 will have one or more seals 173 or sealing elements 175 on the recess 1163b, as described above.

As discussed above in relation to removable elbow 171, the removable elbow 1171 also includes an electrical connection. The elbow 1171 has an inlet for pneumatically connecting to a first accessory for the breathing assistance apparatus 10, such as the liquid chamber 151, an outlet for pneumatically and optionally electrically connecting to a second accessory for the breathing assistance apparatus, such as the patient conduit 16, and a printed circuit board (PCB) electrical connector 1178 for electrically connecting to the breathing assistance apparatus 10 to form an electrical connection with an electrical component in the housing 100. The electrical connector 1178 provides an electrical link between the base unit 50 of the apparatus 10 and the temperature sensors 1176 embedded in the elbow 1171, as well as between the base unit 50 of the apparatus 10 and the conduit 16 (when the conduit has one or more sensors and/or a heating element), via the electrical interconnecting assembly 221 in the housing which is described above. The PCB electrical connector 1178 electrically connects to the electrical interconnecting assembly 221 when the removable elbow 1171 is connected to the housing 100.

The pneumatic inlet connection of the removable elbow 1171 is provided by the humidified gas inlet port 1163, the pneumatic outlet connection is provided by the patient outlet port 1030, and the outlet electrical connection is provided by connectors 1179 that are provided in the chimney 1179a that extends upwardly parallel to an axis of the port 1030.

The humidified gas inlet port 1163 and the patient outlet port 1030 are in fluid communication with each other via a gas flow path in the removable elbow. Electrical connectors 1178, 1179 of the removable elbow are pneumatically isolated from the gas flow path between the humidified gas inlet port 1163 and the patient outlet port 1030, via at least one wall of the removable elbow. For example, the body of the removable elbow may be injection moulded plastic material, with isolated regions provided for the electrical connectors that are separate and isolated from the gas flow path.

Because the portion of the removable elbow, namely PCB electrical connector 1178, that is configured to form the electrical connection with the electrical component in the housing (the electrical interconnecting assembly 221) is pneumatically isolated from the gas flow path of the removable elbow, coupling the removable component to the housing solely provides an electrical connection between the PCB electrical connector 1178 and the electrical interconnecting assembly 221. It does not form a direct pneumatic connection between the gas flow path in the removable elbow 1171 and the housing 100. Instead, the gas flow path in the removable elbow provides a pneumatic connection between the first accessory (the liquid chamber 151) and the second accessory (the patent conduit 30).

In the configuration shown, the PCB electrical connector 178 is partly housed in a housing 1178a that is integrally formed with the elbow. The PCB electrical connector 1178 projects rearwardly from the housing 1178a to insert into an electrical connector on the base unit 50 of the apparatus 10 in a horizontal direction (i.e. the same rearward insertion direction CID in which the liquid chamber 151 connects to the housing 100 of the base unit 50 and the same rearward direction RD in which the shroud 190 connects to the screen carrier 211). As such, the removable elbow 1171 can be horizontally connected to the apparatus in the rearward direction RD, with the liquid chamber 151 being horizontally connected to the two apparatus ports 161, 163 after that. Alternatively, the liquid chamber 151 can initially be connected to the removable elbow 1171, with the assembled liquid chamber 151 and elbow 171 then being connected to the base unit 50 of the apparatus together by moving them in the rearward direction together.

As shown in FIGS. 28 to 36, the PCB electrical connector 1178 of the removable elbow 171 inserts into an electrical interconnecting assembly 221 of the base unit 50 of the apparatus 10. The interconnecting assembly 221 is made up of three components; the socket 231, the PCB 241, and the overmould 251.

As explained above in relation to FIGS. 29 and 30, the socket 231 comprises a housing 232 that defines a receptacle 233 to receive the PCB electrical connector 1178 of the removable elbow 1171. A forward portion 233a of the receptacle 22 has relatively large vertical and horizontal dimensions to receive the housing 1178a of the electrical connector. A rear portion 233b of the receptacle 233 has relatively small vertical and horizontal dimensions to receive the portion of the PCB electrical connector 1178 that projects rearwardly from the housing 1178a. The rear portion 233b is defined between upper and lower ribs 234 that extend into the rear part of the receptacle from upper and lower walls thereof. The rear portion 233b of the receptacle is configured to form a close or tight fit with the PCB electrical connector 1178 to assist with holding the removable elbow 1171 in connection with the socket 231. The forward portion 233a of the receptacle may be configured to form a close or tight fit with the housing 1178a of the PCB electrical connector 178 to assist with holding the removable elbow 1171 in connection with the socket 231. Alternatively, that may form a looser fit.

The housing 1178a of the removable elbow 1171 carries a seal 1182. The seal 1182 is configured to engage against the inner surface of the forward portion 233a of the receptacle 233 of the socket 231 when the removable elbow 1171 is engaged with the electrical interconnecting assembly 221 of the base unit 50 of the apparatus. The seal 1182 provides a pneumatic and/or liquid seal between the housing 1178a of the removable elbow 1171 and the receptacle 233 of the socket 231.

The seal 1182 prevents or reduces breathing gas leak and/or condensate from moving toward the electronics in the removable elbow 1171 and the electrical connector 1178 of the elbow.

The housing 1178a of the removable elbow 1171 comprises a generally annular recess 1178b that extends around the top, sides, and at least part of the bottom of the housing 1178a. The seal 1182 is received in the annular recess 1178b, and projects outwardly beyond adjacent surfaces of the housing 1178a to engage with the inner surface of the forward portion 233a of the receptacle 233 of the electrical interconnecting assembly 221.

The seal 1182 may be a wiper seal. The wiper seal may have a T-shaped cross-section. In the form shown, the wiper seal is a flexible annular rim that runs around the circumference of the housing 1178a. The wiper seal may or may not have a bulbous tip on the seal.

In alternative configurations, the seal 1182 may be an L-seal, X-ring, or O-ring.

The seal 1182 may have a single sealing element as shown. Alternatively, the seal 1182 may have a plurality of sealing elements as described in relation to seal 173 and sealing elements 175. Alternatively, the housing may carry a plurality of seals 1182. Each of the plurality of seals 1182 may have a single sealing element.

The seal 1182 may be made from silicone rubber. In an alternative configuration, the seal 1182 could be made from any suitable elastomer, such as polyurethane. Alternatively, the seal 1182 may be made from thermoplastic elastomer(s) and/or thermoplastic vulcanisate(s), particularly if the seal will be overmoulded onto the removable elbow.

A bottom portion of the housing 1178*a* comprises a cavity 1178*c* for receipt of the PCB electrical connector 1178. In the form shown, the cavity 1178*c* is open to the bottom of the housing and to the distal, rear end of the housing.

The housing comprises one or more engagement features 1178*d* to assist with locating the PCB electrical connector 1178 in the cavity 1178*c* of the housing.

In the form shown, the engagement features 1178*d* comprise one or more downwardly directed projections. The projection(s) is/are configured to extend through complementary aperture(s) in the PCB electrical connector 1178.

The engagement feature(s) 1178*d* may comprise enlarged head(s) to reduce the likelihood of the PCB electrical connector 1178 disconnecting from the engagement features 1178*d*. The enlarged head(s) may be tapered so that a lower end of the head has a smaller transverse diameter than an upper end of the head, to enable the PCB electrical connector to be inserted into the cavity 1178*c* over the heads.

While two engagement features 1178*d* are shown, a single engagement feature 1178*d* or three or more engagement features 1178*d* may be provided.

During an initial stage of assembly of the removable elbow 1171 (FIG. 54), the removable elbow does not have the PCB electrical connector in the cavity 1187*c* of the housing 1178*a*.

The PCB electrical connector 1178 is then inserted into the cavity 1178*c* of the housing 1178*a*, with the engagement feature(s) 1178*d* extending through complementary aperture(s) in the PCB electrical connector. The PCB electrical connector 1178 is partly housed in the cavity 1178*c* of the housing 1178*a* and projects rearwardly from the housing 1178*a*.

The seal 1182 is then overmoulded onto the housing 1178*a*.

Figure 56:
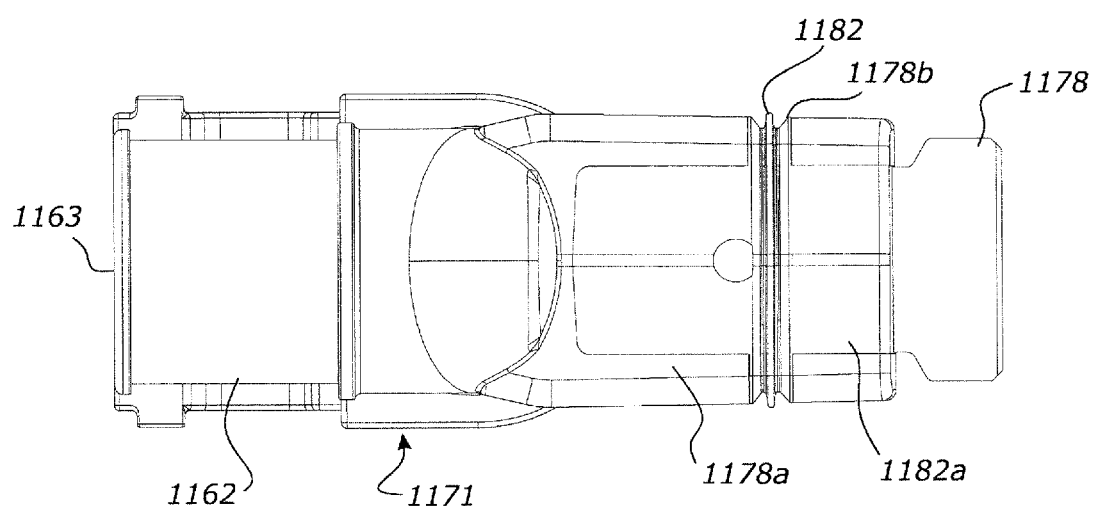
FIG. 56 is a bottom view of the removable elbow following assembly.

As shown in FIG. 56, the overmoulded component comprises a moulded base member 1182*a* that is configured to substantially fill the cavity 1178*c* and cover the underside of the part of the PCB electrical connector 1178 that is housed in the cavity, and the integrally moulded seal 1182. The moulded base member 1182*a* assists with retaining the PCB electrical connector 1178 in the housing 1178*a*.

In an alternative configuration, the seal 1182 may be separately formed and stretched onto the recess 1178*b* of the housing 1178*a*. Alternatively, the seal 1182 may be overmoulded onto the recess of the housing, but the overmoulding may not comprise the integrally formed base member 1182*a*. The base member 1182*a* may be separately formed or may not be present.

One or more tactile features 1172*c* are provided on an upper surface of the flat horizontal tab 1172. In the form shown, the tactile features comprise a plurality of raised features extending upwardly from the upper surface of the tab 1172. The tactile features may comprise a plurality of transverse ribs as shown, but could have any suitable other configuration such as upstanding protrusions that could be circular or any other suitable shape.

The tactile feature(s) 1172*c* assist with a user gripping the tab to pull the removable elbow 1171 out of engagement from the recess 199 in the shroud 190, to remove the removable elbow 1171 from the housing 100 of the breathing assistance apparatus base unit 50.

The tactile feature(s) 1172*c* could alternatively be provided on the removable elbow 171 described above.

Figure 52:
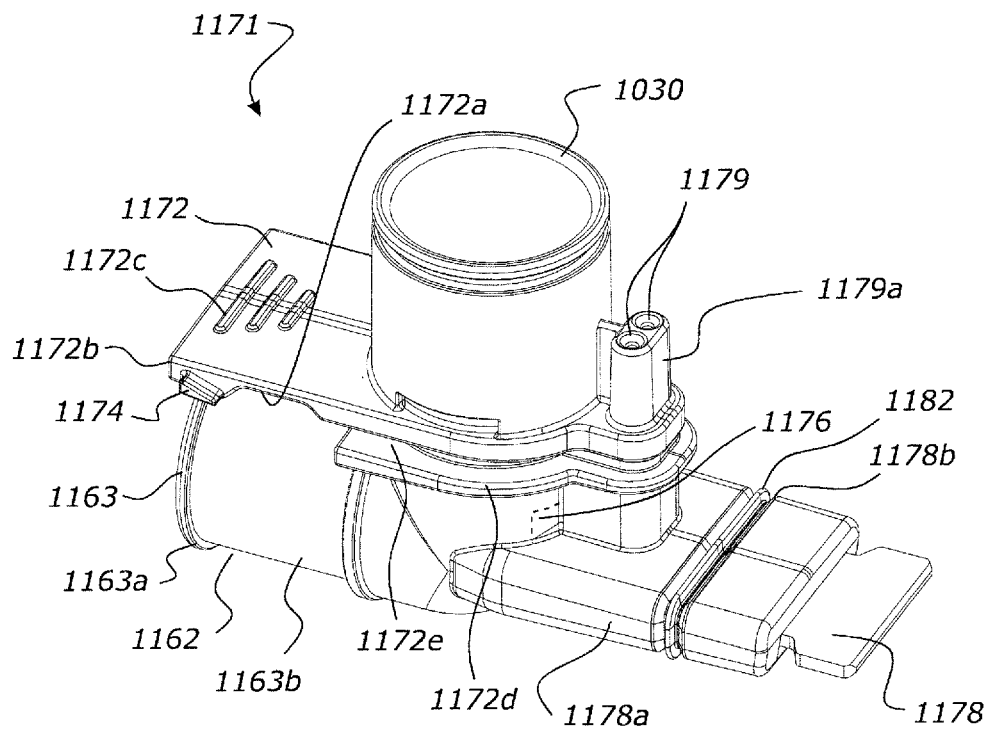
FIG. 52 is a rear/right side overhead perspective view of a removable elbow of the breathing assistance apparatus base unit.
Figure 53:
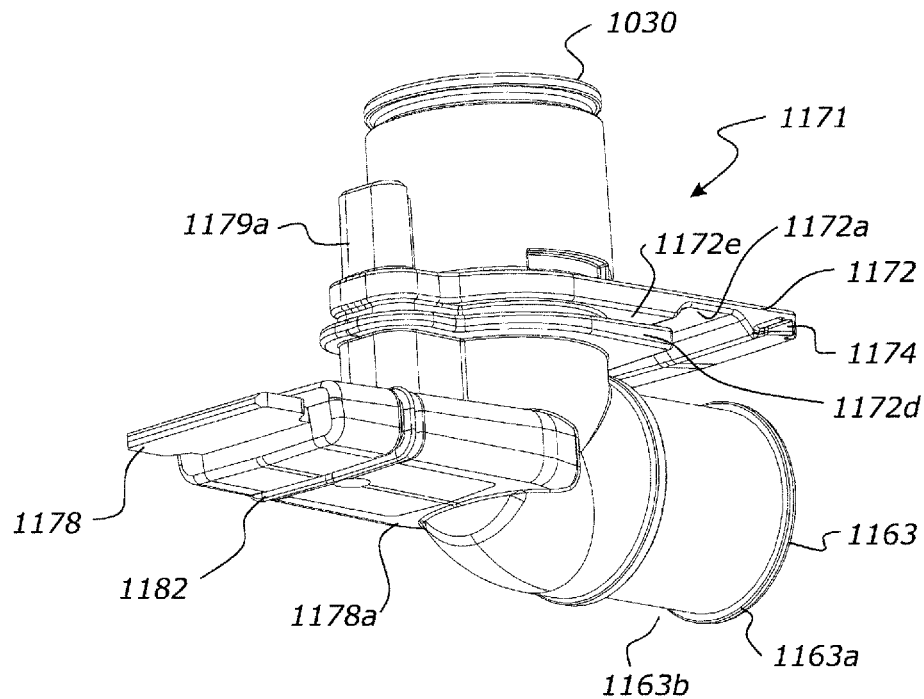
FIG. 53 is a rear/left side perspective view of the removable elbow.
Figure 54:
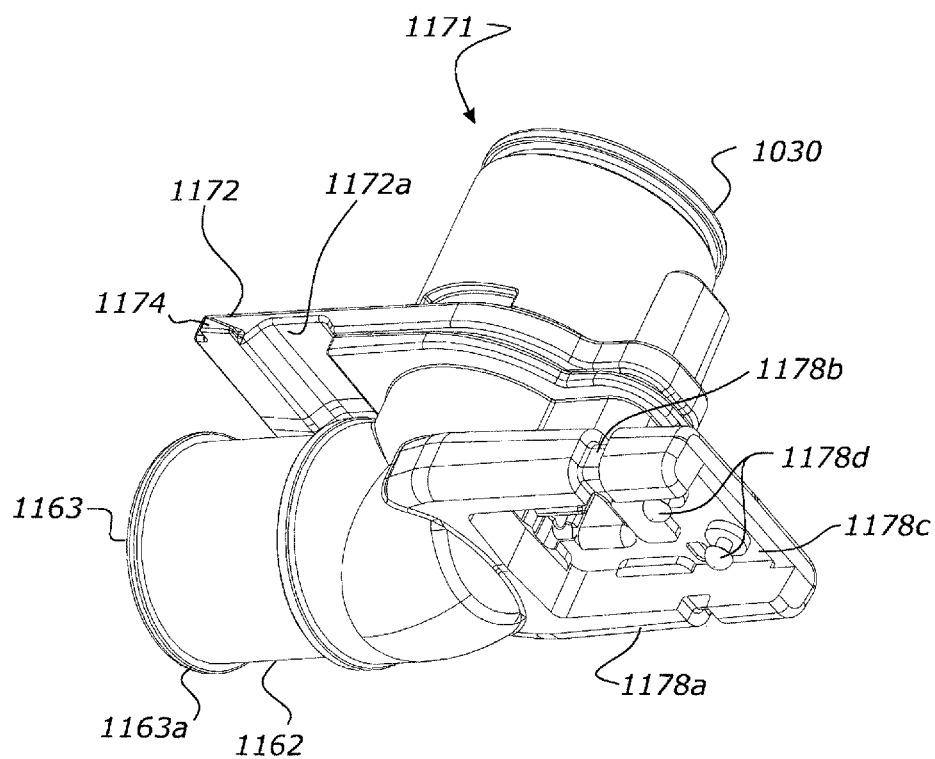
FIG. 54 is a rear/right side perspective view showing the removable elbow from below, during an initial stage of assembly.
Figure 55:
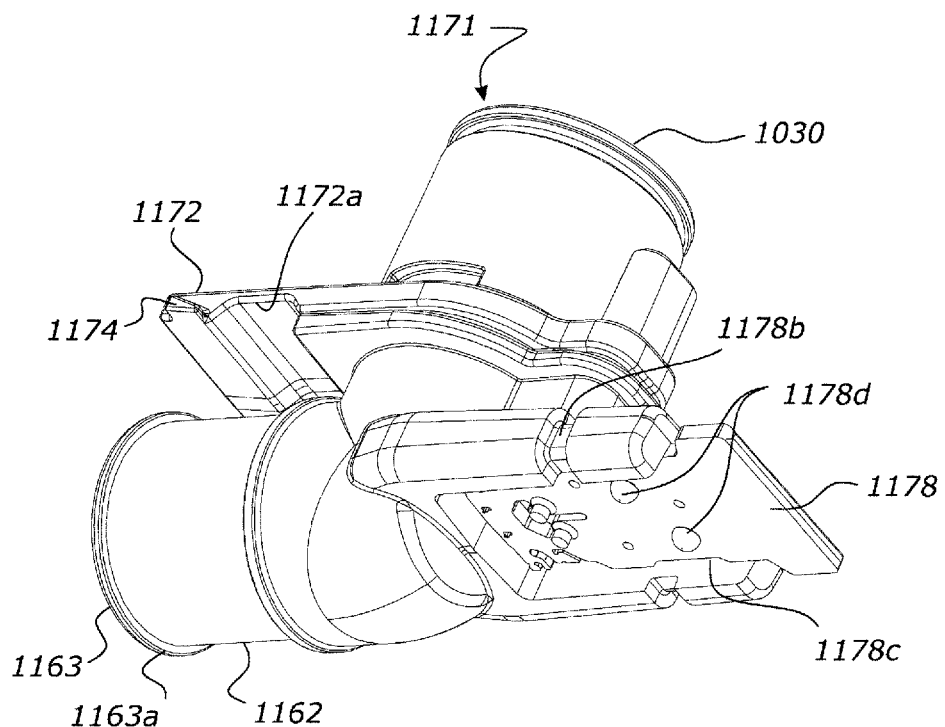
FIG. 55 is a rear/right side perspective view showing the elbow from below, during an intermediate stage of assembly.

As shown in FIGS. 52 and 53, the removable elbow has a flange 1172*d* that is positioned below a portion of body of the elbow that provides the flat horizontal tab 1172. The flange 1172*d* is spaced apart from the underside of the rear portion of the tab 1172 by a space 1172*e*.

In the form shown, the shape of the flange 1172*d* corresponds substantially to the shape of the portion of the body above the space 1172*e*, and has a relatively wide forward region adjacent the patient outlet port 1030 and a relatively narrow rear region adjacent the chimney 1179*a*. Different shapes could be provided.

At least a portion of the flange 1172*d* has a larger dimension than the corresponding portion of the recess 199 of the shroud.

In the form shown, the width of at least the relatively narrow rear region of the flange 1172*d* is larger than the corresponding contoured tapering rear wall region 199*c* of the shroud 190 (FIG. 14). Additionally, or alternatively, the width of the relatively wide forward region of the flange 1172*d* may be wider than a corresponding relatively wide forward region of the recess 199 of the shroud.

The flange 1172*d* forms a close fit with the underside of a portion of the shroud when the removable elbow 1171 is connected to the base unit 50.

The purpose of this is to resist any upward forces placed on the removable elbow (such as when the patient breathing conduit 16 is being removed from the patient outlet port 1130), thereby preventing stress from being placed on the flexible tab 1172 and the electrical connector 1178.

In different configurations, the removable component 1171 may not have an elbow shape, and could instead, for example, have aligned inlet and outlet ports.

Figure 59:
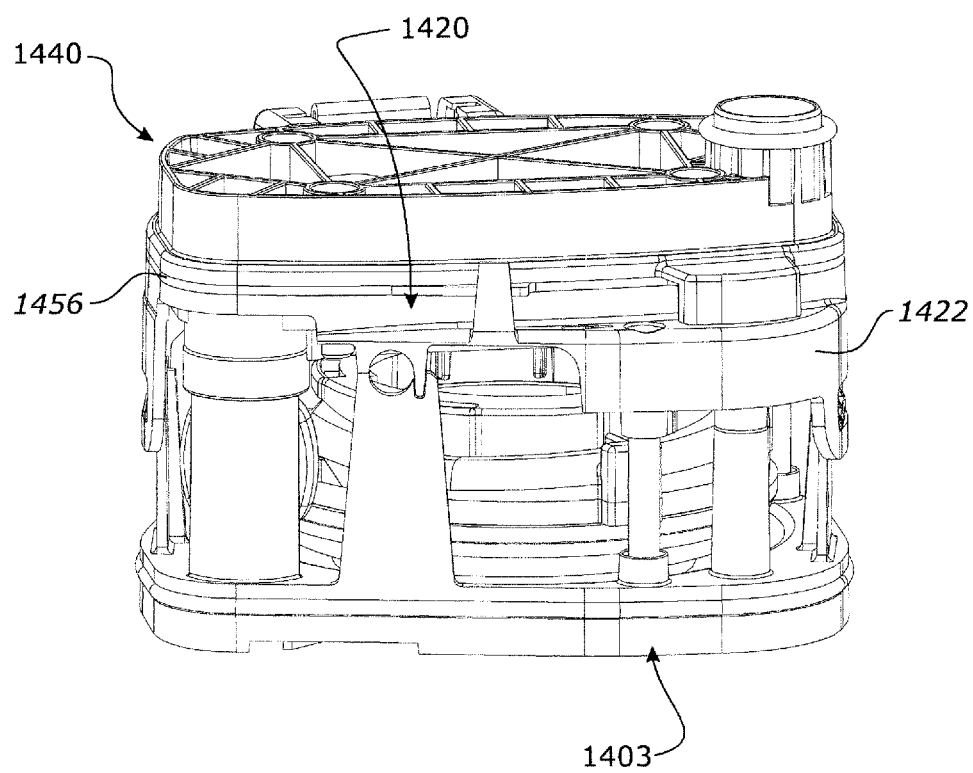
FIG. 59 is a perspective view of the motor module for use in the flow therapy or breathing assistance apparatuses.

Details of a previous configuration of the motor module are disclosed WO2016/207838A9 (WO'838). The contents of that specification are incorporated herein in their entirety by way of reference. In particular, WO '838 discloses the motor module comprising a sensing layer and comprising three main components; a base 1403, a cover layer 1440, and a sensing layer 1420 sandwiched between the base 1403 and the cover layer 1440. Those components are shown in FIG. 59.

The motor module has a sealed air or gas flow path between the base 1403 and the cover layer 1440, such that gases are prevented from escaping and moving towards the electronics of the breathing assistance apparatus. In that configuration, the seal used could be a soft seal such as an O-ring. These types of seals would typically rely on a compressive force generated by the fasteners that retain the three layers of the motor module together. That configuration uses two soft seals; one for sealing between the upper surface of the base 1403 and the lower surface of sensing layer 1420, and one for sealing between the lower surface of the cover layer 1440 and the upper surface of the sensing layer 1420. Each seal is located in a groove located on either the sensing layer 1420 or the base 1403 or the cover layer 1440 in order properly position and retain the seals. Alternatively, the seals may be overmoulded onto one layer and the other layer is positioned on top of the layer including the overmoulded seal to sandwich the seal.

The electronics of the breathing assistance apparatus are positioned in the low pressure region of the main housing of the apparatus to cause a tortuous path which decreases the likelihood of liquid or oxygen ingress to the electronics. The portion of the PCB 1456A comprising the electronics components is positioned 'outside' the seals—that is, it is outside the bulk gas flow. The portion of the PCB 1456 comprising the sensors is inside the flow path and is sealed from the outside by the seals pressing tightly against the PCB 1456. Therefore, liquid or oxygen ingress may be at least substantially prevented.

The cover layer 1440 may be coupled to the gas flow path and sensing layer 1420 using fasteners such as screws. The fasteners sandwich the two sections together providing a compressive force to seal the seals 2423, 2443 against the PCB board 1456. Any suitable number of apertures may be provided for receipt of the screws. Washers could be used on the underside of the screws. To minimise the chance of leakage around the screws to the low pressure region (which could impact performance), ridges could be added to the bosses on which the head of the screw will sit once inserted. Alternatively, once the screws have been inserted, adhesive or filler could be used to seal any possible openings. Alternatively, the cover layer 1440 could comprise clips or adhesive features to couple with the gas flow path and sensing layer 1420 to seal between the layers when force is applied.

Features of an alternative seal to the soft seals will now be described.

Figure 60:
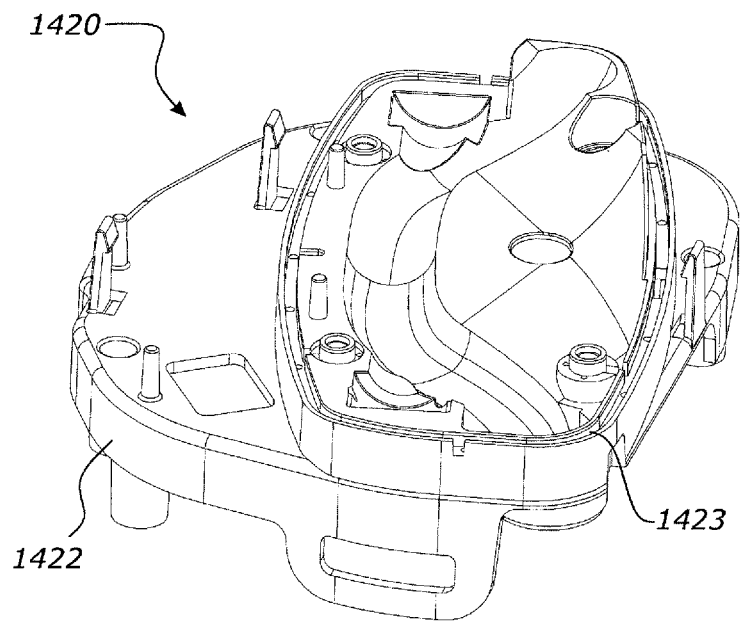
FIG. 60 is an overhead perspective view of an outlet gas flow path and sensing layer of the motor module of FIG. 59, which forms a lower part of a gas flow path.
Figure 61:
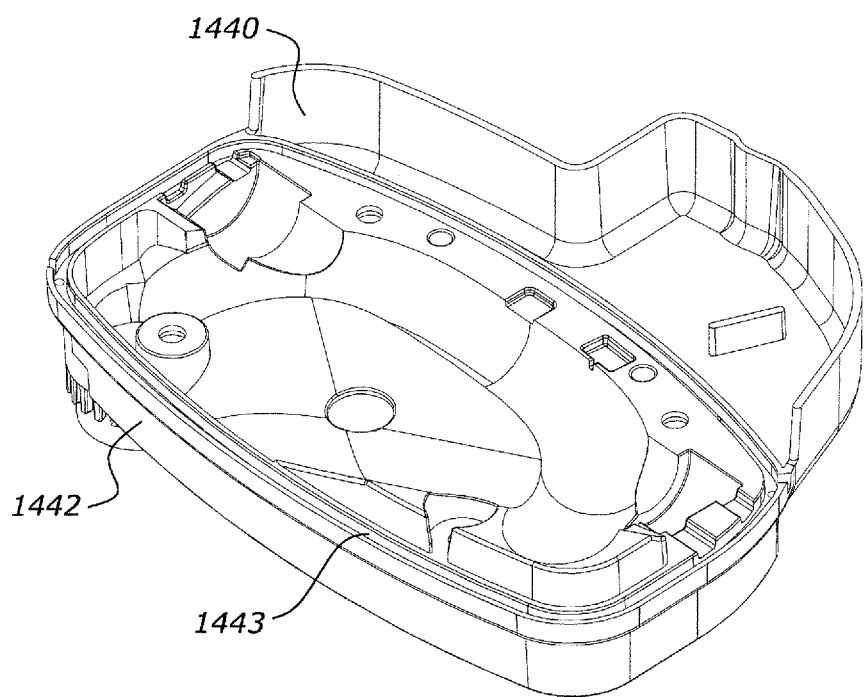
FIG. 61 is an underside perspective view of a cover layer of the motor module of FIG. 59, which forms an upper part of a gas flow path.

As shown in FIGS. 60 and 61, an upper side of the body 1422 of the sensing layer 1420 is provided with a groove 1423 for receipt of a seal 2423 (described in more detail below) to seal against an underside of the PCB 1456. The seal 2423 also seals against an underside of the cover layer 1440. A lower side of the body 1442 of the cover layer 1440 is provided with a groove 1443 for receipt of a seal 2443 (also described in more detail below) to seal against the upper side of the PCB 1456.

Figure 62A:
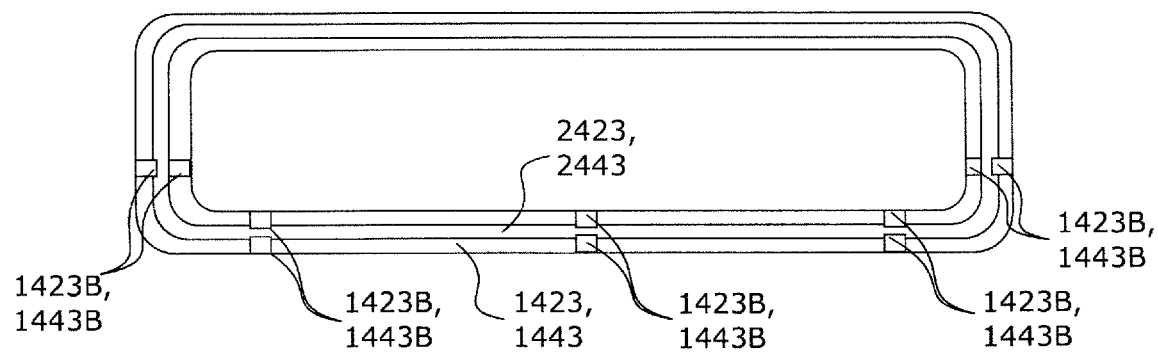
FIG. 62A is a schematic view of a sealing arrangement for the PCB of the motor module of FIG. 59.
Figure 62B:
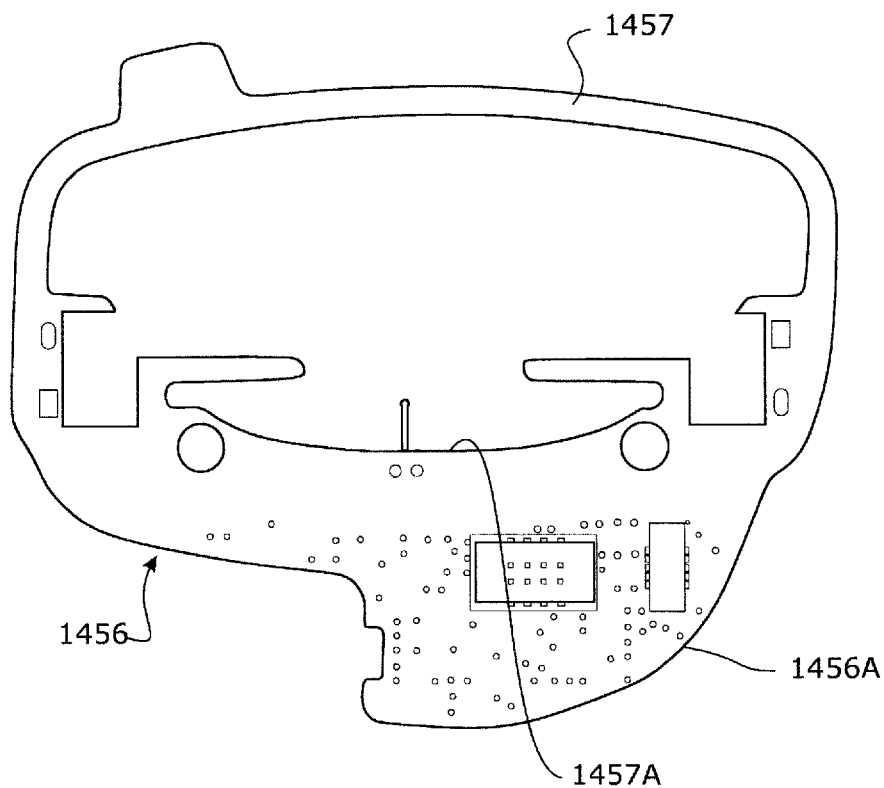
FIG. 62B is an overhead perspective view of the PCB of the motor and/or sensor sub-assembly of FIG. 59.

FIG. 62 is a schematic of a groove 1423/1443 retaining a seal 2423/2443. The grooves 1423, 1443 are advantageously provided with inwardly-directed projections 1423B, 1443B (shown more clearly in FIG. 62A) to assist with maintaining the seals 2423, 2443 in position in the grooves.

The seals 2423, 2443 seal the high pressure region of the motor module, as gasses passing through the gas flow path have been pressurised by the blower. The seals 2423, 2443 prevent gases from escaping and moving towards the electronics of the apparatus. The seals 2423, 2443 also prevent fluid ingress, for example, if there is condensation on the sensing board, the condensation is prevented from coming into the gases flow.

Figure 65:
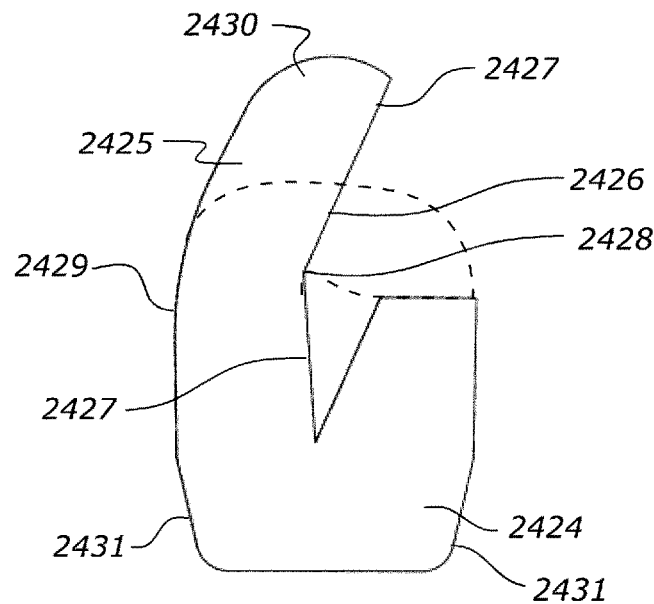
FIG. 65 is a cross-section of the seals of FIGS. 63 and 64, with an exemplary bent configuration of the seals shown in broken lines.

As shown in FIG. 65, each seal 2423, 2443 has a fixed portion 2424 and a flexible portion 2425. With reference to FIG. 65, the fixed portion 2424 is shaped to conform to the groove 1423, 1443 that retains the seal. The lower region of the seal may have tapered sides 2431 to fit into the groove 1423, 1443 and create a friction fit. The tapered sides are shown in FIG. 65. The groove may be a groove 1423 in the base 1403 or a groove 1443 in the cover layer 1440 for example. The lower part of the seal 2423 is a similar size and shape as the size and shape of the groove 1423. Once the seal 2423 is assembled with the base 1403, the fixed portion will be secured in the groove 1423 and remain stationary relative to the base 1403.

With reference to FIG. 65, the flexible portion 2425 of the seal is structured to curve or angle towards one side whilst in the unflexed position. The flexible portion has a generally concave kinked surface 2426 formed by two flat surfaces 2427 that meet at a corner 2428. The flexible portion also has a convex curved surface 2429, which together with the generally concave surface 2426, gives the flexible portion 2425 a curved shape. This curved shape causes the flexible portion 2425 of the seal to flex towards one side when the seal engages with the sealing surface of the sensing layer 1420. In the orientation of FIG. 65, the flexible portion flexes to the right side. In particular, the flexible portion 2425 is structured such that it curves or angles inwardly towards the gas flow path.

The described shape extends around the entire seal 2423, 2443.

The flexible portion 2425 is configured to flex when a compressive force is applied at or near a free end 2430 of the flexible portion 2425 in a direction towards the fixed portion 2424. Such a compressive force is applied when the flexible portion 2425 is pressed against an opposing sealing surface. Once the seal 2423 is assembled with the base 1403, the flexible portion 2425 is able to flex relative to the fixed portion 2424 and the base 1403. The flexible portion 2425 preferably flexes resiliently—that is, the flexible portion 2425 is biased to return to its at rest position or unflexed position after the compressive force is removed. The biasing force results in a sealing force against the sensing layer 1420 when the contact with the sensing layer 1420 forces the flexible portion 2425 into a flexed position. When moving from the unflexed position to the flexed position, the flexible portion 2425 bends to have a more curved shape than its at rest shape. The free end 2430 moves inwardly and downwardly into the more curved flexed position. In particular, the flexible portion 2425 bends inwardly towards the gas flow path.

Additionally or alternatively to curving, the flexible portion 2425 can flex or bend about the corner 2428. The corner 2428 may be a fold line to assist with folding the seal. The upper flat surface 2427 contacts the opposing flat top surface of the fixed portion 2424 to form the operative seal. In the operative configuration, the flexible portion 2425 and the fixed portion form a closed shape with the upper flat surface 2427 pressed against the opposing flat top surface of the fixed portion 2424. Alternatively, the upper flat surface 2427 may simply rest on the opposing flat top surface. Because the flexible portion 2425 is flexed to contact a portion of the fixed portion 2424, the seal forms a tortuous path for any gases to travel through when the seal is in the operative position or orientation.

The description above refers to the orientation of the seal that is assembled with the base 1403. The orientation of the seal will depend on the groove that the seal is assembled with. The seal that is assembled with the cover layer 1440 is upside down compared to the seal that is assembled with the base 1403. That is, the fixed portion 2424 is above the flexible portion 2425.

An advantage of a seal having a flexible portion 2425 compared with a compressive seal is that a lower force is required for an adequate seal to be produced between the base 1403 and the sensing layer 1420, and/or between the sensing layer 1420 and the cover layer 1440. Additionally, the seal would produce adequate sealing contact between the components in a wider range of positions. As a result, the seal allows for a greater tolerance of the components. For example, there is a greater tolerance for in the event of flexing of the components and/or manufacturing variation.

A further advantage of such a configuration is that any increase in pressure in the gas flow path would result in the flexible portion 2425 of the seal being further biased into the unflexed position. As a result, an increase in pressure in the air path would simply increase the sealing force between the flexible portion 2425 and the sealing surface of the sensing layer 1420. As such, there is a reduced chance of a large pressure resulting in the seal failing.

In use, the flexible portion 2425 together with the fixed portion 2424 form a seal with double/overlapping portions with an air gap in between those portions. If there is a leak of gas from the gas flow path, the gas flow needs to follow tortuous path around the flexible and fixed portions, including crossing the gap between those portions. The tortuous path is due to the curved flexible portion 2425. If there is a leak, any leaked gases have to follow a tortuous path around and through the flexed seal.

The seal is, or comprises, an elastomeric material. The seal preferably comprises a material that exhibits a low amount of material creep (cold flow) over time. Silicone is an example of a material with low material creep. Alternatively, the seal is, or comprises, an elastomeric thermoplastic. One or both seals could be overmoulded into the grooves of the base 1403 and/or cover layer 1440. Alternatively, one or both seals could be formed separately and then subsequently fitted into the corresponding groove 1423, 1443.

Figure 63:
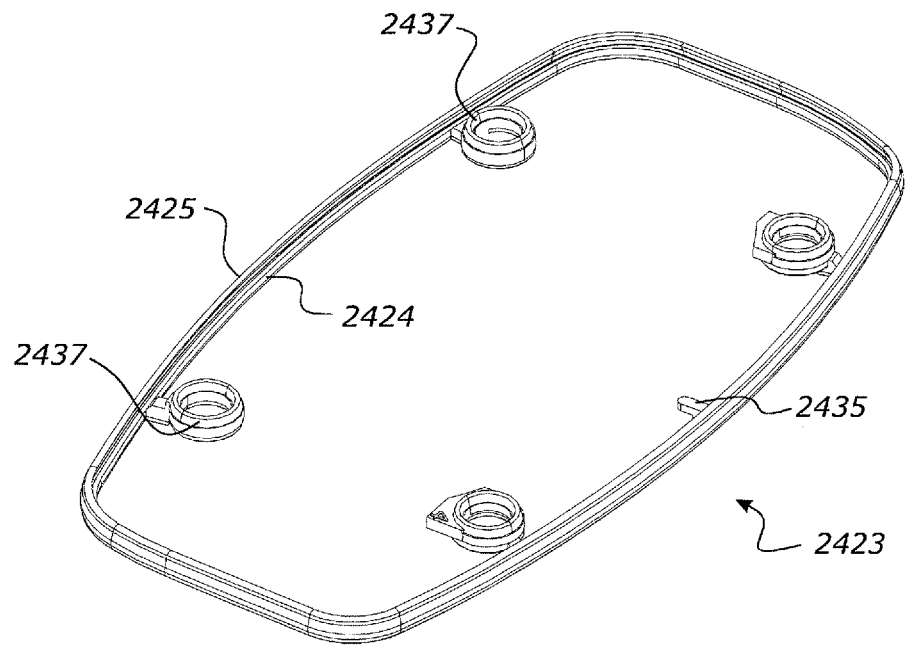
FIG. 63 is a perspective view of a seal for sealing between the base and the sensing layer of the motor module of FIG. 59.
Figure 64:
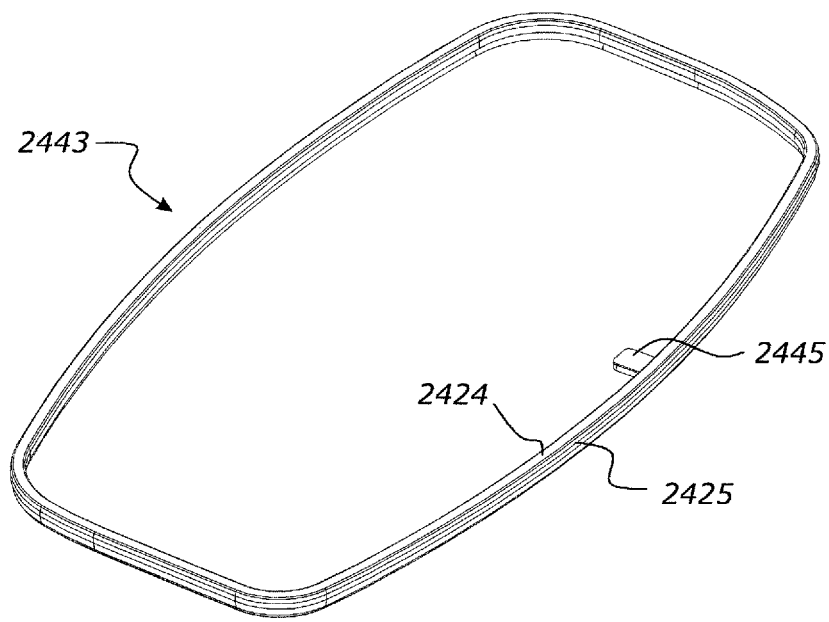
FIG. 64 is a perspective view of a seal for sealing between the cover layer and the sensing layer of the motor module of FIG. 59.

FIGS. 63 and 64 show each seal having a tab 2435, 2445 for assembly and disassembly of the seal with the cover layer or base. FIG. 63 also shows a plurality of integral washers 2437 for sealing around the fasteners that connect the base 1403 and cover layer 1440.

One advantage of this seal 2423, 2443 is it requires a lower compressive force to provide an adequate seal compared to soft seals. In order to achieve the required force when soft seals ae used, the fasteners need to be sufficiently spaced around the sealing region, as slight flexing of the components could cause a portion of the soft seal that is sufficiently spaced from the nearest fastener to fail in producing an adequate seal.

Additionally, the seal is less susceptible to failure if the pressure in the gas flow path reaches a certain threshold. As described above, the configuration of the flexed seal creates a tortuous path.

In WO '838, a seal may be formed between an upper edge of a filter housing of a lower chassis 3202' and a corresponding aperture in an upper chassis 3102'. This seal can be produced by a tongue and groove arrangement. Unless described otherwise herein, the features and functioning of the filter housing/receptacle are the same as the filter housing/receptacle described in WO '838, and the contents of that specification are incorporated herein in their entirety by way of reference.

In the present configuration, an alternative to the tongue and groove arrangement is provided. In the present configuration, the upper chassis 3102' and lower chassis 3202' of the main housing 100 of the base unit 50 are configured such that when they are assembled together, a cavity 6701 is present between an upper surface of the lower chassis 3202' and a lower surface of the upper chassis 3102', as shown in FIG. 67.

A seal 6703 is placed between these two surfaces, thereby blocking the ingress of gases into the space between the upper and lower chassis.

Figure 67:
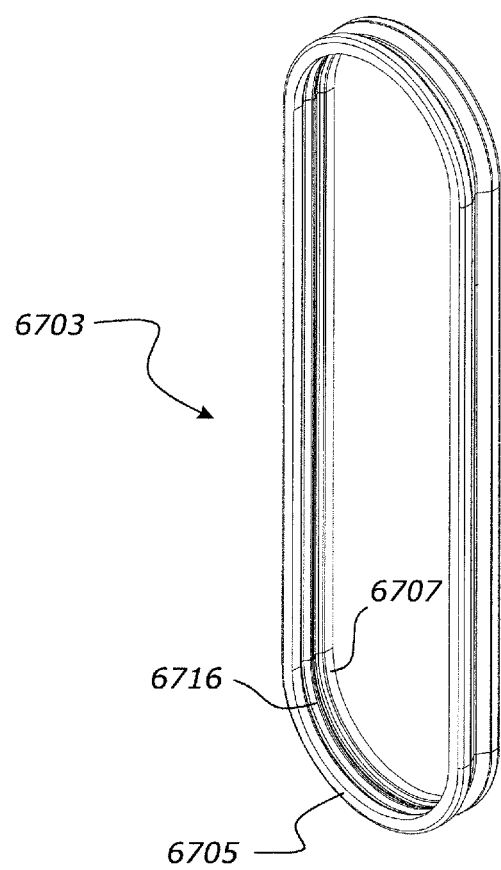
FIG. 67 is a perspective view of a filter receptacle seal.
Figure 68A:
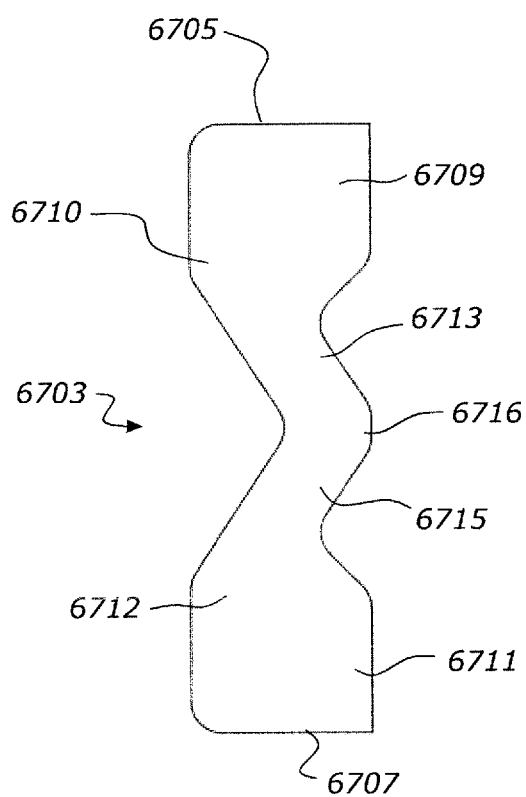
FIGS. 68A and 68B are cross-sectional views of the seal of FIG. 67 in non-compressed and compressed states.
Figure 68B:
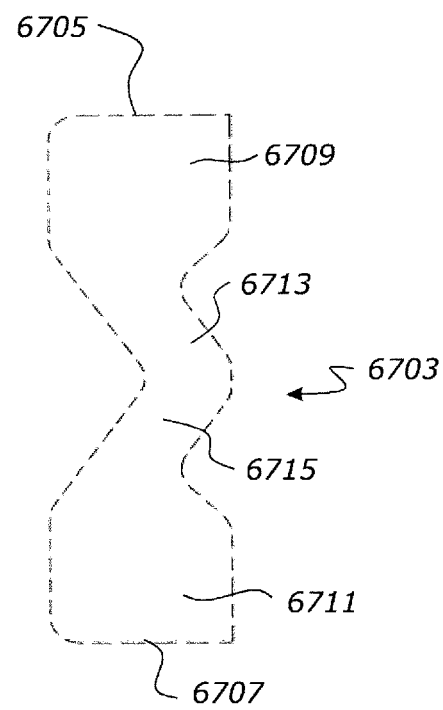

The seal 6703 has the form shown in FIG. 67 and the cross-section shown in FIGS. 68A and 68B.

The general shape of the seal 6703 is a shape that corresponds substantially to the shape of the body of the filter 271. The transverse shape and dimensions of the seal corresponds to the shape and dimensions of the cavity 6701.

Figure 66:
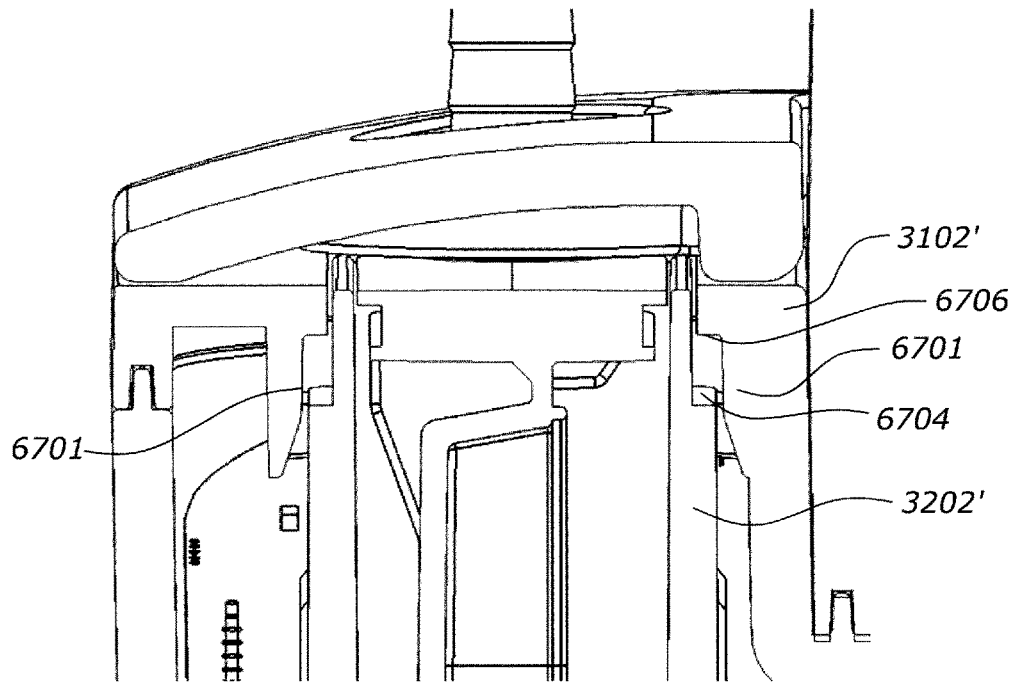
FIG. 66 is a cross-section showing a cavity between an upper surface of the lower chassis and a lower surface of the upper chassis of the main housing of the base unit of the breathing assistance apparatus.

FIGS. 68A and 68B are cross-sectional views of the seal of FIG. 66 in non-compressed and compressed states. The seal 6703 would initially be in a non-folded state as shown in FIG. 68A. In this state, the vertical dimension of the seal 6703 would exceed the vertical dimension of the cavity 6701. During assembly the upper surface 6705 of the seal would sealingly contact the lower surface 6704 of the upper chassis 3102', and the lower surface 6707 of the seal would sealingly contact the upper surface 6706 of the lower chassis 3202'.

As shown in FIGS. 68A and 68B, the seal 6703 has an undulating shape with peaks and troughs. The seal 6703 has a substantially horizontal upper portion 6709 and a substantially horizontal lower portion 6711. A first inner portion 6713 extends at an angle inwardly and downwardly from the left side of the upper portion 6709, forming a bend 6710. A second inner portion 6715 extends at an angle inwardly and upwardly from the left side of the lower portion 6711 forming a bend 6712. The first inner portion 6713 and the second inner portion 6715 met at the inner side (right side of FIGS. 67a and 67b) of the seal forming bend 6716. The upper portion, lower portion, and inner portions form a sideways M-shaped seal. The seal 6703 is symmetrical about a horizontal centre line. This symmetry advantageously ensures that the seal 6703 deforms evenly when a vertical force is applied. Additionally, the sideways M-shape allows the seal 6703 to bend in the central region whilst the upper and lower surfaces of the seal remain substantially horizontal. In an alternative configuration, the seal 6703 may have fewer bends and/or fewer inner portions, such as a Z shape. In a further alternative configuration, the seal 6703 may have more bends or inner portions.

Once assembled, the contact described above would cause the seal 6703 to deform into a folded position. The seal would deform via a folding motion instead of simply compressing. As such, the seal 6703 is capable of a greater range of motion resulting from the same force when compared with a typical compressive seal. This allows the seal 6703 to be able to conform to the shape of the cavity 6701 even in the event of significant variations resulting from flexing of the components, manufacturing variation, and the like.

When compressed from the orientation in FIG. 68A to the compressed orientation in FIG. 68B, the portions of the seal flex or fold such that the upper portion 6709 and the lower portion 6711 move closer together. The upper surface 6705 and lower surface 6707 form sealing surface that seal the filter to prevent pressurised gases from leaking out of the filter module 271 and into the housing of the main control and power circuit boards. The biasing force from the central undulating shape creates a seal.

The seal 6703 is manufactured from an elastomeric material. The seal 6703 is manufactured from silicone, which exhibits low amounts of material creep (cold flow) over time. Alternatively, the material may be manufactured from an elastomeric thermoplastic.

This cavity 6701 is located at a substantial distance from the fasteners that secure the lower chassis 3202' to the upper chassis 3102'. As such, variations in the components or misalignments between the components could result in a leak at the cavity 6701. A seal 6703 having the features and functions described herein allows for variations while still providing a sealing function.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. Any one or more features from any of the configurations may be used in combination with any one or more features from any of the other configurations.

The features are described with reference to a breathing assistance apparatus that can deliver heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the features may be used with an apparatus for a different purpose. The apparatus may be a high flow therapy apparatus, or may be a low flow therapy apparatus. For example, the features may be provided in an apparatus for providing continuous positive airway pressure (CPAP), which may deliver gases (humidified or otherwise) at lower flow rates, or may be provided in a medical insufflation apparatus.

The features could be used in a stand-alone humidifier. The standalone humidifier may have a housing, a recess 108 for receipt of the liquid chamber 151, and a heater plate 140, but may not have a motor unit. The standalone humidifier may receive gases from an external source.

Accordingly, an alternative form breathing assistance apparatus 10 may be a standalone humidifier apparatus comprising a base unit 50 defining a main housing and a humidifier 12.

The standalone humidifier apparatus can deliver heated and humidified gases for various medical procedures, including respiratory therapy, laparoscopy, and the like. These apparatuses can be configured to control temperature and/or humidity. The apparatuses can also include medical circuits comprising various components that can be used to transport heated and/or humidified gases to and/or from patients. For example, in some breathing circuits, gases inhaled by a patient are delivered from a heater-humidifier through an inspiratory tube or conduit. As another example, tubes can deliver humidified gas (commonly $CO_2$) into the abdominal cavity in insufflation circuits. This can help prevent desiccation or 'drying out' of the patient's internal organs, and can decrease the amount of time needed for recovery from surgery. Heater wires may extend inside of at least a portion of the tubing forming the circuit to prevent or at least reduce the likelihood of the formation of significant condensation.

A standalone humidifier apparatus would typically include a base unit 50 and a humidifier liquid chamber 151. The base unit 50 can comprise a heater plate 140. The liquid chamber 151 can be configured to hold a volume of a liquid, such as water. The heater plate can be configured to heat the volume of liquid held within the liquid chamber 151 to produce vapour.

The liquid chamber 151 is removable from the base unit to allow the liquid chamber to be more readily sterilized or disposed, or to re-fill the chamber with liquid. The body of the liquid chamber 151 can be formed from a non-conductive glass or plastics material but the liquid chamber can also include conductive components. For instance, the liquid chamber can include a highly heat-conductive base (for example, an aluminum base) contacting or associated with the heater plate on the heater base.

The base unit can also include electronic controls such as a master controller. In response to user-set humidity or temperature values input via a user interface and other inputs, the master controller determines when (or to what level) to energize the heater plate 140 to heat the liquid within the liquid chamber 151.

The standalone humidifier apparatus can include a flow generator to deliver gases to the liquid chamber. In some configurations, the flow generator can comprise a ventilator, blower, or any other suitable source of pressurized gases suitable for breathing or use in medical procedures. The flow generator may be positioned in the base unit 50.

Alternatively, the standalone humidifier apparatus may comprise just the base unit 50 and the liquid chamber 151, and may be used with a separate or remote flow generator. The base unit 50 may be configured to fluidly connect to the separate or remote flow generator.

Therefore, the flow generator that is used with a standalone humidifier apparatus may be a wall gases source, ventilator, blower, or gas tank for example.

A standalone humidifier apparatus can be used with breathing therapies, positive pressure apparatus, noninvasive ventilation, surgical procedures including but not limited to laparoscopy, and the like. Desirably, the humidifier apparatus can be adapted to supply humidity or vapour to a supply of gases. The humidifier apparatus can be used with continuous, variable, or bi-level PAP systems or other form of respiratory therapy. In some configurations, the humidifier apparatus can be integrated into a system that delivers any such types of therapy.

An exemplary standalone humidifier apparatus is described in WO 2015/038013. The contents of that specification are incorporated herein in their entirety by way of reference.

The standalone humidifier apparatus may have any one or more of the features described or shown herein.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to when the apparatus is in a typical in-use position and/or with reference to particular orientations shown in the figures, and are used to show and/or describe relative directions or orientations.

The invention claimed is:
1. A breathing assistance apparatus comprising:
  a housing comprising an engagement feature;
  an electrical component in the housing, the electrical component comprising a receptacle;
  a removable component configured as an elbow comprising:
    a gas inlet port extending along a first axis,
    a gas outlet port extending along a second axis perpendicular to the first axis,
    an electrical connector extending from the elbow and configured to be a close or tight fit in the receptacle of the electrical component to assist with holding the removable component in connection with the electrical component,
    a tab with a terminal end portion that can be flexed relative to the rest of the removable component, the tab extending from the elbow in a direction that is parallel to the first axis, wherein the tab and the electrical connector are positioned on opposite sides of the second axis and extend in opposite directions from the elbow, wherein an engagement feature is provided on the terminal end portion of the tab and is configured to engage with the engagement feature of the housing such that the removable component is inhibited from disconnecting from the housing in the absence of actuating the terminal end portion of the removable component to flex the tab.

2. The breathing assistance apparatus according to claim 1, wherein the tab comprises a thinned portion adjacent the terminal end portion.

3. The breathing assistance apparatus according to claim 1, wherein the engagement feature of the removable component comprises a protrusion, and wherein the engagement feature of the housing comprises a complementary engagement recess.

4. The breathing assistance apparatus according to claim 3, wherein the protrusion extends outwardly from a side of the terminal end portion.

5. The breathing assistance apparatus according to claim 4, wherein the housing further comprises an additional engagement feature and the removable component further comprises an additional engagement feature, wherein each the engagement feature and the additional engagement feature of the removable component are a protrusion extending outwardly from opposite sides of the terminal end portion, and wherein each the engagement feature and the additional engagement feature of the housing are complementary engagement recesses.

6. The breathing assistance apparatus according to claim 1, wherein the engagement feature of the removable component and the engagement feature of the housing are configured such that inserting the removable component into the housing will cause the terminal end of the tab to flex.

7. The breathing assistance apparatus according to claim 1, wherein the electrical component comprises a socket, and wherein the removable component comprises a seal that is configured to engage against a portion of the socket.

8. The breathing assistance apparatus according to claim 7, wherein the seal comprises a wiper seal.

9. The breathing assistance apparatus according to claim 7, wherein the seal comprises one or more sealing elements.

10. The breathing assistance apparatus according to claim 7, wherein the seal comprises an overmoulded seal.

11. The breathing assistance apparatus according to claim 10, wherein the electrical connector comprises a printed circuit board (PCB) electrical connector, wherein the PCB electrical connector is partly housed in a cavity of the removable component, and wherein the removable component comprises a moulded base member that is integrally moulded with the seal and that covers a part of the PCB electrical connector that is housed in the cavity.

12. The breathing assistance apparatus according to claim 1, wherein the tab extends in a direction that is parallel to the first axis of the gas inlet port.

13. The breathing assistance apparatus according to claim 1, wherein the tab extends to the distal end and terminates at a position that is substantially in line with an inlet opening of the gas inlet port.

* * * * *